(12) United States Patent
Narwal et al.

(10) Patent No.: US 11,446,377 B2
(45) Date of Patent: *Sep. 20, 2022

(54) ANTI-B7-H1 AND ANTI-CTLA-4 ANTIBODIES FOR TREATING NON-SMALL CELL LUNG CANCER

(71) Applicant: MEDIMMUNE, LLC, Gaithersburg, MD (US)

(72) Inventors: Rajesh Narwal, Gaithersburg, MD (US); Paul Robbins, Gaithersburg, MD (US); Joyson Karakunnel, Gaithersburg, MD (US); Mohammed Dar, Gaithersburg, MD (US)

(73) Assignee: MEDIMMUNE, LLC, Gaithersurg, MD (US)

( * ) Notice: Subject to any disclaimer, the term of this patent is extended or adjusted under 35 U.S.C. 154(b) by 193 days.

This patent is subject to a terminal disclaimer.

(21) Appl. No.: 16/256,022

(22) Filed: Jan. 24, 2019

(65) Prior Publication Data

US 2019/0240324 A1    Aug. 8, 2019

Related U.S. Application Data

(63) Continuation of application No. 14/710,101, filed on May 12, 2015, now Pat. No. 10,232,040.

(60) Provisional application No. 62/114,336, filed on Feb. 10, 2015, provisional application No. 62/105,992, filed on Jan. 21, 2015, provisional application No. 61/992,658, filed on May 13, 2014.

(51) Int. Cl.
```
A61K 39/395    (2006.01)
C07K 16/28     (2006.01)
A61K 39/00     (2006.01)
```

(52) U.S. Cl.
CPC ...... *A61K 39/3955* (2013.01); *C07K 16/2818* (2013.01); *C07K 16/2827* (2013.01); *A61K 2039/507* (2013.01); *A61K 2039/54* (2013.01); *A61K 2039/545* (2013.01); *C07K 2317/21* (2013.01); *C07K 2317/94* (2013.01)

(58) Field of Classification Search
CPC .......... C07K 16/2818; A61K 2039/507; A61K 2039/54; A61K 2039/545
USPC ................... 424/133.1, 142, 142.1
See application file for complete search history.

(56) References Cited

U.S. PATENT DOCUMENTS

| | | | |
|---|---|---|---|
| 9,375,489 B2 | 6/2016 | Govindan et al. | |
| 9,744,234 B2 | 8/2017 | Mpofu et al. | |
| 9,938,356 B2 * | 4/2018 | Hay | A61K 47/6825 |
| 10,232,040 B2 * | 3/2019 | Narwal | A61P 43/00 |
| 10,287,362 B2 * | 5/2019 | Hay | C07K 16/2818 |
| 10,556,968 B2 * | 2/2020 | Hay | A61P 35/00 |
| 2012/0328693 A1 | 12/2012 | Lan et al. | |
| 2015/0306243 A1 | 10/2015 | Govindan et al. | |
| 2016/0015805 A1 | 1/2016 | Azab et al. | |
| 2016/0060344 A1 * | 3/2016 | Narwal | A61P 35/00 424/142.1 |
| 2016/0194407 A1 | 7/2016 | Hay et al. | |
| 2016/0256562 A1 | 9/2016 | Govindan et al. | |
| 2016/0304607 A1 | 10/2016 | Sadineni et al. | |
| 2016/0347848 A1 * | 12/2016 | Hammond | A61K 39/3955 |
| 2019/0359715 A1 * | 11/2019 | Kurland | A61K 9/0019 |

FOREIGN PATENT DOCUMENTS

| | | |
|---|---|---|
| AU | 2011203119 | 7/2011 |
| AU | 2011203119 A1 | 7/2011 |
| WO | 2008100562 | 8/2008 |
| WO | WO 2008100562 A2 | 8/2008 |
| WO | 2013169388 | 11/2013 |
| WO | 2013172926 | 11/2013 |
| WO | 2013173223 | 11/2013 |
| WO | WO 2013169388 A1 | 11/2013 |
| WO | WO 2013172926 A1 | 11/2013 |
| WO | WO 2013173223 A1 | 11/2013 |
| WO | WO 2014066834 A1 | 1/2014 |
| WO | 2014066834 | 5/2014 |

OTHER PUBLICATIONS

Antonia et al (Lancet Oncol. Mar. 2016 ; 17(3): 299-308).*
Planchard et al. (Annals of Oncology 31(5): 609-618 (2020)).*
Clinincaltrials.gov (NCT01693562, pp. 1-27 (Jun. 24, 2021)).*
Callahan, M.K., et al., "At the Bedside: CTLA-4- and PD-1-blocking antibodies in cancer immunotherapy," Journal of Leukocyte Biology, 94(1): 41-53 (2013).
Champiat, S., et al., "Incorporating Immune-Checkpoint Inhibitors into Systemic Therapy of NSCLC," Journal of Thoracic Oncology, 9(2): 144-153 (2014).
Cho, D., et al., "Clinical activity, safety, and biomarkers of MPDL3280A, an engineered PD-L1 antibody in patients with metastatic renal cell carcinoma (mRCC)," Journal of Clinical Oncology, 31(15): (2013).
Horn, L., et al., "An analysis of the relationship of clinical activity to baseline EGFR status, PDL1 expression and prior treatment history in patients with non-small cell lung cancer (NSCLC) following PD-L1 blockade with MPDL3280A (anti-PDL1)," Journal of Thoracic Oncology, 8(2): S364.
Kyi, C., et al., "Checkpoint blocking antibodies in cancer immunotherapy," FEBS Letters, 588(2): 368-376 (2013).
Ludwig Institute for Cancer Research: "A Phase 1 Study to Evaluate MEDI4736 in Combination with Tremelimumab," ClinicalTrials.gov (2013).
Medimmune: "A Phase 1b Study of MEDI4736 in Cominbation With Tremelimumab in Subjects With Advanced Non-small Cell Lung Cancer," ClinicalTrials.gov (2013).

(Continued)

*Primary Examiner* — Lynn A Bristol
(74) *Attorney, Agent, or Firm* — McDonnell Boehnen Hulbert & Berghoff LLP

(57) ABSTRACT

Provided herein are methods of treating non-small cell lung cancers comprising administering an effective amount of MEDI4736 or an antigen-binding fragment thereof and tremelimumab or an antigen-binding fragment thereof.

13 Claims, 41 Drawing Sheets

Specification includes a Sequence Listing.

(56) References Cited

OTHER PUBLICATIONS

Perez-Gracia, J.L., et al., "Orchestrating immune check-point blockade for cancer immunotherapy in combinations," Current Opinion in Immunology, 27: 89-97 (2014).
Ribas, A., et al., "Antitumor Activity in Melanoma and Anti-Self Responses ina Phase I Trial With the Anti-Cytotoxic T Lymphocyte-Associated Antigen 4 Monoclonal Antibody CP-675,206," Journal of Clinical Oncology, 23(35): 8968-8977 (2005).
Soria, J.C., "Clinical Activity, Safety and Biomarkers of PD-L1 Blockade in Non-Small Cell Lung Cancer (NSCLC): Additional Analysis from a Clinical Study of the Engineered Antibody MPDL3280A (Anti-PDL1)," Proceedings of the European Cancer Conference (ECC '13), abstract 3408 (2013).
U.S., NIH, "A Phase ½ Study to Evaluate MEDI4736," https://clinicaltrials.gov/ct2/show/NCT01693562 (2014).
Zatloukal, P., et al.. Randomized phase II clinical trial comparing tremelimumab (CP-675,206) with best supportive care (BSC) following first-line platinum-based therapy in patients (pts) with advanced non-small cell lung cancer (NSCLC), Journal of Clinical Oncology, 27: abstract 8071 (2009).
European Search Report dated Jan. 28, 2016, in connection with corresponding European Application No. GB1508097.1.
International Search Report dated Jul. 31, 2015, in connection with corresponding International Application No. PCT/EP2015/060523.
www.merriam-webster.com/dictionary/coadministration [12/13/2017 5:46:38 PM] (pp. 1-8).
Ecog-acrin.org/resources/ecog-performance-status[Dec. 13, 2017 6:07:29 PM] (pp. 1-3).
Antonia et al. (Lancet Oncol 2016; 17:299-308).
Aranda (2014) OncoImmunology, 3:2, e27297.
Callahan, M.K., et al., "At the Bedside: CTLA-4- and PD-I-blocking antibodies in cancer immunotherapy," Journal of Leukocyte Biology, 94(1): 41-53 (2013).
Cho, D., et al., "Clinical activity, safety, and biomarkers of MPDL3280A, an engineered PD-LI antibody in patients with netastatic renal cell carcinoma (mRCC)," Journal of Clinical Oncology, 31(15): (2013).
Horn, L., et al., "An analysis of the relationship of clinical activity to baseline EGFR status, PDLI expression and prior treatment history in patients with non-small cell lung cancer (NSCLC) following PD-LI blockade with MPDL3280A (anti-PDLI)," Journal of Thoracic Oncology, 8(2): S364.
Kyi, C., et al., "Checkpoint blocking antibodies in cancer immunotherapy," FEES Letters, 588(2): 368-376 (2013).
Massarelli, (2014) "Immunotherapy in lung cancer" Trends Lung Cancer Res, 3(1):53-63.
Medimmune: "A Phase Ib Study of MEDI4736 in Combination With Tremelimumab in Subjects With Advanced Non-small Cell Lung Cancer," ClinicalTrials.gov (2013).
Soria, J.C., "Clinical Activity, Safety and Biomarkers of PD-LI Blockade in Non-Small Cell Lung Cancer (NSCLC): Additional Analysis from a Clinical Study of the Engineered Antibody MPDL3280A (Anti-PDLI)," Proceedings of the European Cancer Conference (ECC '13), abstract 3408 (2013).
U.S., NIH, "A Phase V2 Study to Evaluate MEDI4736," (2014).
www.merriam-webster.com/dictionary/coadministration [Dec. 13, 2017 5:46:38 PM] (pp. 1-8).
The American Journal of Managed Care, vol. 20, Special No. 5, COV1, SP155-SP156 (2013).
AstraZeneca, "A Phase III, Randomised, Double-blind, Placebo-controlled, Multi-centre, International Study of MEDI4736 as Sequential Therapy in Patients withLocally Advanced, Unresectable Non-Small Cell Lung Cancer (Stage III)Who Have Not Progressed Following Definitive, Platinum-based,Concurrent Chemoradiation Therapy (PACIFIC) International," Feb. 2014.
Duraiswamy, et al. 2013 "Dual blockade of PD-1 and CTLA-4 combined with tumor vaccine effectively restores t-cell rejection function in tumors," Cancer Research, 73(12):3591-603.
Tarhini, et al., 2013. "Tremelimumab: a review of development to date in solid tumors," Immunotherapy, 5(3): 215-229.
Tarhini (2007) "Tremelimumab, a fully human monoclonal IgG2 antibody against CTLA4 for the potential treatment of cancer" Curr Opin Mol Ther, 9(5): 505-14.
ClinicalTrials.gov Archive NCT03130764 [online], Apr. 26, 2017, [search on Feb. 16, 2022], https://clinicaltrials.gov/ct2/show/NCT03130764.
ClinicalTrials.gov Archive NCT03975114 [online], Jun. 5, 2019, [search on Feb. 16, 2022], https://clinicaltrials.gov/ct2/show/NCT03975114.
Narwal et al., "Population Pharmacokinetics of Sifalimumab, an Investigational Anti-lnterferon-a Monoclonal Antibody, in Systemic Lupus Erythematosus," Clin. Phamnacokinet. 52(11): 1017-27 (2013).
Ng et al., "Rationale for Fixed Dosing of Pertuzumab in Cancer Patients Based on Population Pharmacokinetic Analysis," Pharm. Res. 23(6): 1275-84 (2006).
Wang et al., "Fixed Dosing Versus Body Size-Based Dosing of Monoclonal Antibodies in Adult Clinical Trials," J. Clin. Pharmacol. 49(9): 1012-24 (2009).
Zhang et al., "Fixed dosing versus body size-based dosing of therapeutic peptides and proteins in adults," J. Clin. Pharmacol. 52(1): 18-28 (2012).

\* cited by examiner

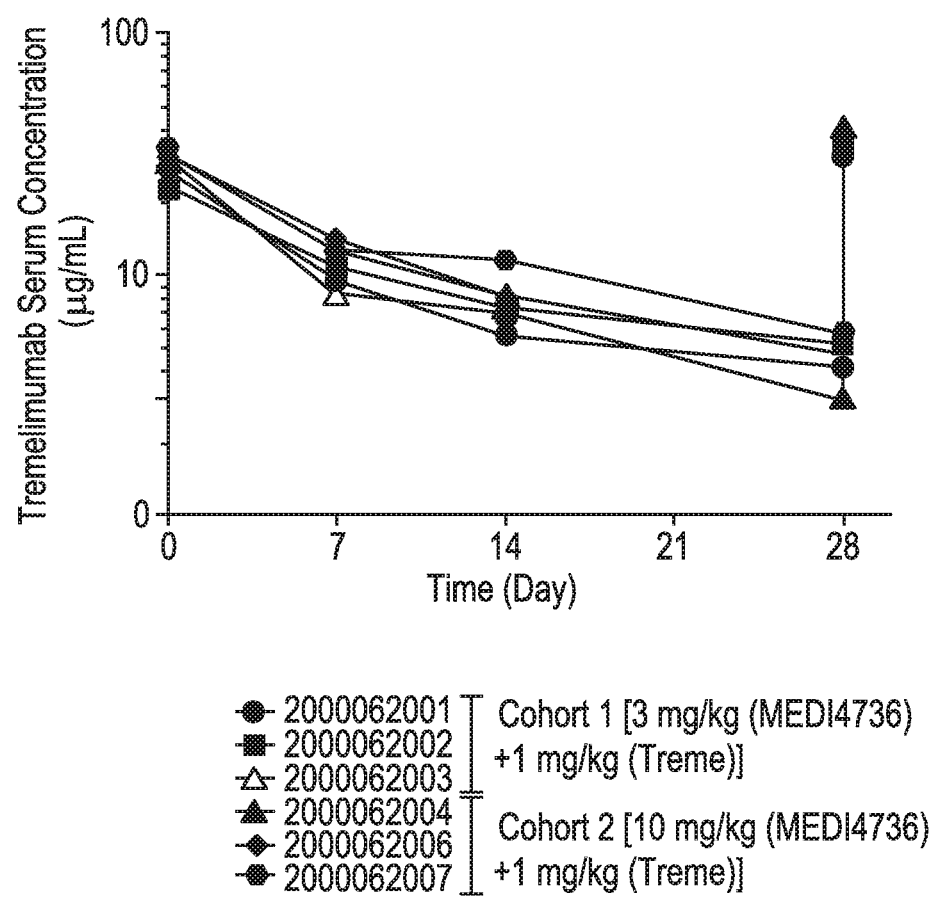

FIG. 10A

| Severity | irAEs [a] | All Other Events |
|---|---|---|
| Grade 1 | None | <ins>For infusion-related reactions:</ins><br>• The infusion rate of MEDI4736 or tremelimumab may be decreased by 50% or temporarily interrupted until resolution of the event<br>• Acetaminophen and/or antihistamines may be administered per institutional standard at the discretion of the investigator<br>• Consider premedication prior to subsequent doses<br>• For all other AEs: no dose adjustment is required |
| Grade 2 | <ins>For endocrinopathy</ins><br>• Hold MEDI4736 and tremelimumab<br>• When endocrinopathy is controlled, resume MEDI4736 and tremelimumab<br><br>    For dermatologic irAEs<br>    Do not hold MEDI4736 and tremelimumab dose<br>    For pneumonitis<br>• Hold MEDI4736 and tremelimumab until resolution to ≤ Grade 1<br>If resolution to ≤ Grade 1 occurs within 3 days of the initiation of maximal supportive care (including corticosteroids), resume MEDI4736 and tremelimumab administration at next scheduled dose. Otherwise, discontinue MEDI4736 and tremelimumab<br><br><ins>For all irAEs</ins><br>• Hold MEDI4736 and tremelimumab until resolution to ≤ Grade 1<br>• If resolution to ≤ Grade 1 does not occur within 30 days, discontinue MEDI4736 and tremelimumab | <ins>For infusion-related reactions:</ins><br>• The infusion rate of MEDI4736 or tremelimumab may be decreased by 50% or temporarily interrupted until resolution of the event<br>• Acetaminophen and/or antihistamines may be administered per institutional standard at the discretion of the investigator<br>• Consider premedication prior to subsequent doses<br><br>    All Other AEs<br>• Hold MEDI4736 and tremelimumab until resolution to ≤ Grade 1 or baseline<br>If resolution to ≤ Grade 1 does not occur within 30 days, discontinue MEDI4736 and tremelimumab |

AE = adverse event; irAE = immune-related adverse event; ULN = upper limit of normal. [a] Management of irAEs may require administration of immunosuppressive medications (and/or hormone replacement therapy for endocrinopathies). Resolution of irAEs managed in this manner in the timeframes specified is acceptable.

FIG. 10B

| Severity | irAEs [a] | All Other Events |
|---|---|---|
| Grade 3 | For endocrinopathy<br>• Hold MEDI4736 and tremelimumab<br>• When endocrinopathy is controlled, resume MEDI4736 and tremelimumab administration at next scheduled dose<br><br>For dermatologic irAEs<br>• Hold MEDI4736 and tremelimumab until resolution to ≤ Grade 1 or baseline<br>• If resolution to ≤ Grade 1 or baseline does not occur within 30 days, discontinue MEDI4736 and tremelimumab<br><br>For elevations in transaminases<br>• For elevations in transaminases ≤ 8 × ULN, hold MEDI4736 and tremelimumab until resolution to ≤ Grade 1 or baseline. If elevations downgrade to ≤ Grade 2 within 7 days or resolve to ≤ Grade 1 or baseline within 14 days, resume MEDI4736 and tremelimumab administration at next scheduled dose. Otherwise, discontinue MEDI4736 and tremelimumab<br>• For elevations in transaminases > 8 × ULN, discontinue MEDI4736 and tremelimumab<br><br>For elevations in total bilirubin<br>• For elevations in total bilirubin ≤ 5 × ULN, hold MEDI4736 and tremelimumab until resolution to ≤ Grade 1 or baseline. If elevations downgrade to ≤ Grade 2 (< 3 × ULN) within 7 days or resolve to ≤ Grade 1 or baseline within 14 days, resume MEDI4736 and tremelimumab administration at next scheduled dose. Otherwise, discontinue MEDI4736 and tremelimumab<br>• For elevations in total bilirubin > 5 × ULN, discontinue MEDI4736 and tremelimumab<br><br>For all other irAEs:<br>Discontinue MEDI4736 and tremelimumab | For hypersensitivity, and infusion- related reactions:<br>• Discontinue MEDI4736 and tremelimumab<br><br>For all other AEs:<br>• Hold MEDI4736 and tremelimumab until resolution to ≤ Grade 1 or baseline<br>• For AEs that downgrade to ≤ Grade 2 within 7 days or resolve to ≤ Grade 1 or baseline within 14 days, resume MEDI4736 and tremelimumab administration at next scheduled dose. Otherwise, discontinue MEDI4736 and tremelimumab |
| Grade 4 | Discontinue MEDI4736 and tremelimumab | Discontinue MEDI4736 and tremelimumab |

AE = adverse event; irAE = immune-related adverse event; ULN = upper limit of normal. [a] Management of irAEs may require administration of immunosuppressive medications (and/or hormone replacement therapy for endocrinopathies). Resolution of irAEs managed in this manner in the timeframes specified is acceptable.

FIG. 11

| Cohort | MEDI4736 x 12 doses | Tremelimumab Q4W X6 doses and Q12W x 3 doses |
|---|---|---|
| 1a | 3 | 1 |
| 2a | 10 | 1 |
| 3a | 15 | 1 |
| 3b | 10 | 3 |
| 4a | 15 | 3 |
| 5 | 15 | 10 |

| | Key Study Criteria |
|---|---|
| Key Eligibility | Escalation<br>1. Locally Advanced Unresectable or Metastatic NSCLCa Relapsed/Refractory<br>2. Immunotherapy Naive<br>Expansion<br>1. Locally Advanced Unresectable or Metastatic NSCLCa Relapsed/Refractory<br>2. Immunotherapy Naive and Pre-Treated Cohorts |
| Objective | 1. Primary: MTD or highest protocol-defined dose for each agent in the absence of exceeding the MTD and the safety profile<br>2. Secondary: Antitumor activity, Immunogenecity, PK/PD |
| Safety Assesssments | 1. Cycle 1: Weekly for 4 weeks<br>2. Cycle 2-6: Every 1-2 weeks<br>3. Cycle 7-12: Every 1 week |
| Response Criteria | 1. Primary response criteria every 8 weeks using RECIST 1.1 with modifications |

FIG. 12

| | MEDI4736 (M) and Tremelimumab (T) in NSCLCa Q4W<br>April 23, 2014 cut-off | | | | | |
|---|---|---|---|---|---|---|
| | Cohort | | | | | |
| | 1a | 2a | 3a | 3b | 4a | |
| | 3 mg/kg (M)<br>1 mg/kg (T)<br>Q4W | 10 mg/kg (M)<br>1 mg/kg (T)<br>Q4W | 15 mg/kg (M)<br>1 mg/kg (T)<br>Q4W | 10 mg/kg (M)<br>3 mg/kg (T)<br>Q4W | 15 mg/kg (M)<br>3 mg/kg (T)<br>Q4W | |
| Subjects enrolled | 3 | 3 | 3 | 3 | Week of 28th | |
| No. of Lines | 1,2,3 | 4,3,3 | 4,5,3 | 2,1,3 | | |
| Tumor | 1-Sq, 2-Non-sq,<br>1-KRAS | 3-Non-sq | 1-Sq, 2-Non-sq,<br>1-EGFR (T790) | 3-Non-sq | | |
| Subjects on treatment | 0 | 2 | 3 | 2 | | |
| Cohort fully enrolled | 07Nov13 | 17Jan14 | 14Feb14 | 26Feb14 | | |
| DLT Period (days) | 56 | 28 | 28 (protocol)<br>56 (extended due to one AE in prior cohort) | 28 (protocol)<br>56 (extended due to one AE in prior cohort) | 28 days | |
| Next Cohort Planned Enrollment | | | Week of 4/28 | Week of 4/28 | | |

Q4W = every 4 weeks

FIG. 13

Related AE's
MEDI4736 (M) and Tremelimumab (T) Q4W
April 23, 2014 cut-off

| | Cohort | | | | |
|---|---|---|---|---|---|
| | 1a<br>3 mg/kg (M)<br>1 mg/kg (T)<br>N=3 | 2a<br>10 mg/kg (M)<br>1 mg/kg (T)<br>N=3 | 3a<br>15 mg/kg (M)<br>1 mg/kg (T)<br>N=3 | 3b<br>10 mg/kg (M)<br>3 mg/kg (T)<br>N=3 | 4a<br>15 mg/kg (M)<br>3 mg/kg (T)<br>N=3<br>(started week 28th) |
| Any AE (N) | 3 | 3 | 3 | 2 | |
| Any G3/G4 AE | 0 | 1* | 1 | 1 | |
| SAE | 1 | 1* | 1 | 1 | |
| AE to D/C | 1 | 1 | 0 | 1 | |
| Related AE | 1 | 2 | 3 | 1 | |
| Related G3/G4 | 0 | 1* | 1 | 1 | |
| G5 | 0 | 1* | 0 | 0 | |
| Related AE to D/C | 0 | 1* | 0 | 1 | |

Tumor Size Change from Baseline
(First Four Cohorts)

FIG. 16

Individual sPD-L1 Profiles in Combination

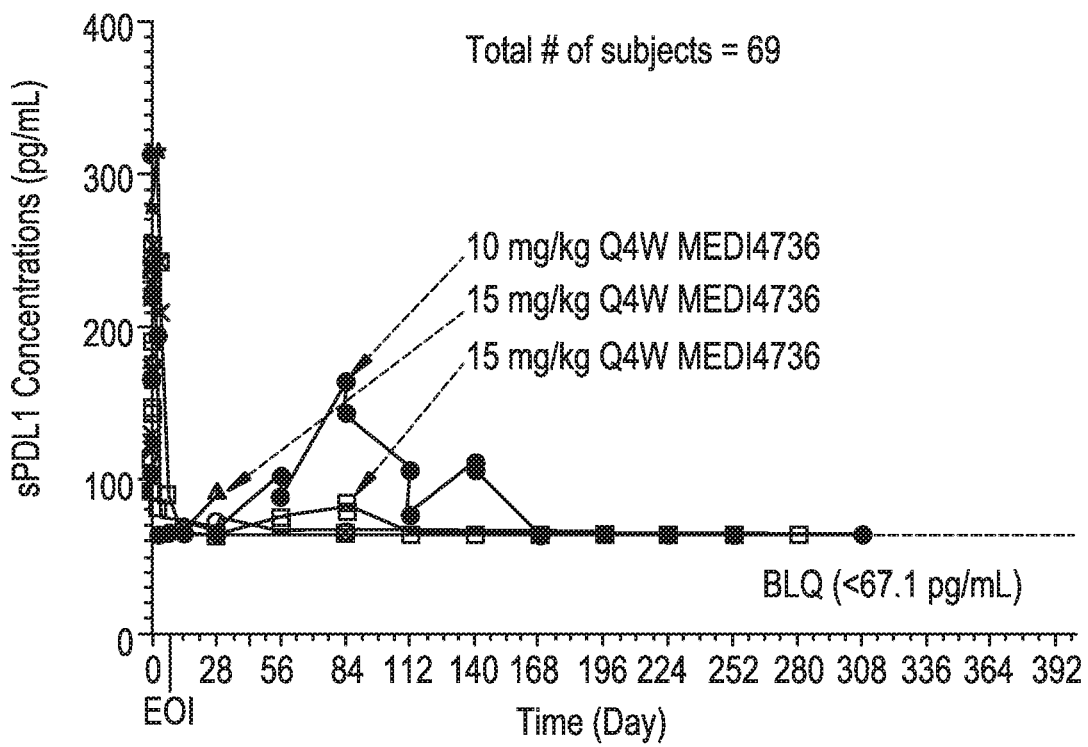

- Complete sPD-L1 suppression at doses ≥ 15 mg/kg Q4W MEDI4736
  - 1 subject each at 10 mg/kg Q4W and 15 mg/kg Q4W showed partial sPD-L1 suppression at some visits followed by complete suppression after repeated dosing
    - 1 subject following 15 mg/kg Q4W was not suppressed at Day 29 (limited data available)
  - Complete suppression observed with single-agent MEDI4736 (Study 1108) at doses > 3 mg/kg Q2W

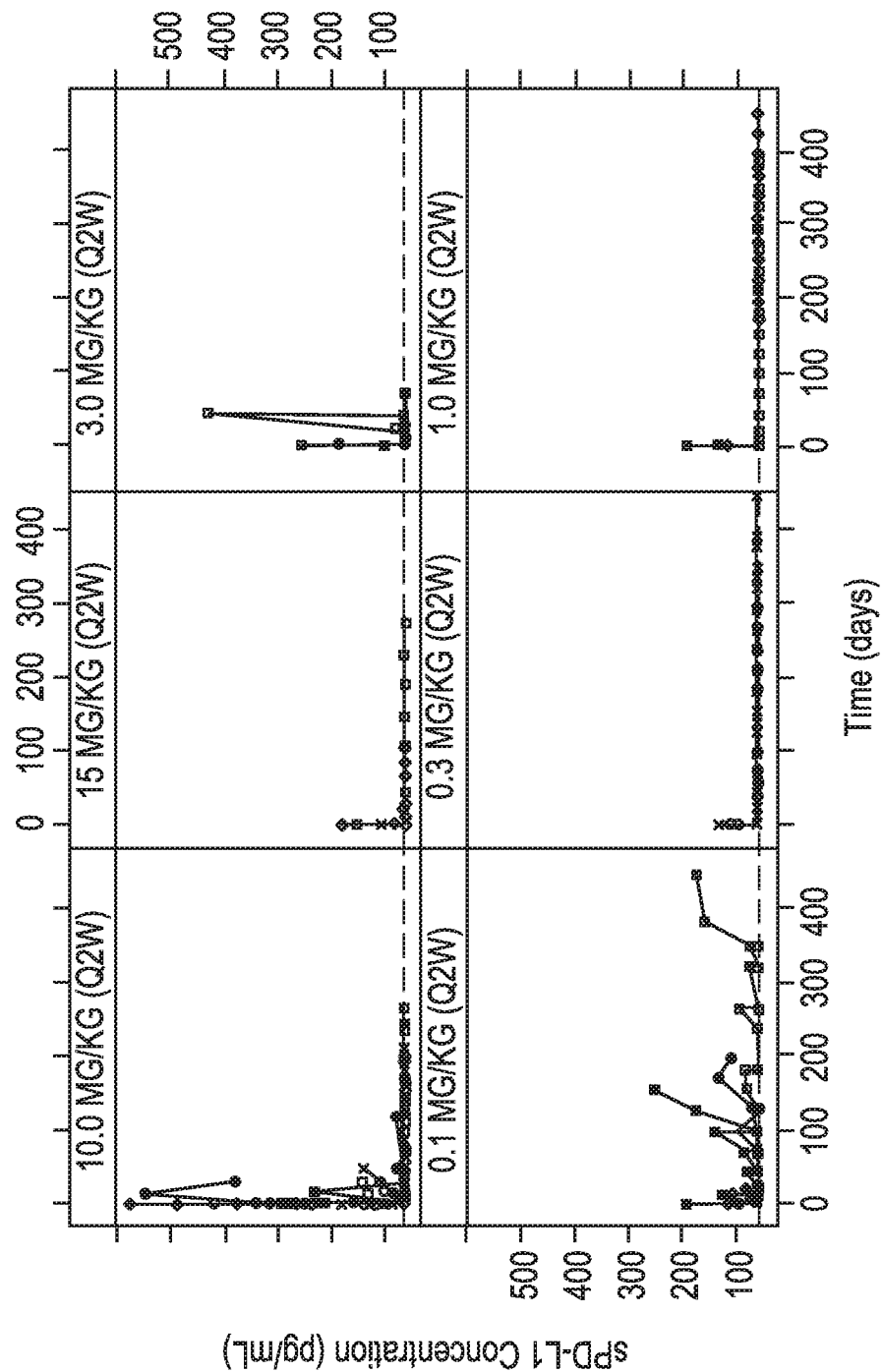

- Monotonic increase in peak CD4+Ki67+ cells with increasing treme dose
- Increase greater than observed with MEDI4736 alone
- CD8+ proliferative response is greater with combinations than that observed with MEDI4736 alone SEM only provided for time points with n ≥ 3

○ Minimal change was observed with MEDI4736 alone
○ All tested combination doses have a pattern distinguishable from MEDI4736
○ Maximal increase observed with 10mg Treme SEM only provided for time points with n≥3

CD4+T effector cells: All MEDI4736 doses combined

CD4_T effector memory

- CP1108 MEDI4736
- MEDI4736, Treme 1 mg/kg
- MEDI4736, Treme 3 mg/kg
- MEDI4736, Treme 10 mg/kg ○ Increase in CD4+ effector memory cells is greater with combination doses than that observed with MEDI4736 alone SEM only provided for time points with $n \geq 3$

FIG. 22

Clinical Activity: COMBINATION VS MEDI4736 MONOTHERAPY

| | MEDI4736/Treme Combo (All Doses) | | MEDI4736 10 mg/kg Q2W CP1108 (NSCLC) | |
|---|---|---|---|---|
| | ORR n/N, % (95%CI) | SD n/N, % (95%CI) | ORR n/N, % (95%CI) | SD n/N, % (95%CI) |
| Response Evaluable | 12/53 23% (12.3, 36.2) | 14/53 26% (15.3, 40.3) | 25/166 15% (10.0, 21.4) | 41/166 25% (18.3, 32.0) |
| PD-L1+ | 4/11 36% (10.9, 69.2) | 3/11 27% (6.0, 61.0) | 14/56 25% (14.4, 38.4) | 10/56 18% (8.9, 30.4) |
| PD-L1- | 6/24 25% (9.8, 46.7) | 7/24 29% (12.6, 51.1) | 6/83 7% (2.7, 15.1) | 28/83 34% (23.7, 44.9) |
| PD-L1 Unknown | 2/18 11% (1.4, 34.7) | 4/18 22% (6.4, 47.6) | 5/27 19% (6.3, 38.1) | 3/27 11% (2.4, 29.2) |

- Data as of Jan 27, 2015 for MEDI4736/Treme combo. Data as of Oct 31, 2014 for MEDI4736 NSCL(CP1108).
- Response Evaluable: treated patients with measurable disease at baseline + ≥1 follow-up scan (includes discontinuations due to disease progression or death prior to first follow-up scan). For MEDI4736 NSCLC (CP1108), only patients with >=12 weeks follow-up were included.
- ORR includes confirmed and unconfirmed CR or PR. For MEDI4736 NSCLC (CP1108), BOR of SD with minimum duration of 12 weeks. For MEDI4736/Treme combo, BOR of SD with minimum duration of 7 weeks

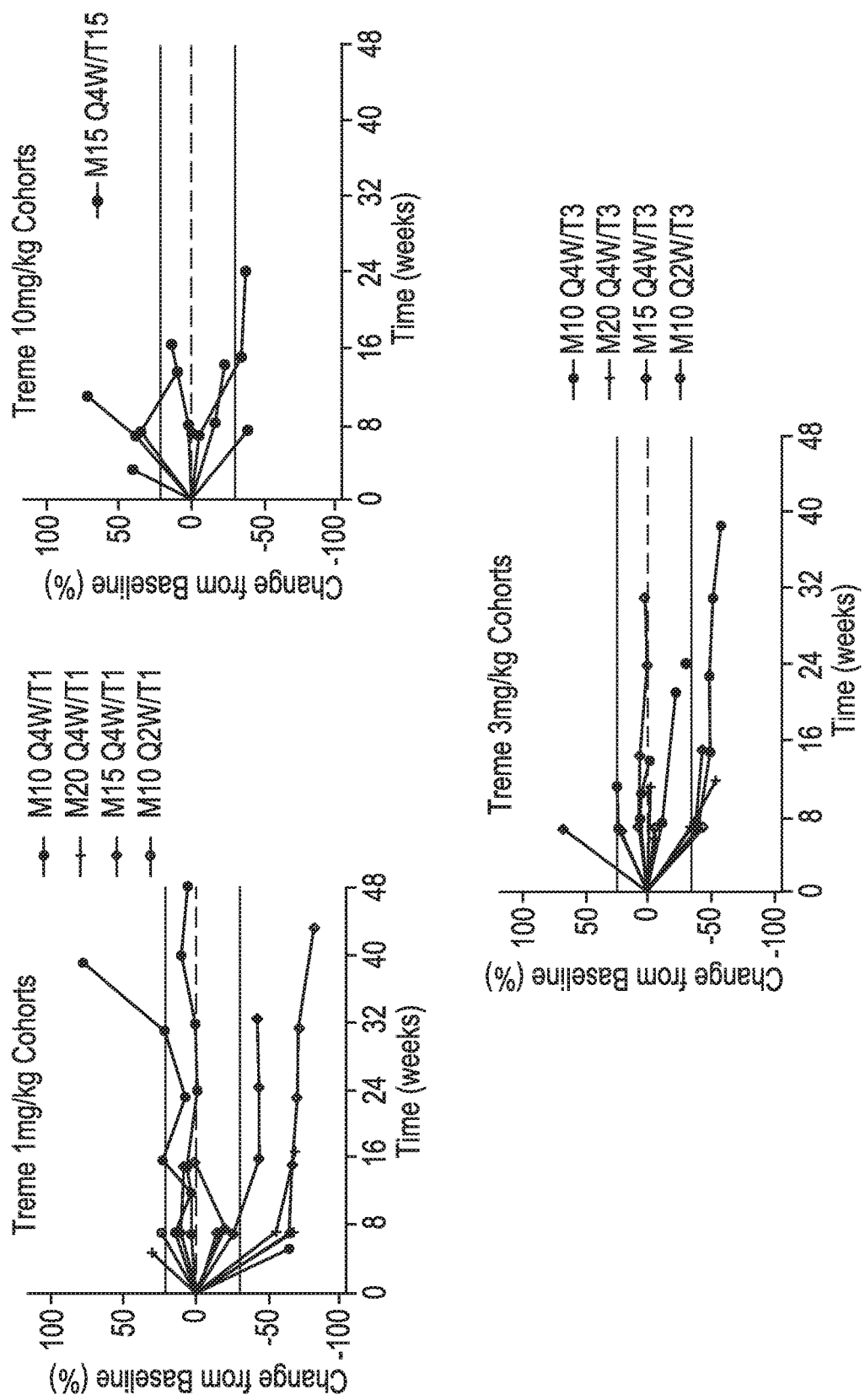

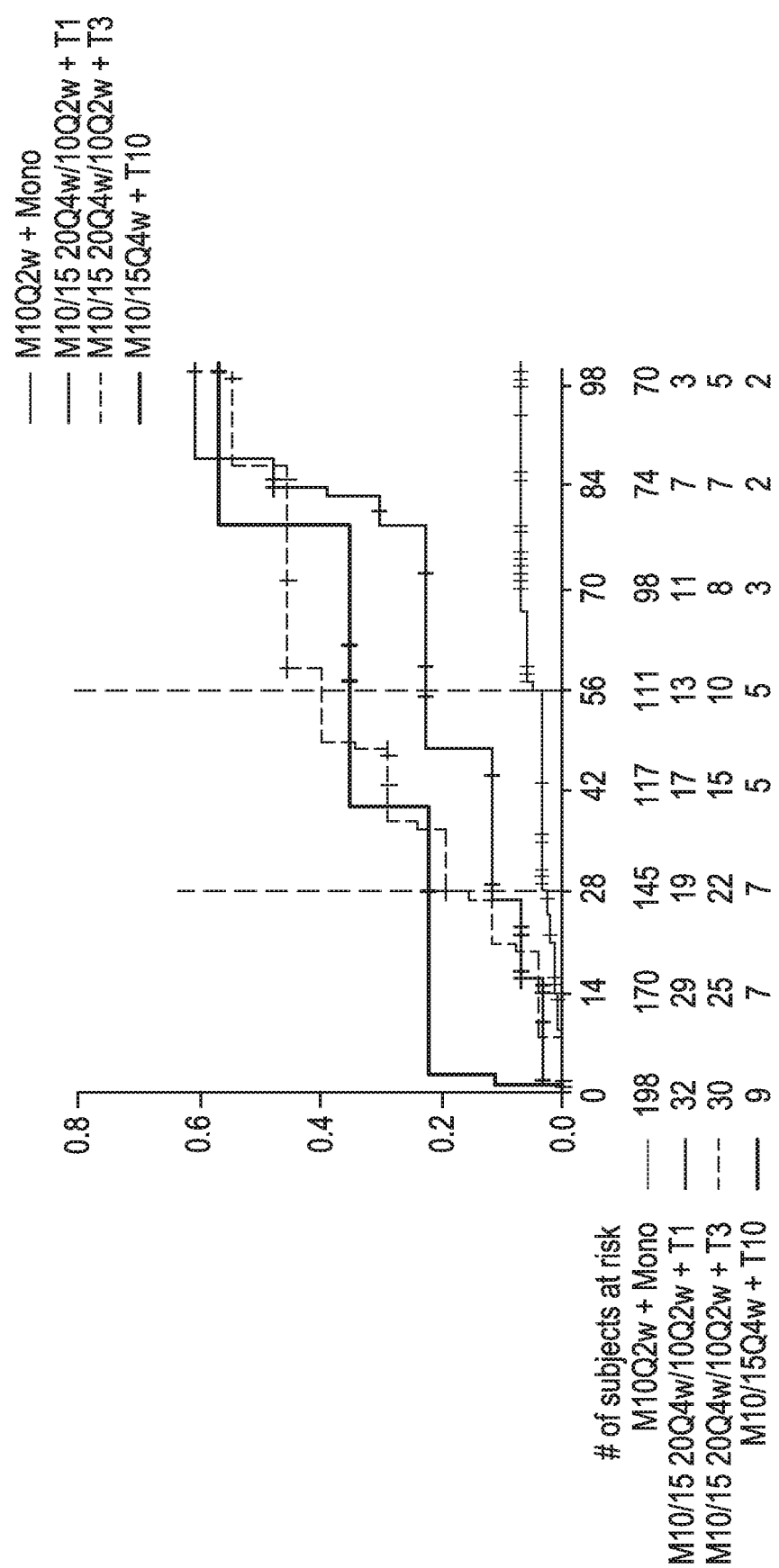

Safety Summary: Time of Onset of Related >=Gr3 AE's in Selected Combination Cohorts vs. Monotherapy MEDI4736

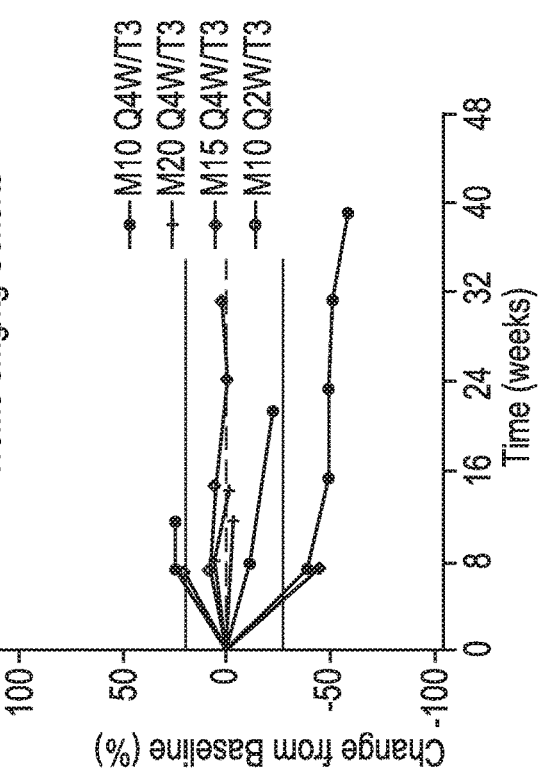
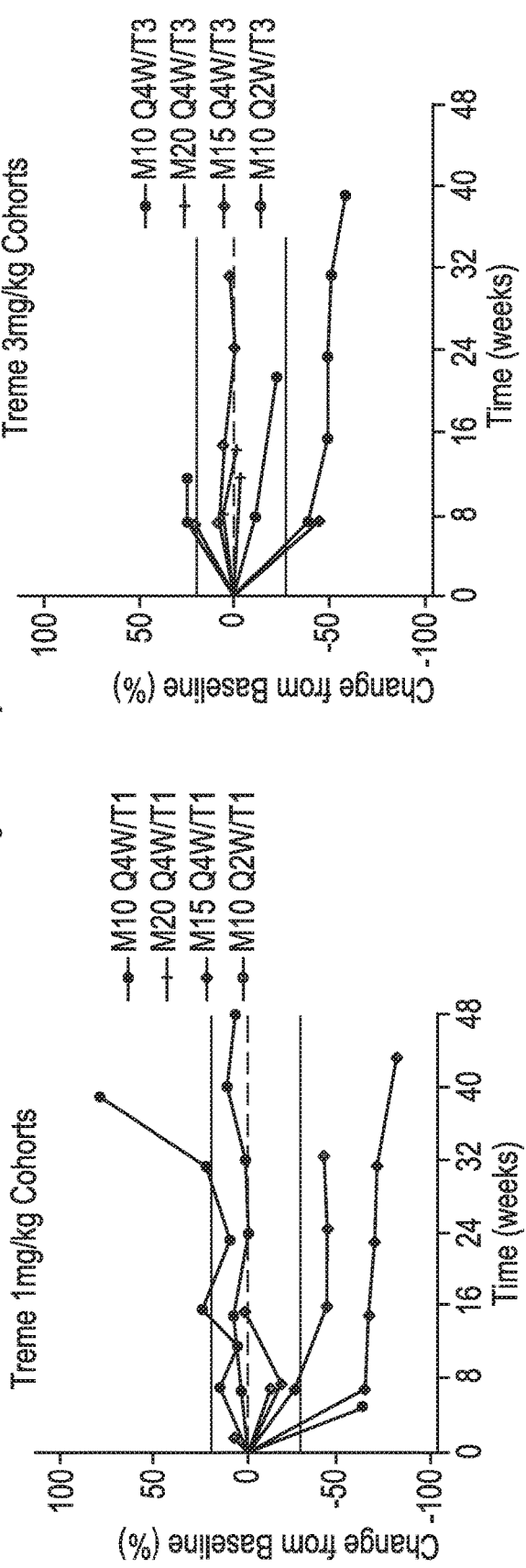
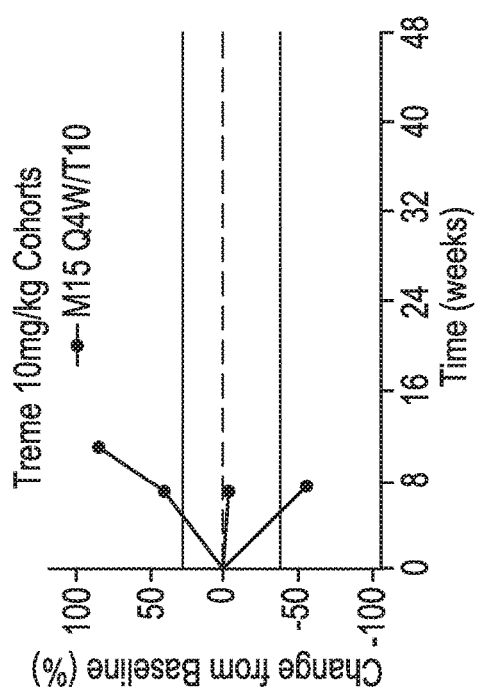
FIG. 32

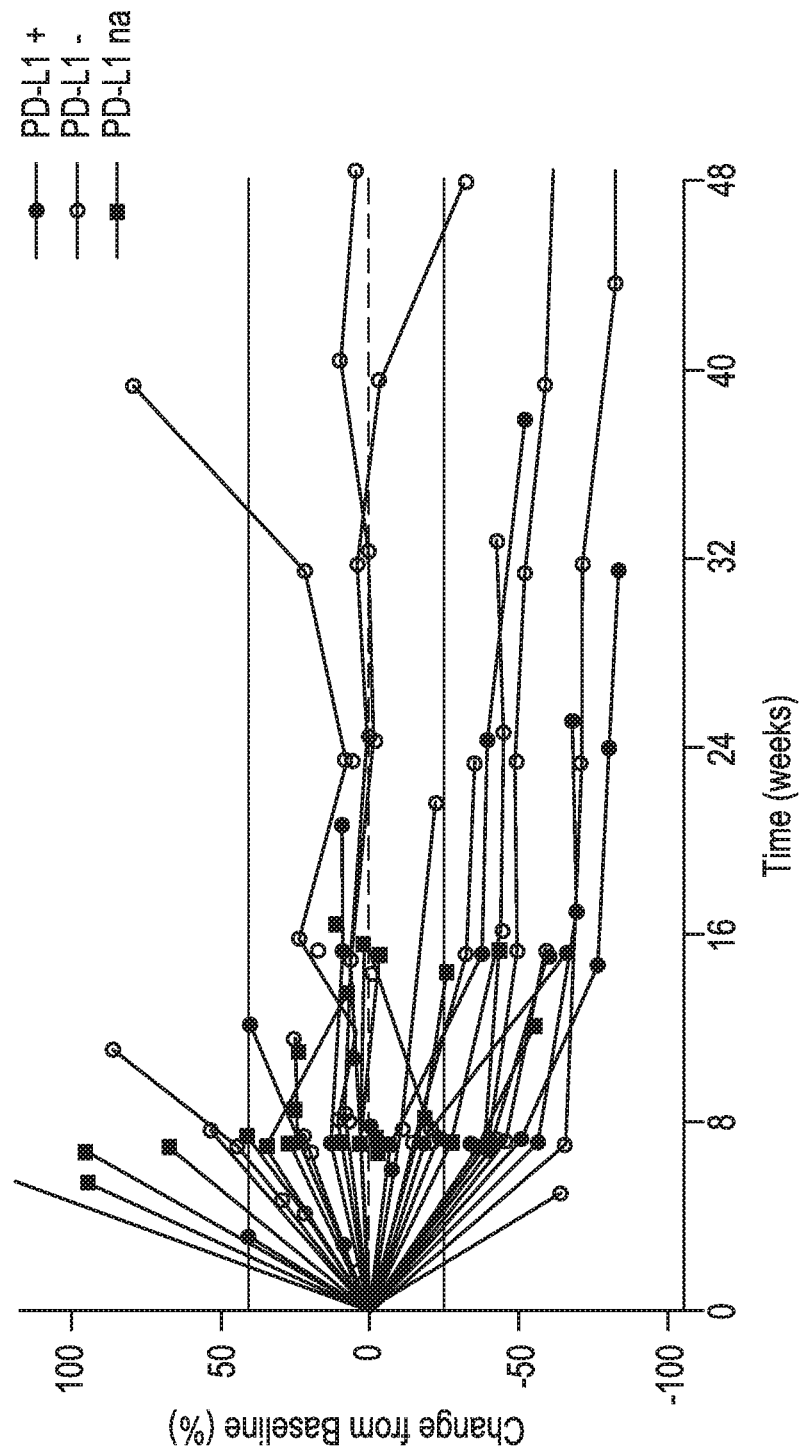

Tumor Size Change from Baseline - PD-L1 Negative Subjects

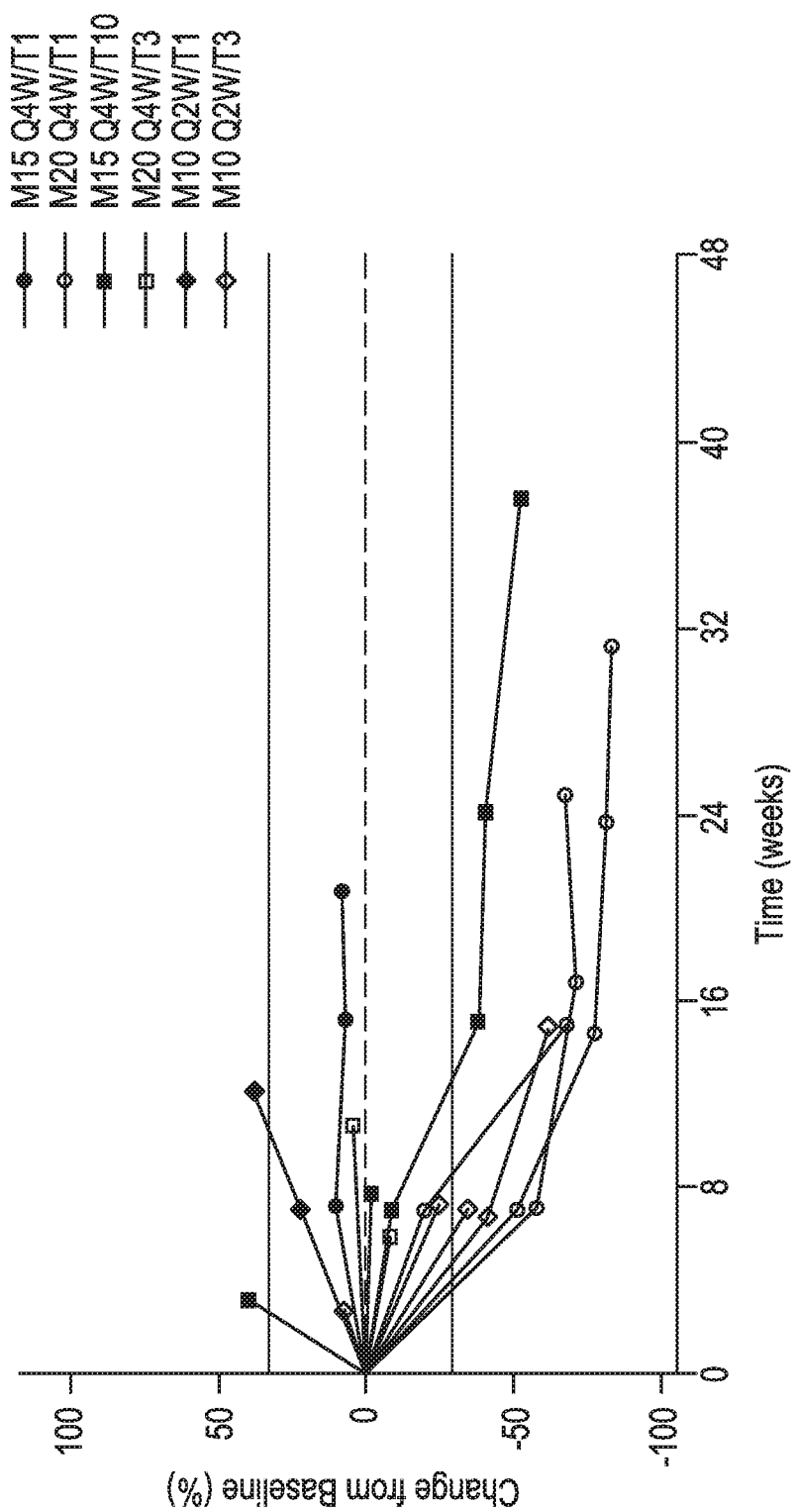

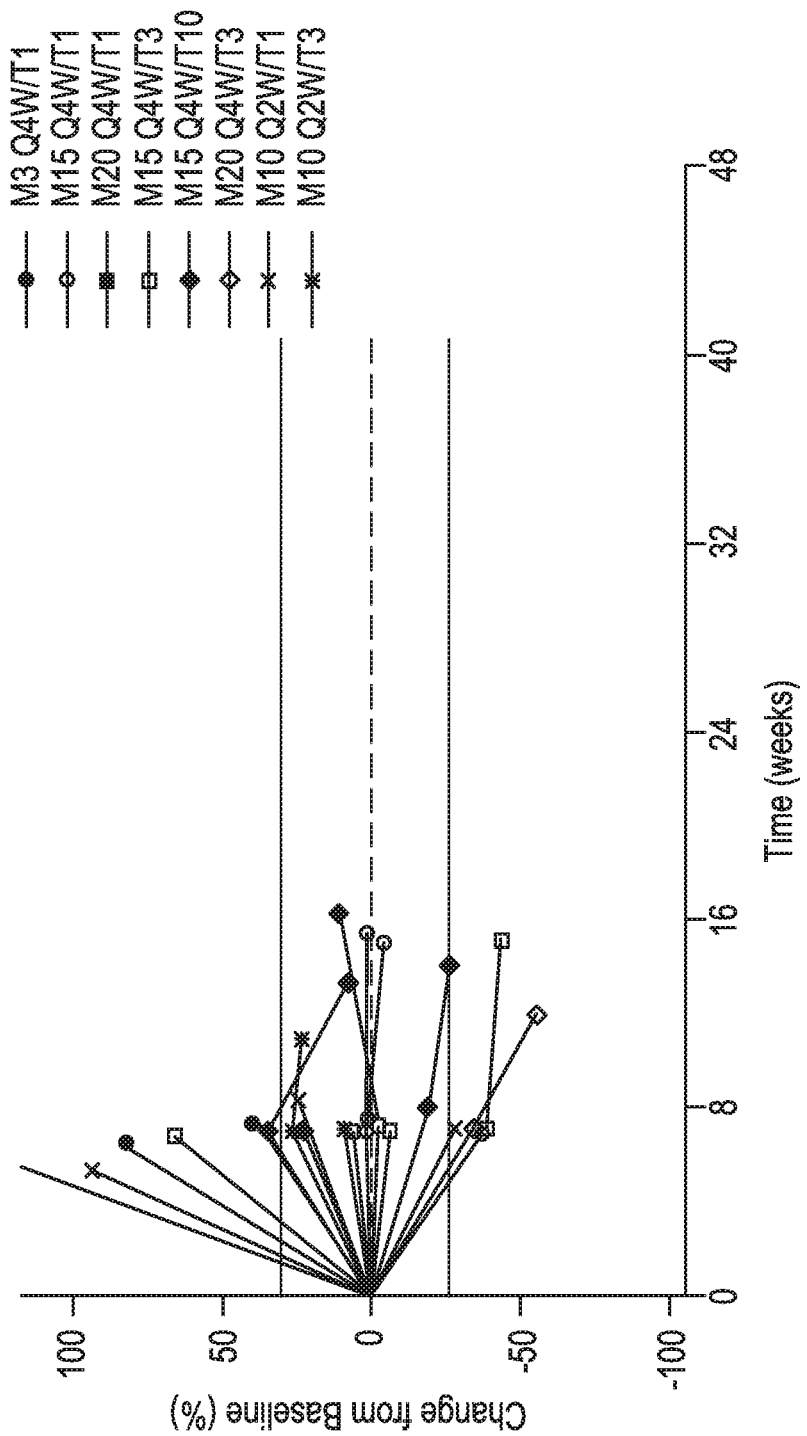

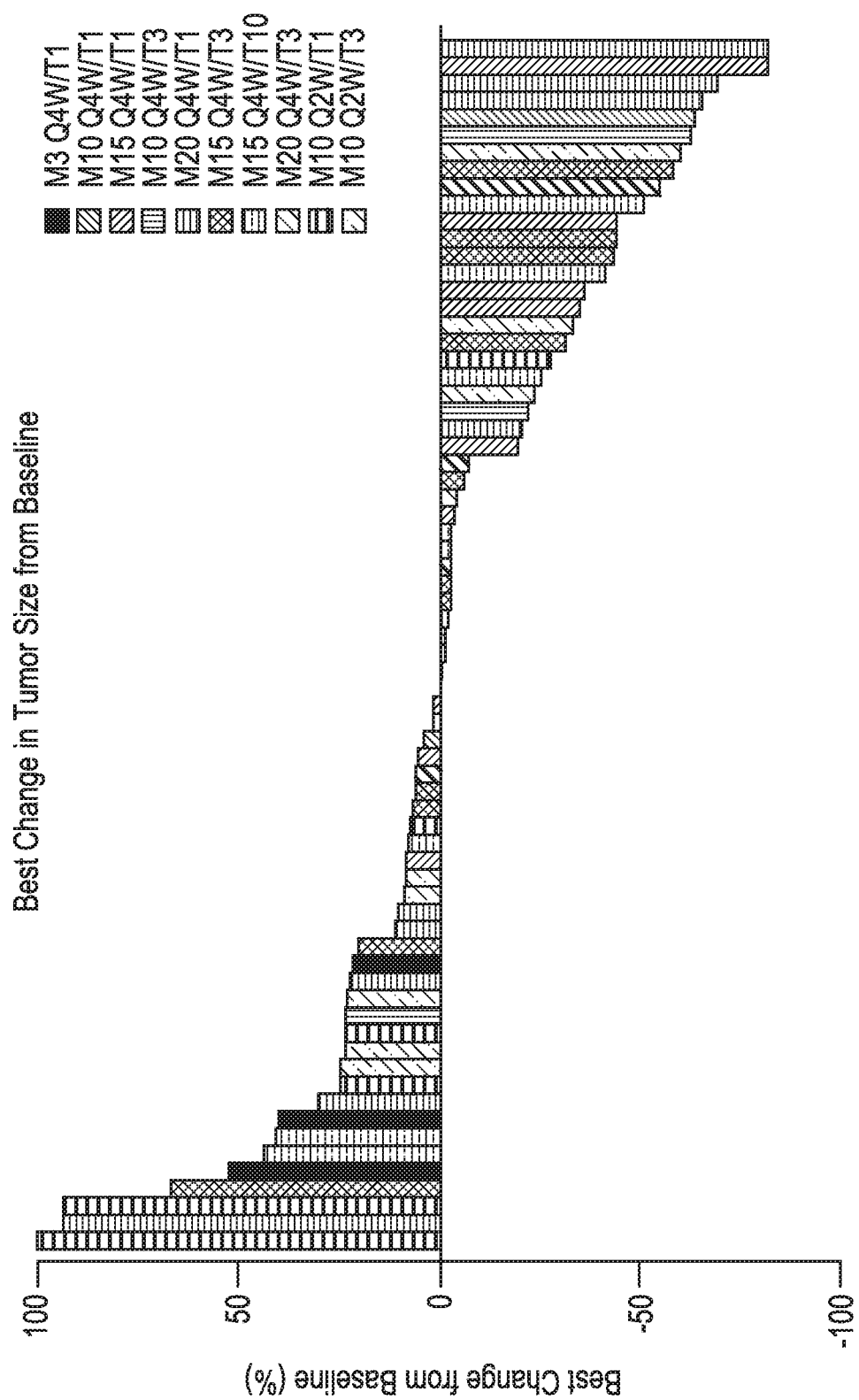

SEQUENCE LISTING

<160> NUMBER OF SEQ ID NOS: 16

<210> SEQ ID NO 1
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

```
Arg Tyr Trp Met Ser
1               5

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Ile Lys Gln Asp Gly Ser Glu Lys Tyr Tyr Val Asp Ser Val Lys
1               5                   10                  15

Gly

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Gly Gly Trp Phe Gly Glu Leu Ala Phe Asp Tyr
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Gln Arg Val Ser Ser Ser Tyr Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Ala Ser Ser Arg Ala Thr
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Tyr Gly Ser Leu Pro Trp Thr
1               5

<210> SEQ ID NO 9
<211> LENGTH: 139
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Pro Ser Ser Leu Ser Ala Ser Val Gly Asp Arg Val Thr Ile Thr Cys
1               5                   10                  15

Arg Ala Ser Gln Ser Ile Asn Ser Tyr Leu Asp Trp Tyr Gln Gln Lys
            20                  25                  30

Pro Gly Lys Ala Pro Lys Leu Leu Ile Tyr Ala Ala Ser Ser Leu Gln
        35                  40                  45

Ser Gly Val Pro Ser Arg Phe Ser Gly Ser Gly Ser Gly Thr Asp Phe
    50                  55                  60

Thr Leu Thr Ile Ser Ser Leu Gln Pro Glu Asp Phe Ala Thr Tyr Tyr
65                  70                  75                  80

Cys Gln Gln Tyr Tyr Ser Thr Pro Phe Thr Phe Gly Pro Gly Thr Lys
                85                  90                  95

Val Glu Ile Lys Arg Thr Val Ala Ala Pro Ser Val Phe Ile Phe Pro
            100                 105                 110

Pro Ser Asp Glu Gln Leu Lys Ser Gly Thr Ala Ser Val Val Cys Leu
        115                 120                 125

Leu Asn Asn Phe Tyr Pro Arg Glu Ala Lys Val
    130                 135

<210> SEQ ID NO 10
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Val Val Gln Pro Gly Arg Ser Leu Arg Leu Ser Cys Ala Ala Ser
1               5                   10                  15

Gly Phe Thr Phe Ser Ser Tyr Gly Met His Trp Val Arg Gln Ala Pro
            20                  25                  30

Gly Lys Gly Leu Glu Trp Val Ala Val Ile Trp Tyr Asp Gly Ser Asn
        35                  40                  45

Lys Tyr Tyr Ala Asp Ser Val Lys Gly Arg Phe Thr Ile Ser Arg Asp
    50                  55                  60

Asn Ser Lys Asn Thr Leu Tyr Leu Gln Met Asn Ser Leu Arg Ala Glu
65                  70                  75                  80

Asp Thr Ala Val Tyr Tyr Cys Ala Arg Asp Pro Arg Gly Ala Thr Leu
                85                  90                  95

Tyr Tyr Tyr Tyr Tyr Gly Met Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His
                165
```

```
<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Phe Thr Phe Ser Ser Tyr Gly Met His
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Ile Trp Tyr Asp Gly Ser Asn Lys Tyr Tyr Ala Asp Ser Val
1               5                   10                  15

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Ala Val Tyr Tyr Cys Ala Arg Asp Pro Arg Gly Ala Thr Leu Tyr
1               5                   10                  15

Tyr Tyr Tyr Tyr Gly Met Asp Val
            20

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ala Ser Gln Ser Ile Asn Ser Tyr Leu Asp
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ala Ser Ser Leu Gln Ser
1               5

<210> SEQ ID NO 16
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 16

Gln Gln Tyr Tyr Ser Thr Pro Phe Thr
1               5
```

ANTI-B7-H1 AND ANTI-CTLA-4 ANTIBODIES FOR TREATING NON-SMALL CELL LUNG CANCER

CROSS-REFERENCE TO RELATED APPLICATION

This application is a continuation of U.S. application Ser. No. 14/710,101 filed on May 12, 2015, said application Ser. No. 14/710,101 claims benefit under 35 U.S.C. § 119(e) of the following U.S. Provisional Application No. 61/992,658, filed May 13, 2014, U.S. Provisional Patent Application Ser. No. 62/105,992, filed Jan. 21, 2015, and U.S. Provisional Patent Application Ser. No. 62/114,336, filed Feb. 10, 2015. Each of the above listed applications is incorporated by reference herein in its entirety for all purposes.

REFERENCE TO THE SEQUENCE LISTING

This application incorporates by reference a Sequence Listing submitted with this application as text file entitled TRB7-100US1_SL.txt created on May 12, 2015 and having a size of 8,564 kilobytes.

BACKGROUND

Cancer continues to be a major global health burden. Despite progress in the treatment of cancer, there continues to be an unmet medical need for more effective and less toxic therapies, especially for those patients with advanced disease or cancers that are resistant to existing therapeutics.

The role of the immune system, in particular T cell-mediated cytotoxicity, in tumor control is well recognized. There is mounting evidence that T cells control tumor growth and survival in cancer patients, both in early and late stages of the disease. However, tumor-specific T-cell responses are difficult to mount and sustain in cancer patients.

Two T cell pathways receiving significant attention to date signal through cytotoxic T lymphocyte antigen-4 (CTLA-4, CD152) and programmed death ligand 1 (PD-L1, also known as B7-H1 or CD274).

CTLA4 is expressed on activated T cells and serves as a co-inhibitor to keep T cell responses in check following CD28-mediated T cell activation. CTLA4 is believed to regulate the amplitude of the early activation of naïve and memory T cells following TCR engagement and to be part of a central inhibitory pathway that affects both antitumor immunity and autoimmunity. CTLA4 is expressed exclusively on T cells, and the expression of its ligands CD80 (B7.1) and CD86 (B7.2), is largely restricted to antigen-presenting cells, T cells, and other immune mediating cells. Antagonistic anti-CTLA4 antibodies that block the CTLA4 signaling pathway have been reported to enhance T cell activation. One such antibody, ipilimumab, was approved by the FDA in 2011 for the treatment of metastatic melanoma. Another anti-CTLA4 antibody, tremelimumab, was tested in phase III trials for the treatment of advanced melanoma, but did not significantly increase the overall survival of patients compared to the standard of care (temozolomide or dacarbazine) at that time.

PD-L1 is also part of a complex system of receptors and ligands that are involved in controlling T-cell activation. In normal tissue, PD-L1 is expressed on T cells, B cells, dendritic cells, macrophages, mesenchymal stem cells, bone marrow-derived mast cells, as well as various nonhematopoietic cells. Its normal function is to regulate the balance between T-cell activation and tolerance through interaction with its two receptors: programmed death 1 (also known as PD-1 or CD279) and CD80 (also known as B7-1 or B7.1). PD-L1 is also expressed by tumors and acts at multiple sites to help tumors evade detection and elimination by the host immune system. PD-L1 is expressed in a broad range of cancers with a high frequency. In some cancers, expression of PD-L1 has been associated with reduced survival and unfavorable prognosis. Antibodies that block the interaction between B7-H1 and its receptors are able to relieve PD-L1-dependent immunosuppressive effects and enhance the cytotoxic activity of antitumor T cells in vitro. MEDI4736 is a human monoclonal antibody directed against human PD-L1 that is capable of blocking the binding of PD-L1 to both the PD-1 and CD80 receptors.

Despite the significant progress made over the past decade in developing strategies for combatting cancer and other diseases, patients with advanced, refractory and metastatic disease have limited clinical options. Chemotherapy, irradiation, and high dose chemotherapy have become dose limiting. There remains a substantial unmet need for new less-toxic methods and therapeutics that have better therapeutic efficacy, longer clinical benefit, and improved safety profiles, particularly for those patients with advanced disease or cancers that are resistant to existing therapeutics.

BRIEF SUMMARY

The invention provides a method of treating non-small cell lung cancer (NSCLC) in a human patient, comprising administering 1 mg/kg of MEDI4736 or an antigen-binding fragment thereof and 1 mg/kg tremelimumab or an antigen-binding fragment thereof to the patient.

The invention also provides a method of treating a NSCLC in a human patient, comprising administering 3 mg/kg of MEDI4736 or an antigen-binding fragment thereof and 1 mg/kg tremelimumab or an antigen-binding fragment thereof to the patient.

The invention also provides a method of treating NSCLC in a human patient, comprising administering 10 mg/kg of MEDI4736 or an antigen-binding fragment thereof and 1 mg/kg tremelimumab or an antigen-binding fragment thereof to the patient.

The invention also provides a method of treating NSCLC in a human patient, comprising administering 15 mg/kg of MEDI4736 or an antigen-binding fragment thereof and 1 mg/kg tremelimumab or an antigen-binding fragment thereof to the patient.

The invention also provides a method of treating NSCLC in a human patient, comprising administering 10 mg/kg of MEDI4736 or an antigen-binding fragment thereof and 3 mg/kg tremelimumab or an antigen-binding fragment thereof to the patient.

The invention also provides a method of treating NSCLC in a human patient, comprising administering 15 mg/kg of MEDI4736 or an antigen-binding fragment thereof and 3 mg/kg tremelimumab or an antigen-binding fragment thereof to the patient.

The invention also provides a method of treating NSCLC in a human patient, comprising administering 20 mg/kg of MEDI4736 or an antigen-binding fragment thereof and 1 mg/kg tremelimumab or an antigen-binding fragment thereof to the patient.

The invention also provides a method of treating NSCLC in a human patient, comprising administering 15 mg/kg of MEDI4736 or an antigen-binding fragment thereof and 10 mg/kg tremelimumab or an antigen-binding fragment thereof to the patient.

The invention also provides a method of treating NSCLC in a human patient, comprising administering 20 mg/kg of MEDI4736 or an antigen-binding fragment thereof and 3 mg/kg tremelimumab or an antigen-binding fragment thereof to the patient.

The invention also provides a method of treating NSCLC in a human patient, comprising administering 20 mg/kg of MEDI4736 or an antigen-binding fragment thereof and 10 mg/kg tremelimumab or an antigen-binding fragment thereof to the patient.

The invention also provides a method of treating NSCLC in a human patient, comprising administering 10 mg/kg of MEDI4736 or an antigen-binding fragment thereof and 10 mg/kg tremelimumab or an antigen-binding fragment thereof to the patient.

The invention also provides a method of treating NSCLC in a human patient, comprising administering 3 mg/kg of MEDI4736 or an antigen-binding fragment thereof and 3 mg/kg tremelimumab or an antigen-binding fragment thereof to the patient.

The invention also provides a method of treating NSCLC in a human patient, comprising administering 3 mg/kg of MEDI4736 or an antigen-binding fragment thereof and 10 mg/kg tremelimumab or an antigen-binding fragment thereof to the patient.

The invention also provides a method of treating NSCLC in a human patient, comprising administering 1 mg/kg of MEDI4736 or an antigen-binding fragment thereof and 3 mg/kg tremelimumab or an antigen-binding fragment thereof to the patient.

The invention also provides a method of treating NSCLC in a human patient, comprising administering 1 mg/kg of MEDI4736 or an antigen-binding fragment thereof and 10 mg/kg tremelimumab or an antigen-binding fragment thereof to the patient.

The invention also provides a method of treatment comprising administering MEDI4736 or an antigen-binding fragment thereof (e.g., at 1 mg/kg, 3 mg/kg, 10 mg/kg, 15 mg/kg, or 20 mg/kg), and tremelimumab or an antigen-binding fragment thereof (e.g., at 1 mg/kg, 3 mg/kg, 10 mg/kg) to a patient identified as having a PD-L1$^-$ or PD-L1$^+$ NSCLC.

In particular embodiments of any of the previous methods, the MEDI4736 is administered every 4 weeks. In one particular embodiment, the MEDI4736 is administered every 4 weeks for 49 weeks. In particular embodiments of any of the previous methods, the MEDI4736 is administered every 2 weeks. In another embodiment, a total of 13 doses of MEDI4736 is administered.

In particular embodiments of the previous aspects, the tremelimumab is administered every 4 weeks for the first 21 weeks. In other embodiments of the previous aspects, the tremelimumab is administered every 12 weeks from weeks 25 to 49. In still other embodiments of the previous aspects, a total of 9 doses of tremelimumab is administered.

The invention also provides a method of treating NSCLC in a human patient, comprising administering 10 mg/kg of MEDI4736 or an antigen-binding fragment thereof and 1 mg/kg tremelimumab or an antigen-binding fragment thereof to the patient, where the MEDI4736 is administered every 2 weeks.

The invention also provides a method of treating NSCLC in a human patient, comprising administering 10 mg/kg of MEDI4736 or an antigen-binding fragment thereof and 3 mg/kg tremelimumab or an antigen-binding fragment thereof to the patient, where the MEDI4736 is administered every 2 weeks.

The invention also provides a method of treating NSCLC in a human patient, comprising administering 10 mg/kg of MEDI4736 or an antigen-binding fragment thereof and 10 mg/kg tremelimumab or an antigen-binding fragment thereof to the patient, wherein the MEDI4736 is administered every 2 weeks.

In particular embodiments of the previous aspects, the tremelimumab is administered every 4 weeks for the first 25 weeks. In other embodiments of the previous aspects, the tremelimumab is administered every 12 weeks from weeks 25 to 49. In still other embodiments of the previous aspects, a total of 9 doses of tremelimumab is administered.

The invention also provides a method of treating NSCLC in a human patient comprising administering MEDI4736 or an antigen-binding fragment thereof and tremelimumab or an antigen-binding fragment thereof to the patient, wherein the administrations result in a tumor response.

In the method of the invention, the administrations result in an increased tumor response as compared to the administration of either the MEDI4736 or an antigen-binding fragment thereof or the tremelimumab or an antigen-binding fragment thereof alone.

In some embodiments, the tumor response can be detected by week 2, 4, 6, 8, or 10. In other embodiments, the tumor response can be detected by week 33. In other embodiments, the tumor response can be detected by week 50.

The invention also provides a method of treating NSCLC in a human patient comprising administering MEDI4736 or an antigen-binding fragment thereof and tremelimumab or an antigen-binding fragment thereof to the patient, wherein the administrations increase progression-free survival. In some embodiments, the administrations result in an increase in progression-free survival as compared to the administration of either the MEDI4736 or an antigen-binding fragment thereof or the tremelimumab or an antigen-binding fragment thereof alone.

The invention also provides a method of treating NSCLC in a human patient comprising administering MEDI4736 or an antigen-binding fragment thereof and tremelimumab or an antigen-binding fragment thereof to the patient, wherein the administrations increase overall survival. In some embodiments, the administrations result in an increase in overall survival as compared to the administration of either the MEDI4736 or an antigen-binding fragment thereof or the tremelimumab or an antigen-binding fragment thereof alone.

In some embodiments of the methods of the invention, the administrations result in a tumor response. In some embodiments, the administrations result in an increased tumor response as compared to the administration of either the MEDI4736 or an antigen-binding fragment thereof or the tremelimumab or an antigen-binding fragment thereof alone. In some embodiments, the tumor response can be detected by week 8. In some embodiments, the tumor response can be detected by week 33.

In some embodiments of the methods of the invention, the administrations increase progression-free survival. In some embodiments, the administrations result in an increase in progression-free survival as compared to the administration of either the MEDI4736 or an antigen-binding fragment thereof or the tremelimumab or an antigen-binding fragment thereof alone.

In some embodiments of the methods of the invention, the administrations increase overall survival. In some embodiments, the administrations result in an increase in overall survival as compared to the administration of either the MEDI4736 or an antigen-binding fragment thereof or the tremelimumab or an antigen-binding fragment thereof alone.

In particular embodiments of any of the previous methods, the MEDI4736 is administered every 4 weeks. In one particular embodiment, the MEDI4736 is administered every 4 weeks for 49 weeks. In another embodiment, a total of 13 doses of MEDI4736 is administered.

In particular embodiments of the previous aspects, the tremelimumab is administered every 4 weeks for the first 21 weeks. In other embodiments of the previous aspects, tremelimumab is administered every 12 weeks from weeks 25 to 49 or following the first 6 doses. In still other embodiments of the previous aspects, a total of 9 doses of tremelimumab is administered.

In some embodiments of the method of the invention, the administration of tremelimumab or an antigen-binding fragment thereof is administered about every 4 weeks for seven administrations and then every 12 weeks.

In some embodiments of the method of the invention, the administration reduces soluble PD-L1. In some embodiments, soluble PD-L1 is reduced by at least about 65%, 80%, 90%, 95% or 99%.

In some embodiments of the methods of the invention, the tumor is refractory to at least one chemotherapeutic agent. Such chemotherapeutic agents may include, but are not limited to Vemurafenib, Erlotinib, Afatinib, Cetuximab, Carboplatin, Bevacizumab, Erlotinib, Gefitinib, or Pemetrexed.

In some embodiments of the methods of the invention, the patient has an Eastern Cooperative Oncology Group (ECOG) performance status of 0-1.

In some embodiments of the methods of the invention, the patient is immunotherapy-naïve prior to the administration of MEDI4736 or antigen-binding fragment thereof and tremelimumab or antigen-binding fragment thereof.

In some embodiments of the methods of the invention, the patient has received immunotherapy prior to the administration of MEDI4736 or antigen-binding fragment thereof and tremelimumab or antigen-binding fragment thereof.

In some embodiments of the methods of the invention, the administration of MEDI4736 or an antigen-binding fragment thereof is by intravenous infusion.

In some embodiments of the methods of the invention, the administration of tremelimumab or an antigen-binding fragment thereof is by intravenous infusion.

In particular embodiments of the methods of the invention, the administrations reduce tumor size by at least about 10%, 25%, 50%, 75% or 100% relative to baseline.

In particular embodiments of the methods of the invention, the human patient has locally advanced unresectable or metastatic NSCLC. In particular embodiments of the methods of the invention, the NSCLC is squamous or non-squamous. In other embodiments of the methods of the invention, the NSCLC comprises a KRAS-mutation or an EGFR-mutation.

In some embodiments of the methods of the invention, the MEDI4736 or an antigen-binding fragment thereof is MEDI4736 and wherein the tremelimumab or an antigen-binding fragment thereof is tremelimumab.

In another aspect the invention provides for a method of treating cancer with MEDI4736 or an antigen-binding fragment of MEDI4736 in combination with tremelimumab or an antigen-binding fragment of tremelimumab. In some embodiments of the invention the cancer is selected from prostate cancer, breast cancer, triple negative breast cancer, colon cancer, lung cancer, NSCLC, head and neck cancer, melanoma, gastric cancer, pancreatic cancer, ovarian cancer, renal cell carcinoma, and hepatic cancer.

BRIEF DESCRIPTION OF THE DRAWINGS/FIGURES

Figure 4:
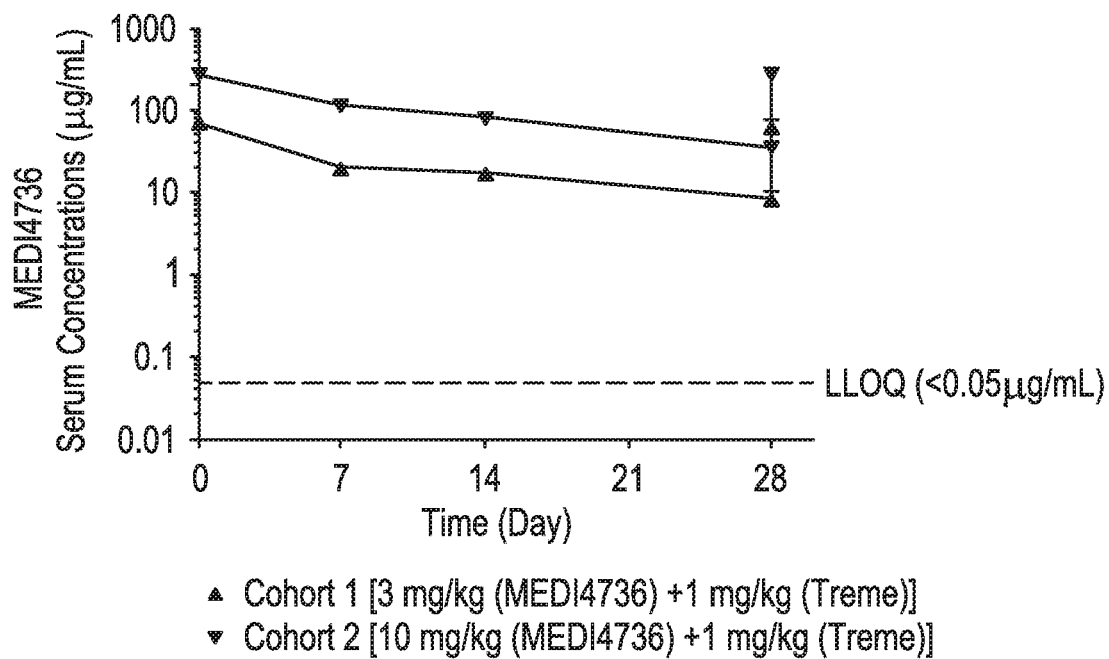

FIG. 4 provides a graph and a table showing the pharmacokinetic (PK) profile of MEDI4736. Q4W=every 4 weeks. LLOQ=Lower limit of Quantification. AUC=area under curve.

Figure 5:
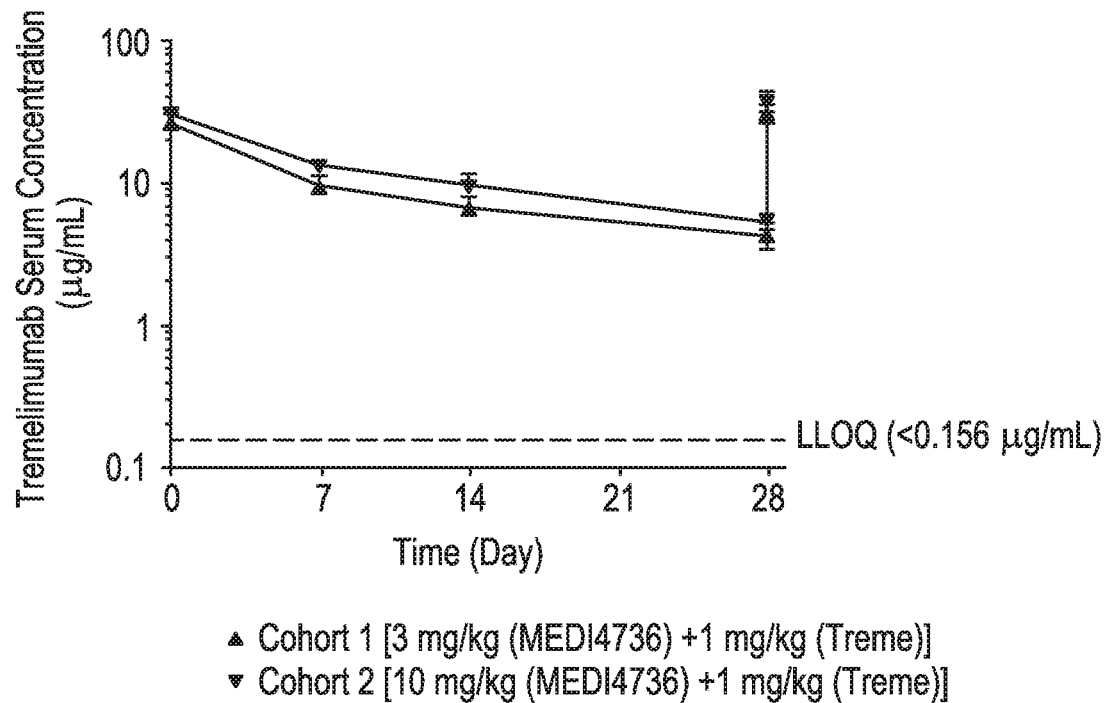

FIG. 5 provides a graph and a table showing the pharmacokinetic profile of tremelimumab.

Figure 6:
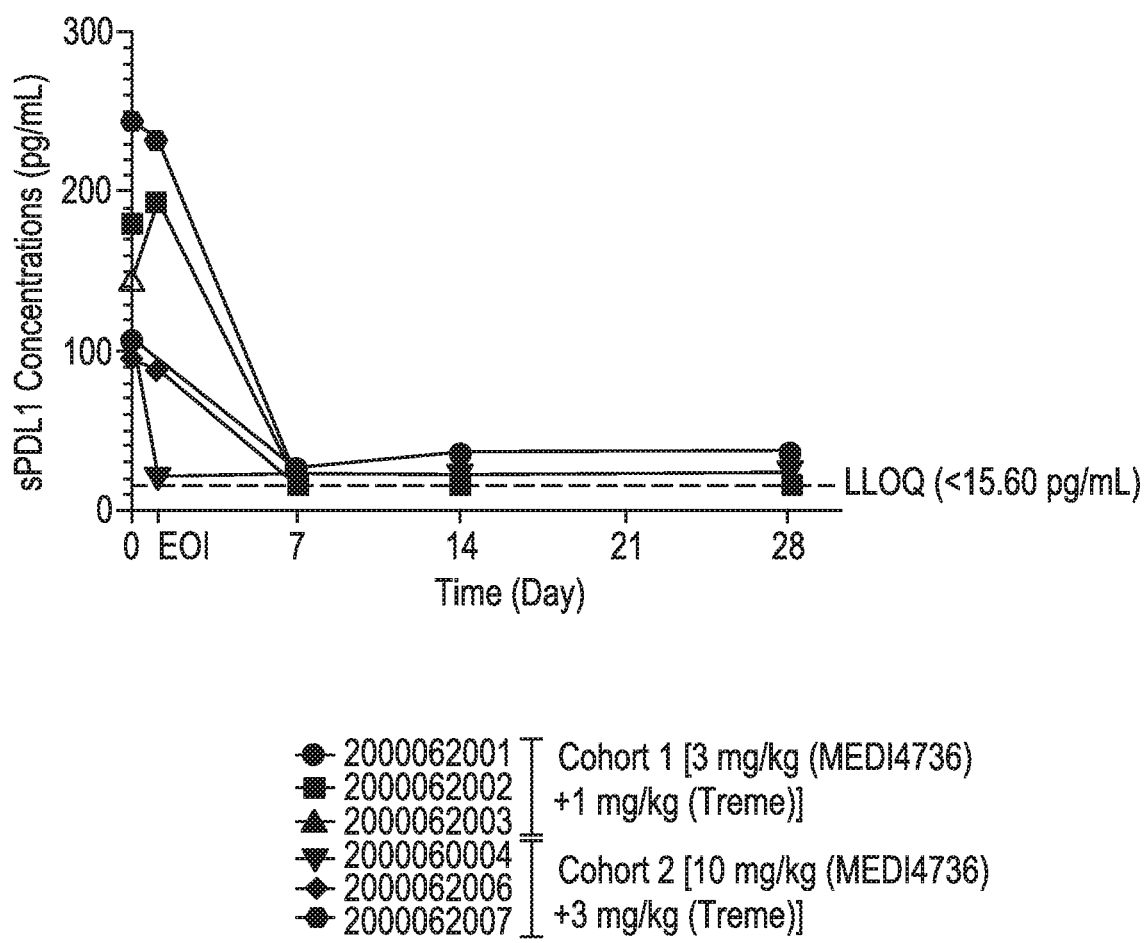

FIG. 6 is a graph showing the absolute concentration of soluble PD-L1 profiles (sPD-L1).

Figure 7:
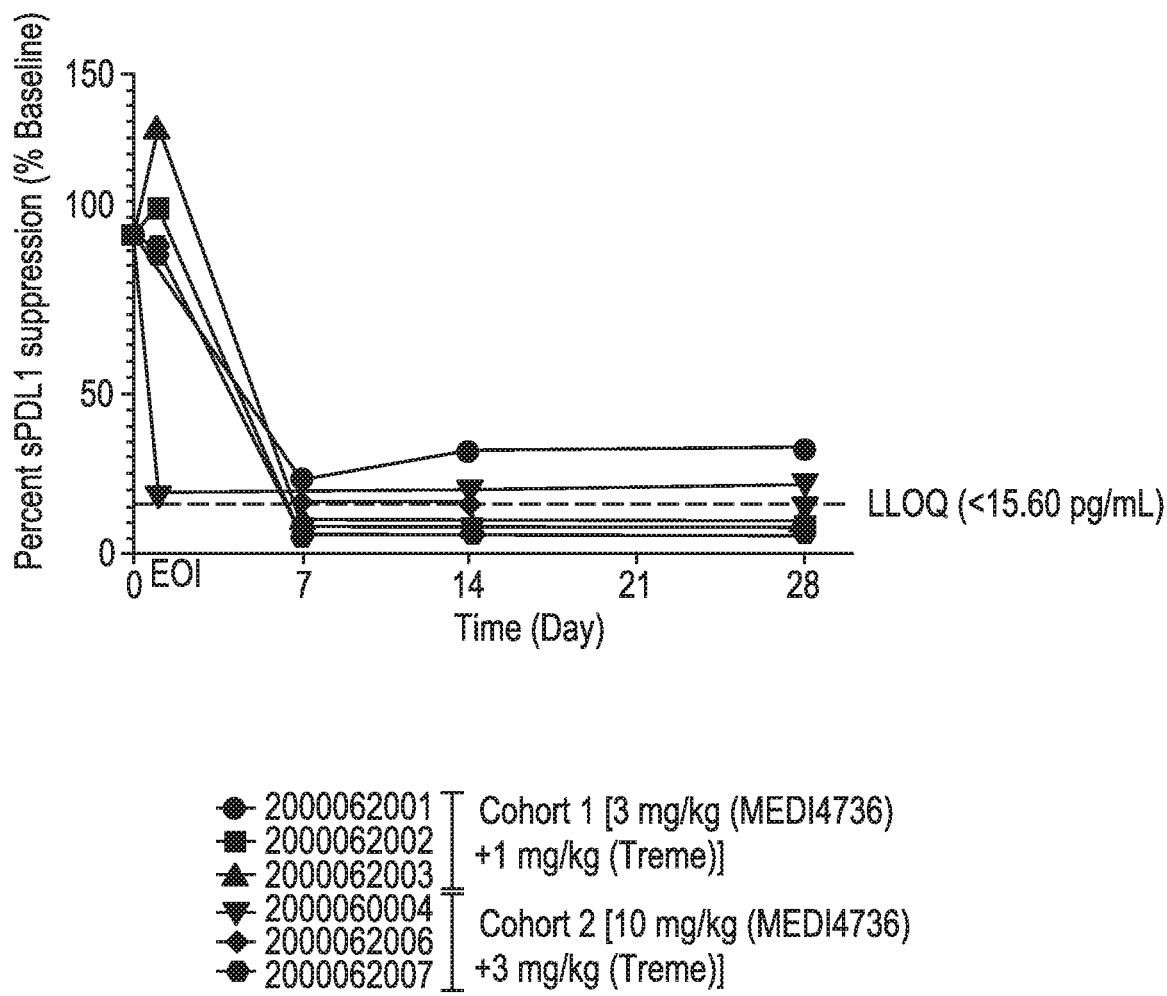

FIG. 7 is a graph showing the percent suppression of soluble PD-L1.

Figure 8:
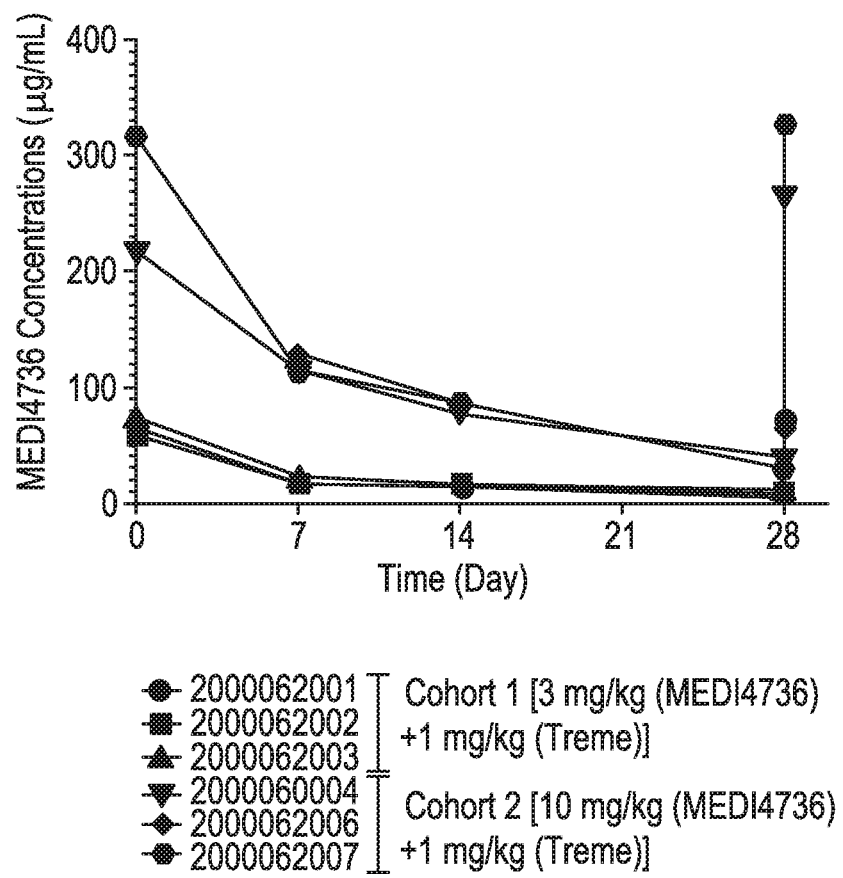

FIG. 8 is a graph showing the pharmacokinetic (PK) parameters of MEDI4736 in individual patients.

FIG. 9 is a graph showing the pharmacokinetic (PK) parameters of tremelimumab in individual patients.

FIGS. 10A and 10B are tables showing MEDI4736 and tremelimumab dose modification due to grade 1 or grade 2 toxicity (10A) and grade 3 or grade 4 toxicity (10B).

FIG. 11 is a table showing Study criteria.

FIG. 12 shows study enrollment.

FIG. 13 shows related adverse events (AEs) for patients dosed.

Figure 14:
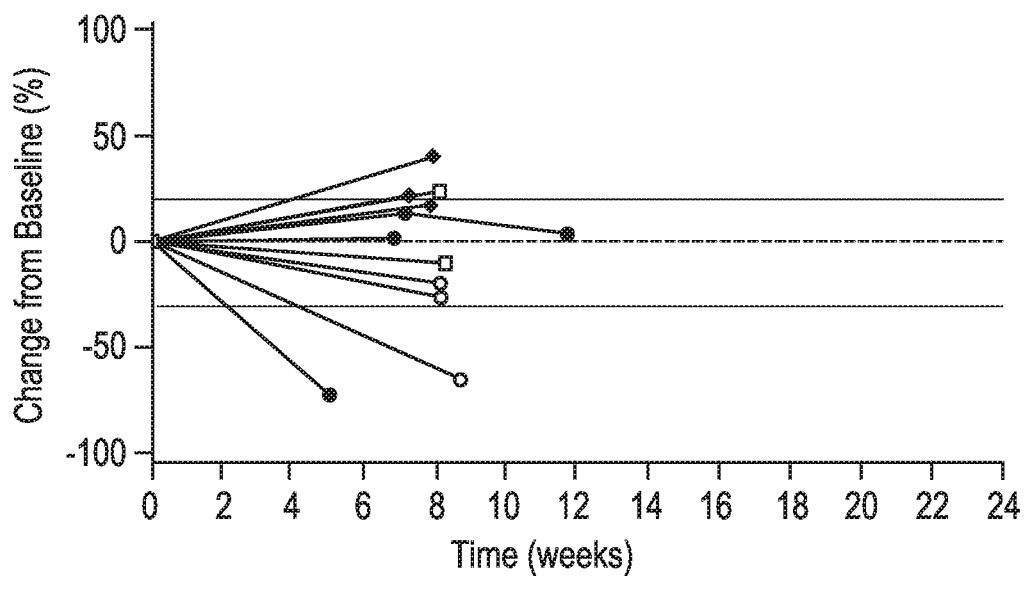

FIG. 14 shows tumor size change from baseline in first four cohorts.

Figure 15:
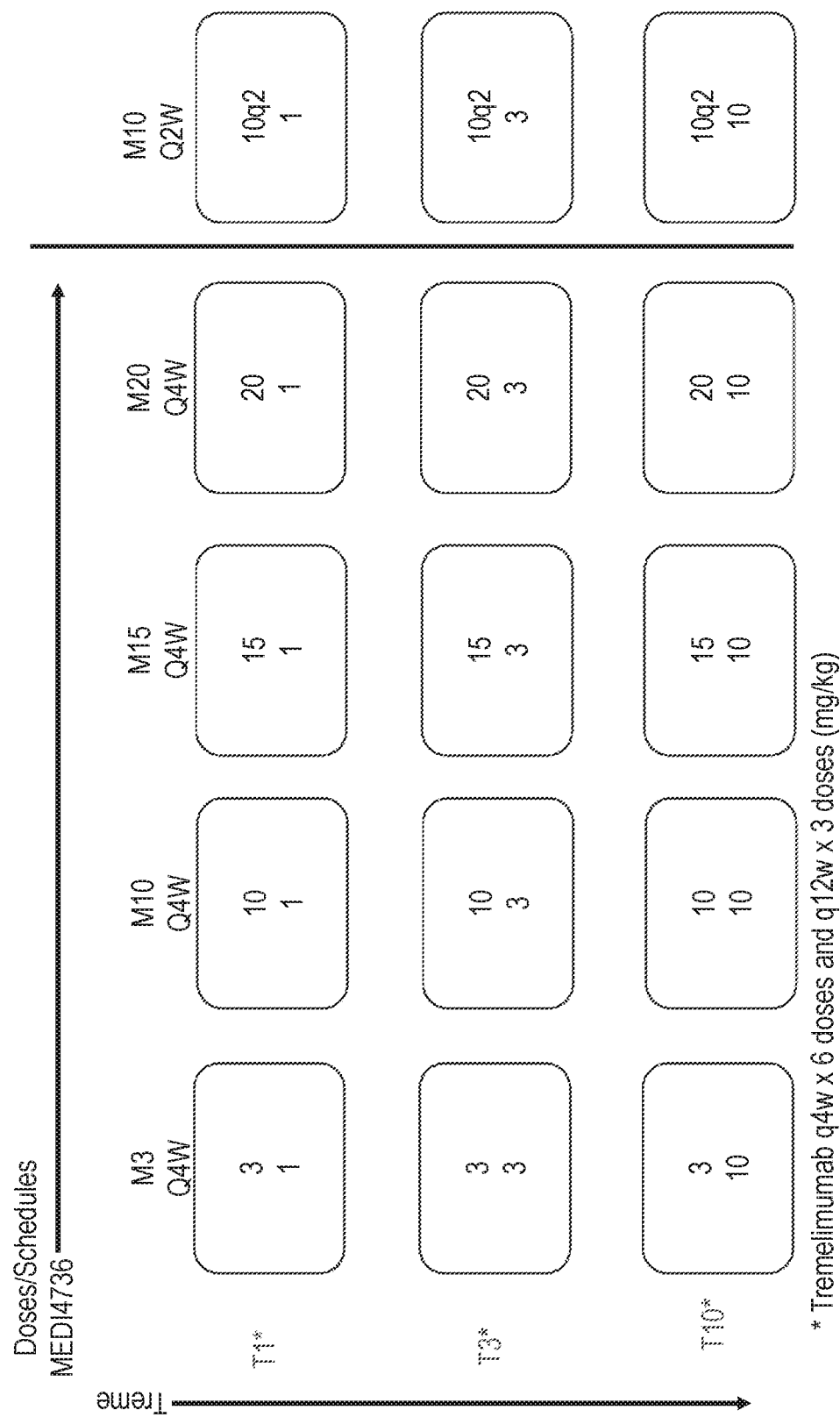

FIG. 15 shows MEDI4736 and tremelimumab doses and schedules studied.

FIG. 16 shows suppression of sPD-L1 in individual profiles receiving MEDI4736 and tremelimumab in combination.

FIG. 17 shows suppression of sPD-L1 in individual profiles receiving MEDI4736 and tremelimumab in combination grouped by cohort.

Figure 18:
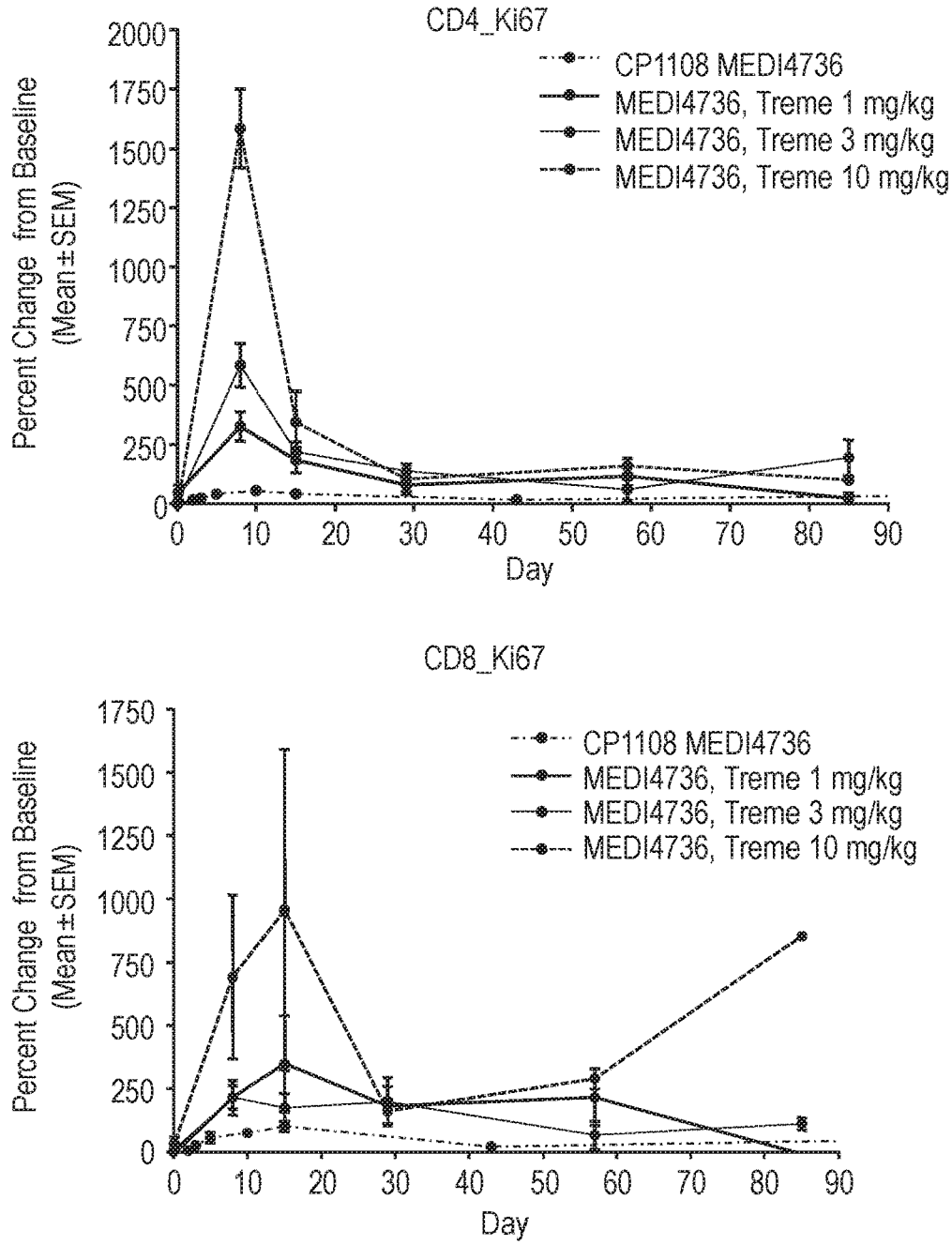

FIG. 18 shows an increase in CD4 Ki67+ and CD8 Ki67 proliferating cells from baseline in subjects receiving MEDI4736 and tremelimumab compared to increases in those receiving MEDI4736 alone. Increases in CD4 Ki67+ and CD8 Ki67 proliferating cells from baseline correlated with increasing tremelimumab dose.

Figure 19:
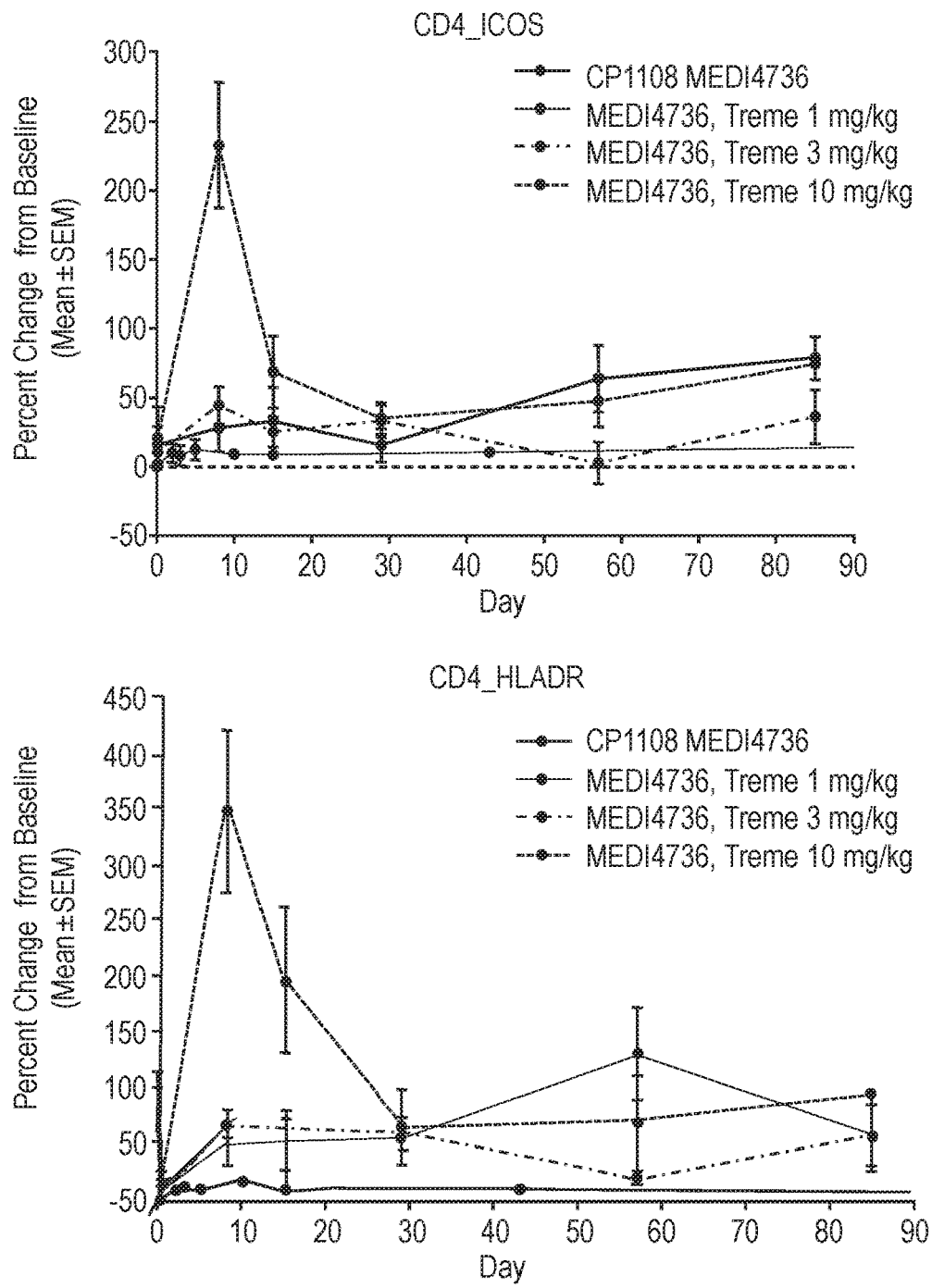

FIG. 19 shows an increase in CD4 ICOS+ and CD4 HLADR+ cells from baseline in subjects receiving MEDI4736 and tremelimumab compared to increases in those receiving MEDI4736 alone. Increases in CD4 ICOS+ and CD4 HLADR+ cells from baseline correlated with increasing tremelimumab dose.

Figure 20:
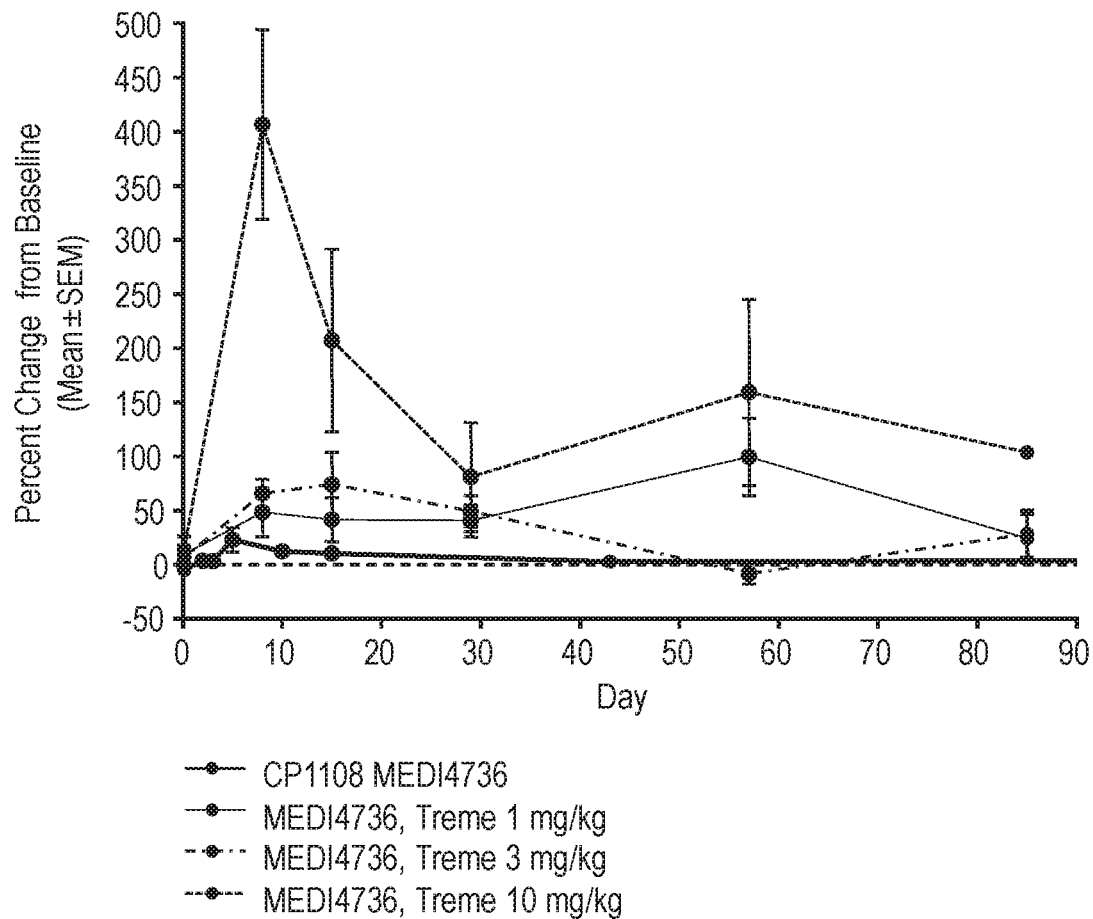

FIG. 20 shows an increase in CD4+ T effector cells from baseline in subjects receiving MEDI4736 and tremelimumab compared to the increase in those receiving MEDI4736 alone. The increases in CD4+ T effector cells from baseline correlated with increasing tremelimumab dose.

Figure 21:
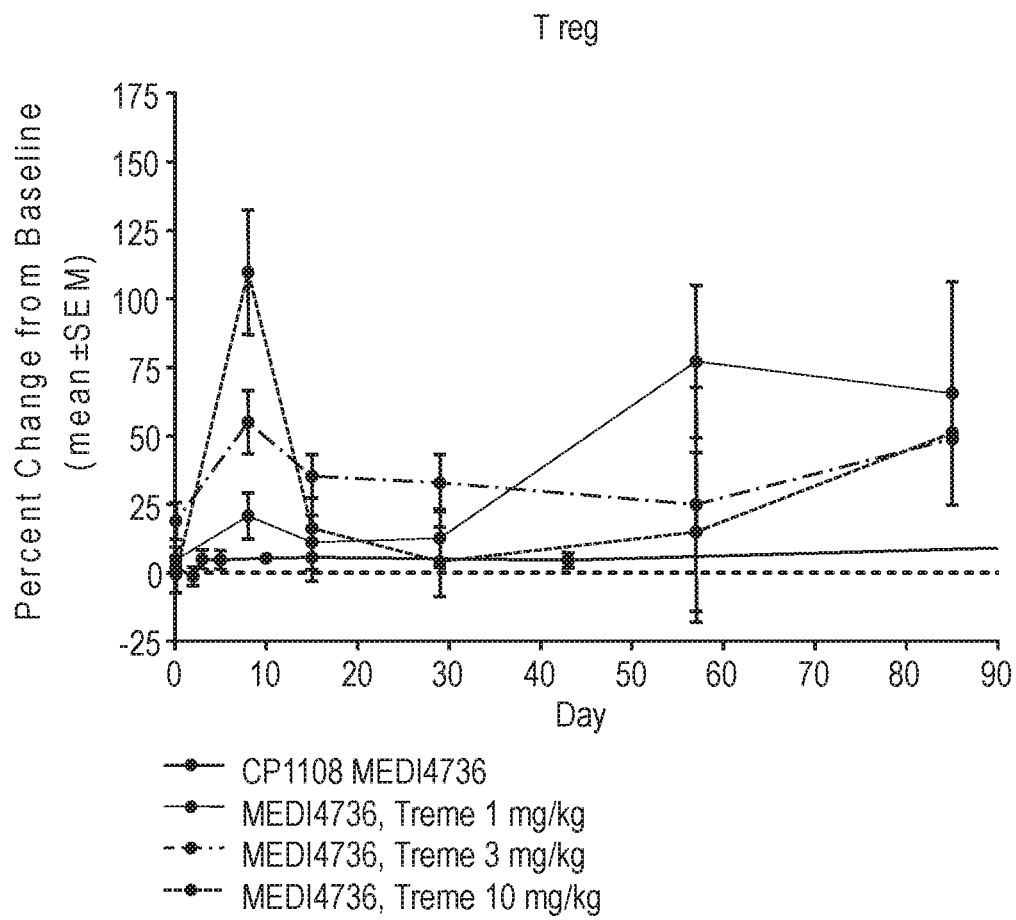

FIG. 21 shows an increase in Treg cells from baseline in subjects receiving MEDI4736 and tremelimumab compared to the increase in those receiving MEDI4736 alone. The increases in Treg cells from baseline correlated with increasing tremelimumab dose.

FIG. 22 is a table showing the clinical activity of MEDI4736 therapy in combination with tremelimumab compared to MEDI4736 monotherapy.

FIG. 23 are spider plots showing change in tumor size from baseline in cohorts anchored by tremelimumab dose: 1 mg/kg (upper left panel); 10 mg/kg (upper right panel); and 3 mg/kg (lower panel).

FIG. 24 is a graph showing time of onset of related ≥Grade 3 adverse events (AE) in combination cohorts anchored by tremelimumab dose: 1 mg/kg; 10 mg/kg; and 3 mg/kg, compared to MEDI4736 monotherapy.

Figure 25:
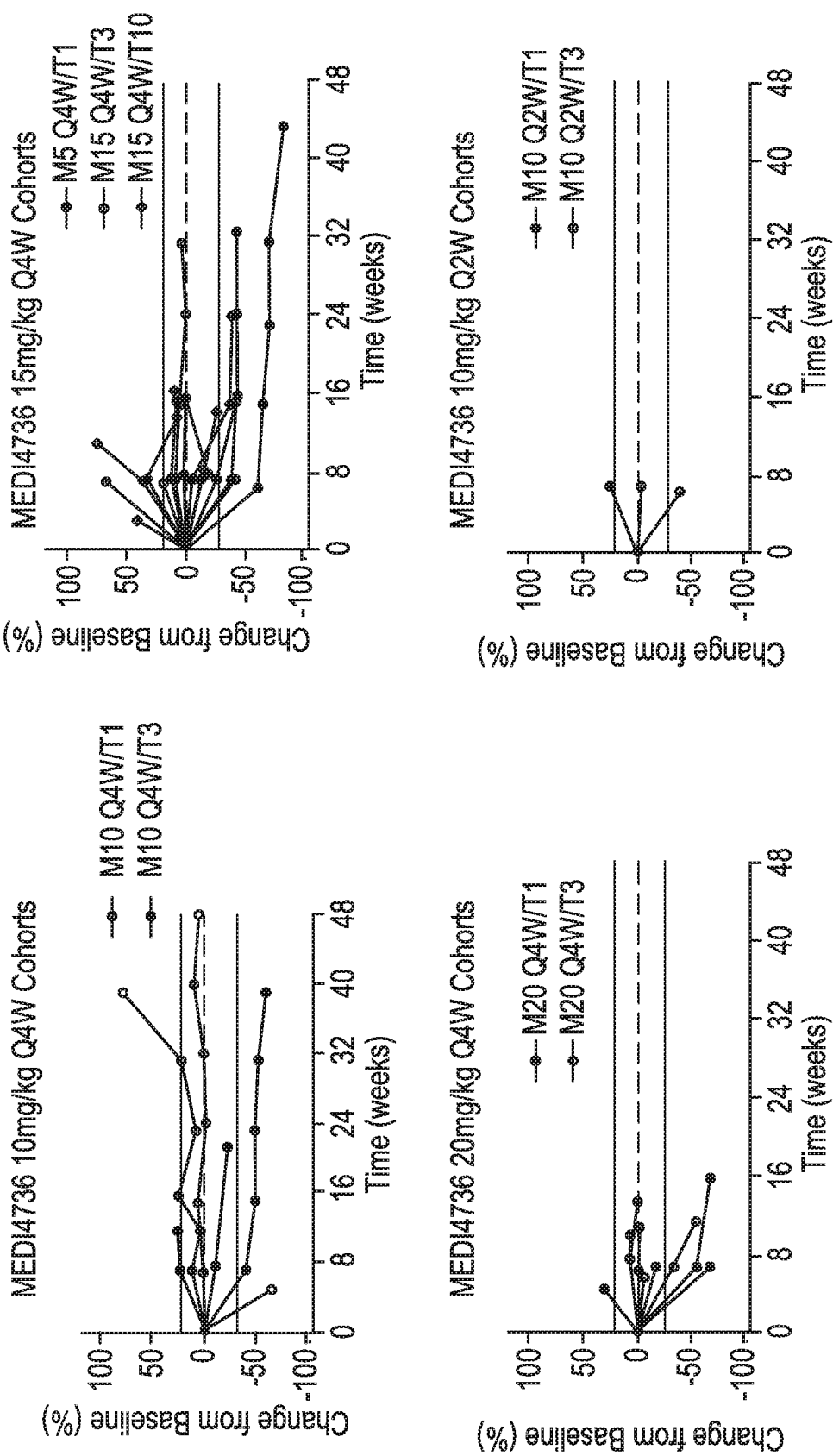

FIG. 25 are spider plots showing change in tumor size from baseline in cohorts anchored by MEDI4736 dose: 10 mg/kg Q4W (upper left panel); 15 mg/kg Q4W (upper right panel); 20 mg/kg Q4W (lower left panel); and 10 mg/kg Q2W (lower right panel).

Figure 26:
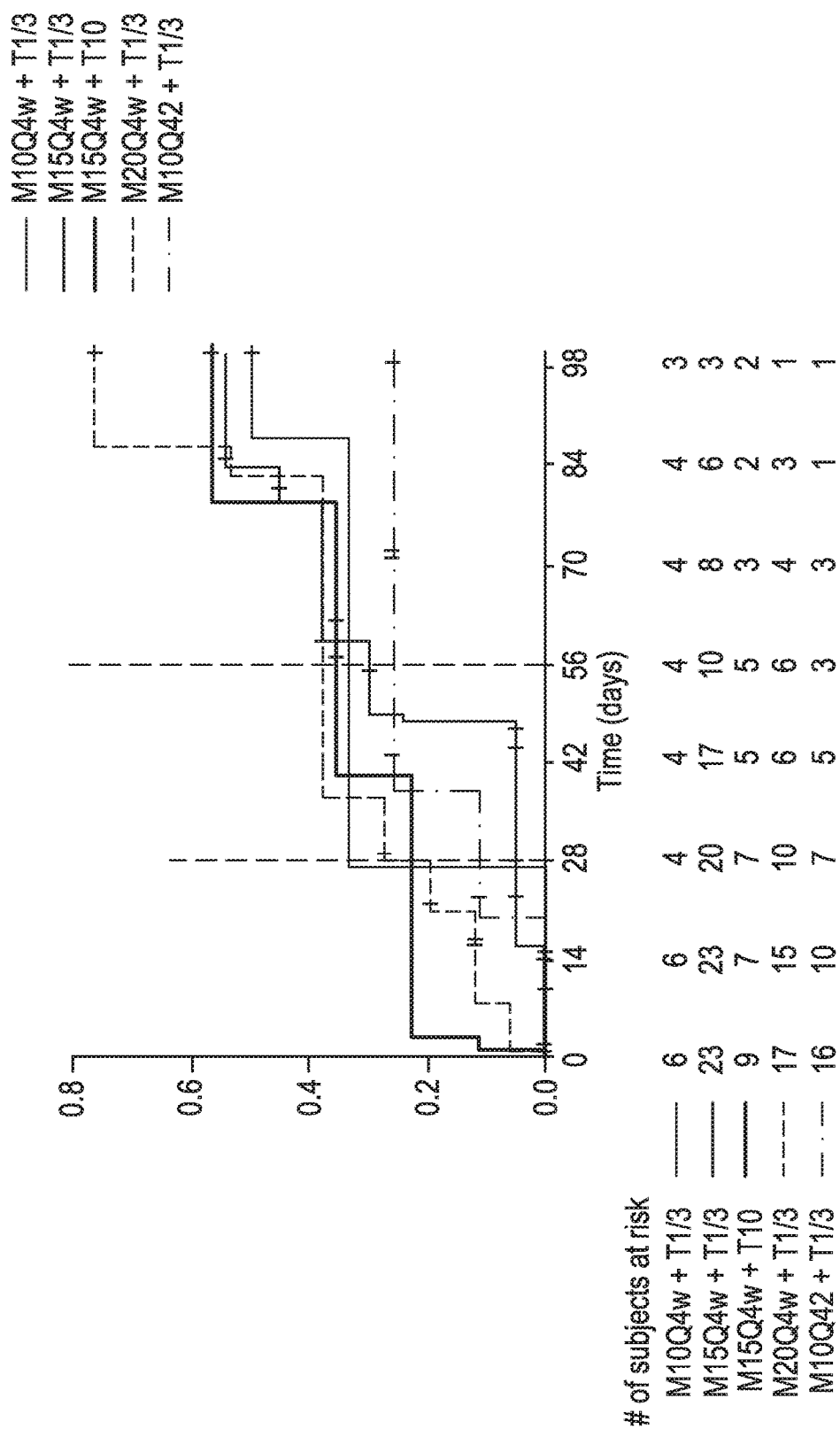

FIG. 26 is a graph showing time of onset of related ≥Grade 3 adverse events (AE) in combination cohorts anchored by MEDI4736 dose: 1 mg/kg; 10 mg/kg; and 3 mg/kg, compared to MEDI4736 monotherapy.

Figure 27:
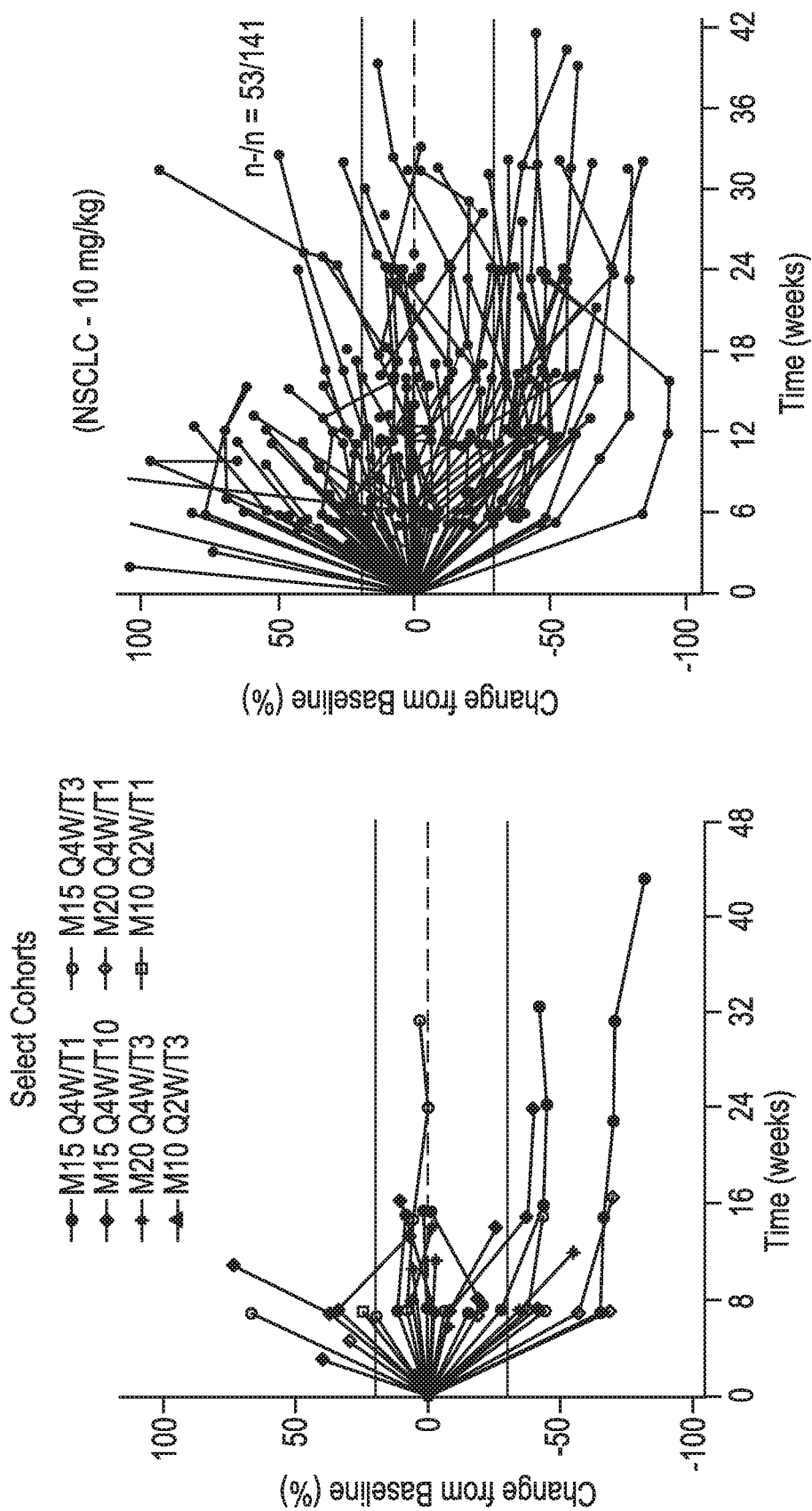

FIG. 27 are spider plots showing change in tumor size from baseline in selected cohorts of NSCLC patients receiving MEDI4736 and tremelimumab (left panel) compared to those receiving MEDI4736 (10 mg/kg Q4W) alone (right panel).

Figure 28:
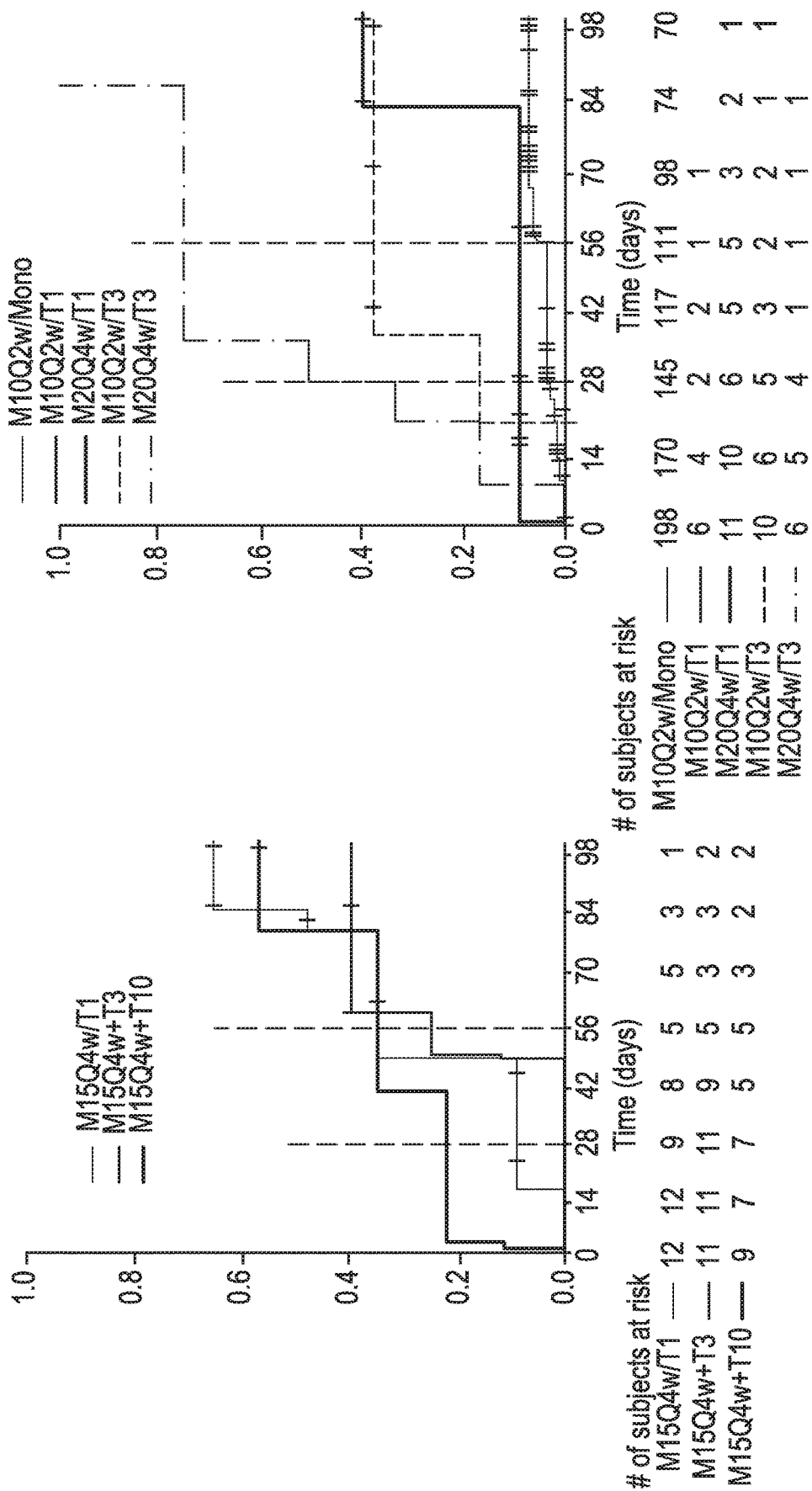

FIG. 28 are graphs showing time of onset of related ≥Grade 3 adverse events (AE) in selected combination cohorts (left and right panels), compared to MEDI4736 monotherapy (left panel).

Figure 29:
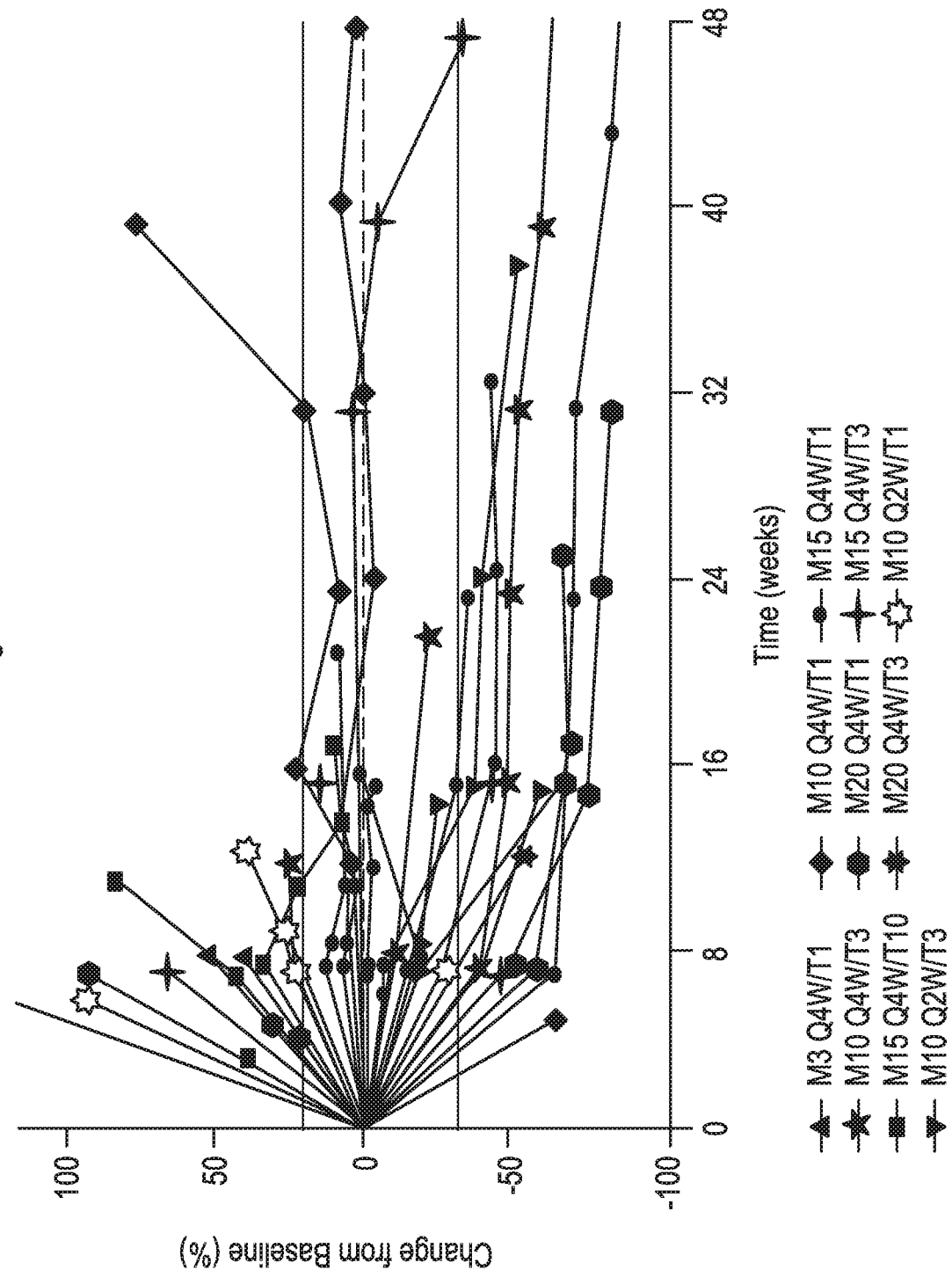

FIG. 29 are spider plots showing change in tumor size from baseline in all study cohorts of patients with NSCLC receiving MEDI4736 and tremelimumab.

Figure 30:
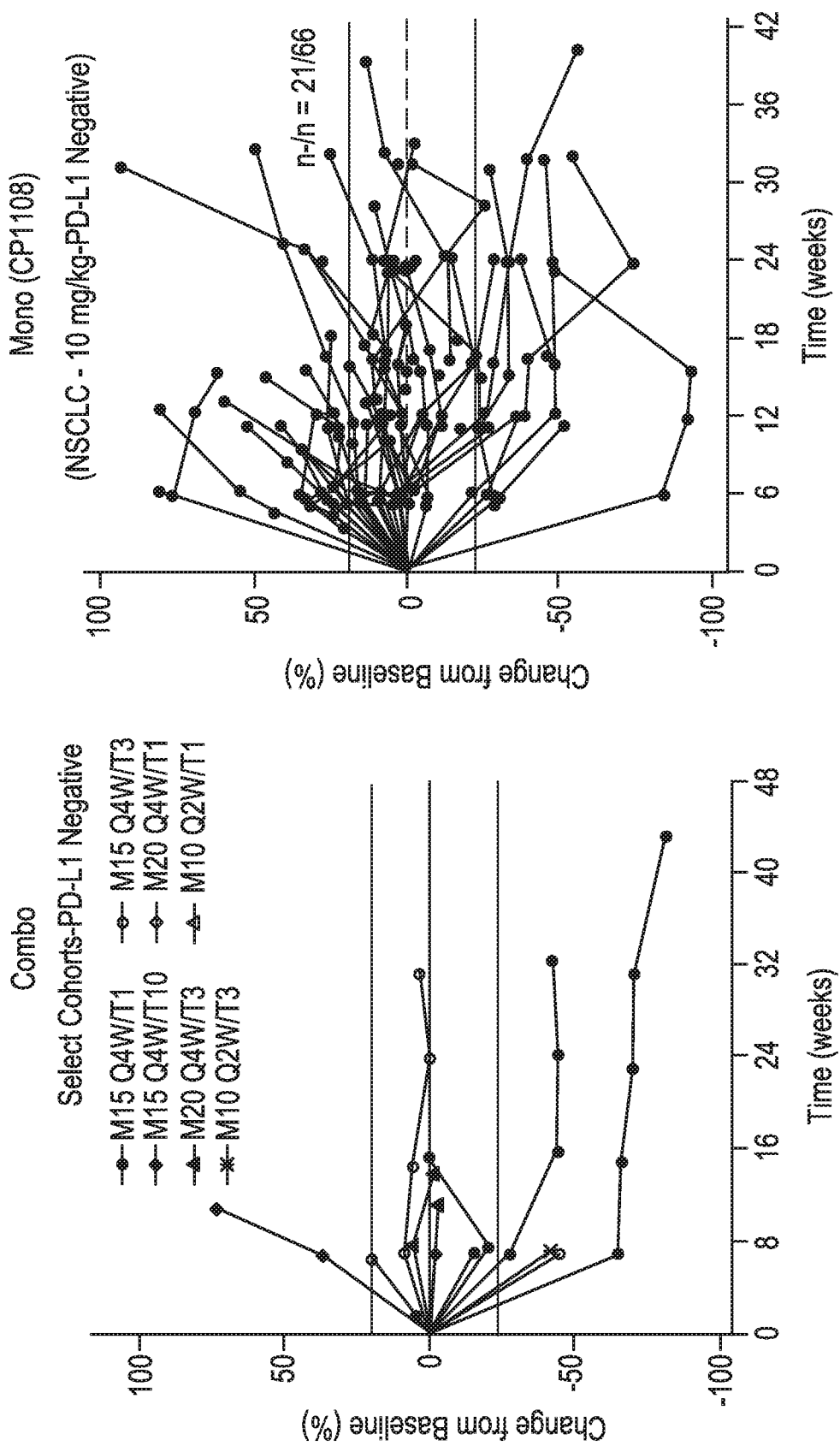

FIG. 30 are spider plots showing change in tumor size from baseline in selected cohorts of patients with PD-L1 negative NSCLC receiving MEDI4736 and tremelimumab (left panel) compared to those receiving MEDI4736 (10 mg/kg; CP1108) alone (right panel).

Figure 31:
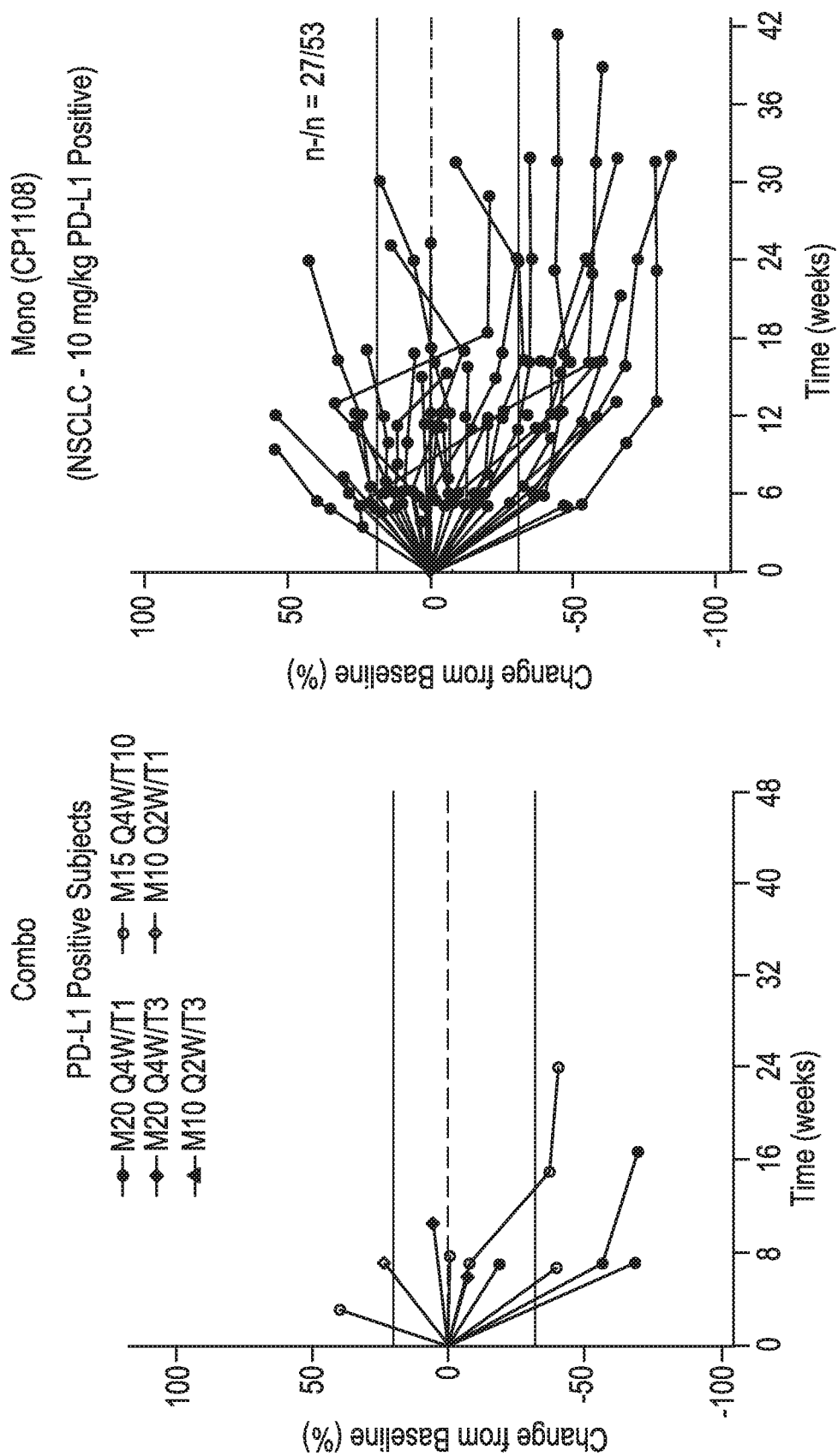

FIG. 31 are spider plots showing change in tumor size from baseline in selected cohorts of patients with PD-L1 positive NSCLC receiving MEDI4736 and tremelimumab (left panel) compared to those receiving MEDI4736 (10 mg/kg; CP1108) alone (right panel).

FIG. 32 are spider plots anchored by tremelimumab dose: 1 mg/kg (left panel), 3 mg/kg (center panel), and 10 mg/kg (right panel) showing change in tumor size from baseline in selected cohorts of patients with PD-L1 negative NSCLC receiving MEDI4736 and tremelimumab.

Figure 33:
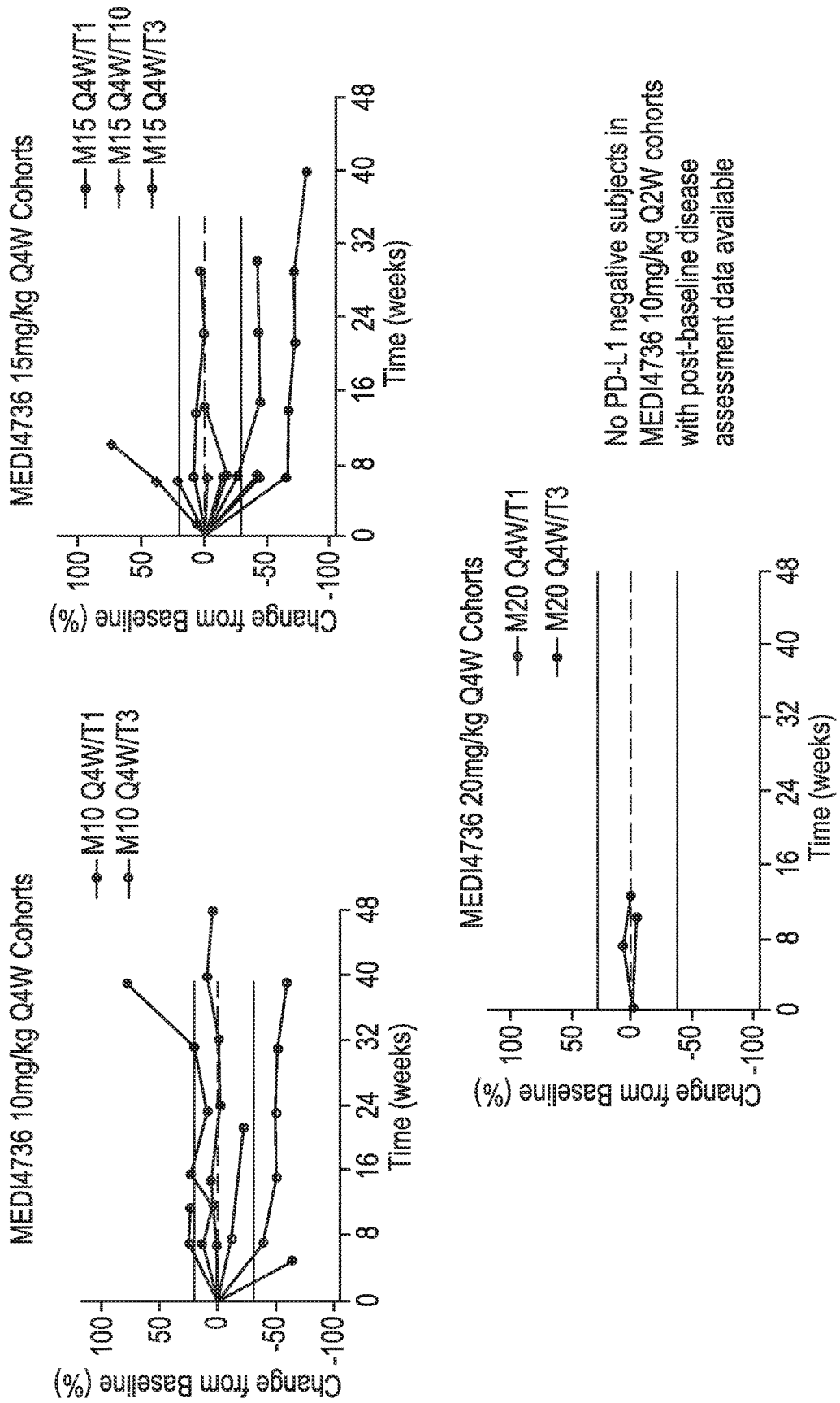
Figure 34B:
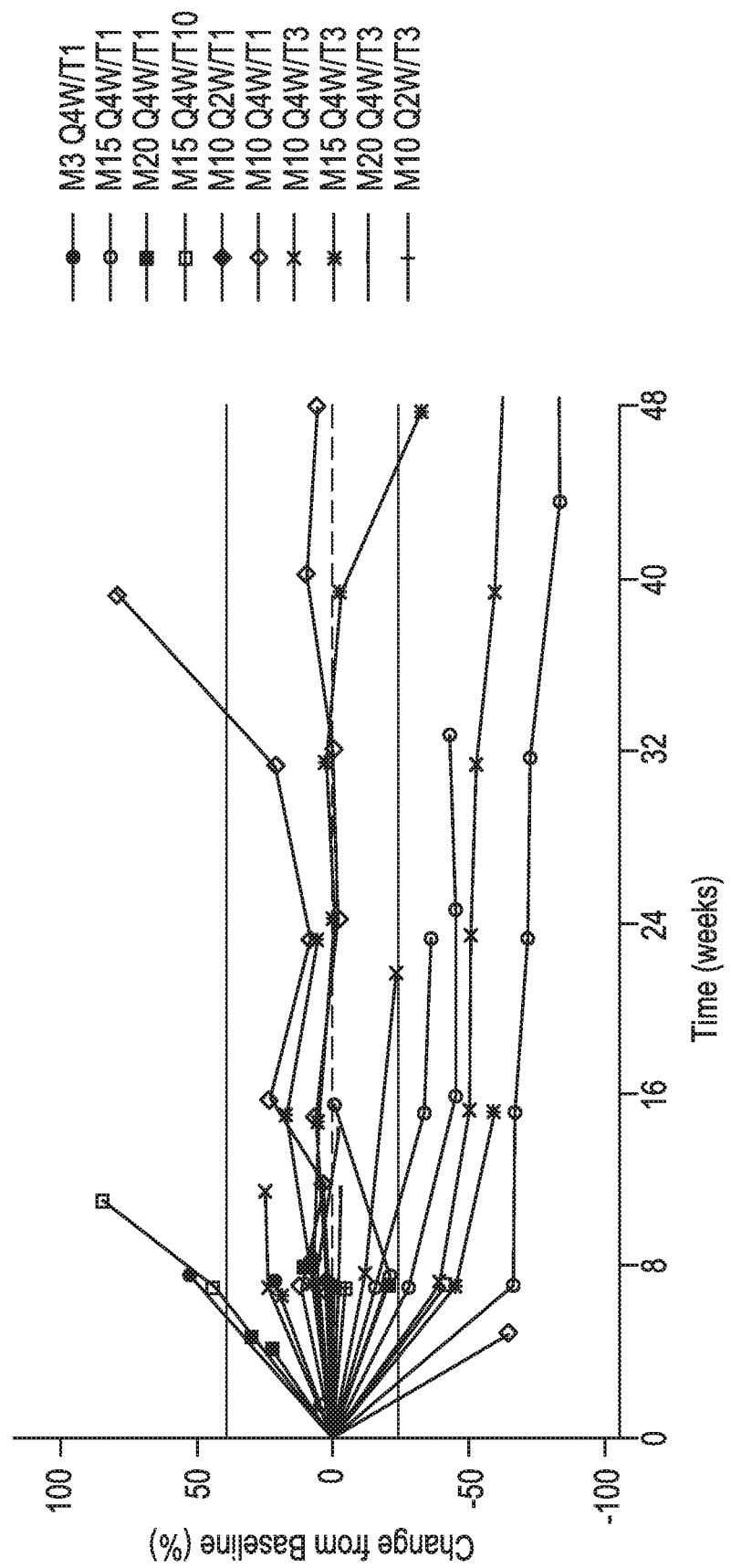

FIG. 33 are spider plots anchored by MEDI4736 dose: 10 mg/kg Q4W (upper left panel), 15 mg/kg (upper right panel), and 20 mg/kg (lower left panel) showing change in tumor size from baseline in selected cohorts of patients with PD-L1 negative NSCLC receiving MEDI4736 and tremelimumab.

FIGS. 34A-34D are spider plots showing change in tumor size from baseline in NSCLC patients receiving MEDI4736 and tremelimumab in FIG. 29, grouped according to NSCLC PD-L1 status: all NSCLC patients (34A); patients identified as having PD-L1⁻ NSCLC (34B); patients identified as having PD-L1+ NSCLC (34C); and patients with NSCLC PD-L1 status not available (34D).

FIG. 35 is a waterfall plot showing best change in tumor size from baseline in NSCLC patients receiving MEDI4736 and tremelimumab.

Figure 36:
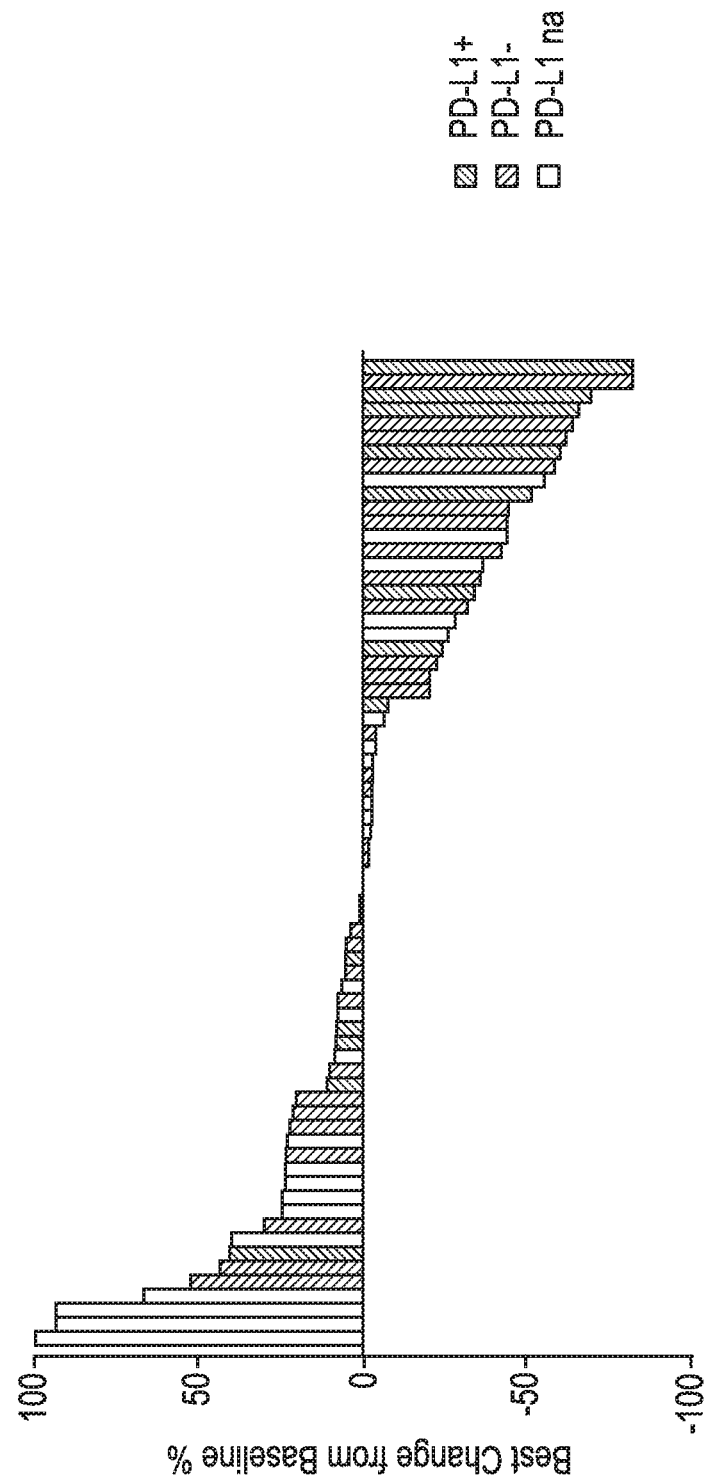

FIG. 36 is a waterfall plot showing best change in tumor size from baseline in NSCLC patients receiving MEDI4736 and tremelimumab in FIG. 35, identified according to PD-L1 status of the NSCLC.

Figure 37:
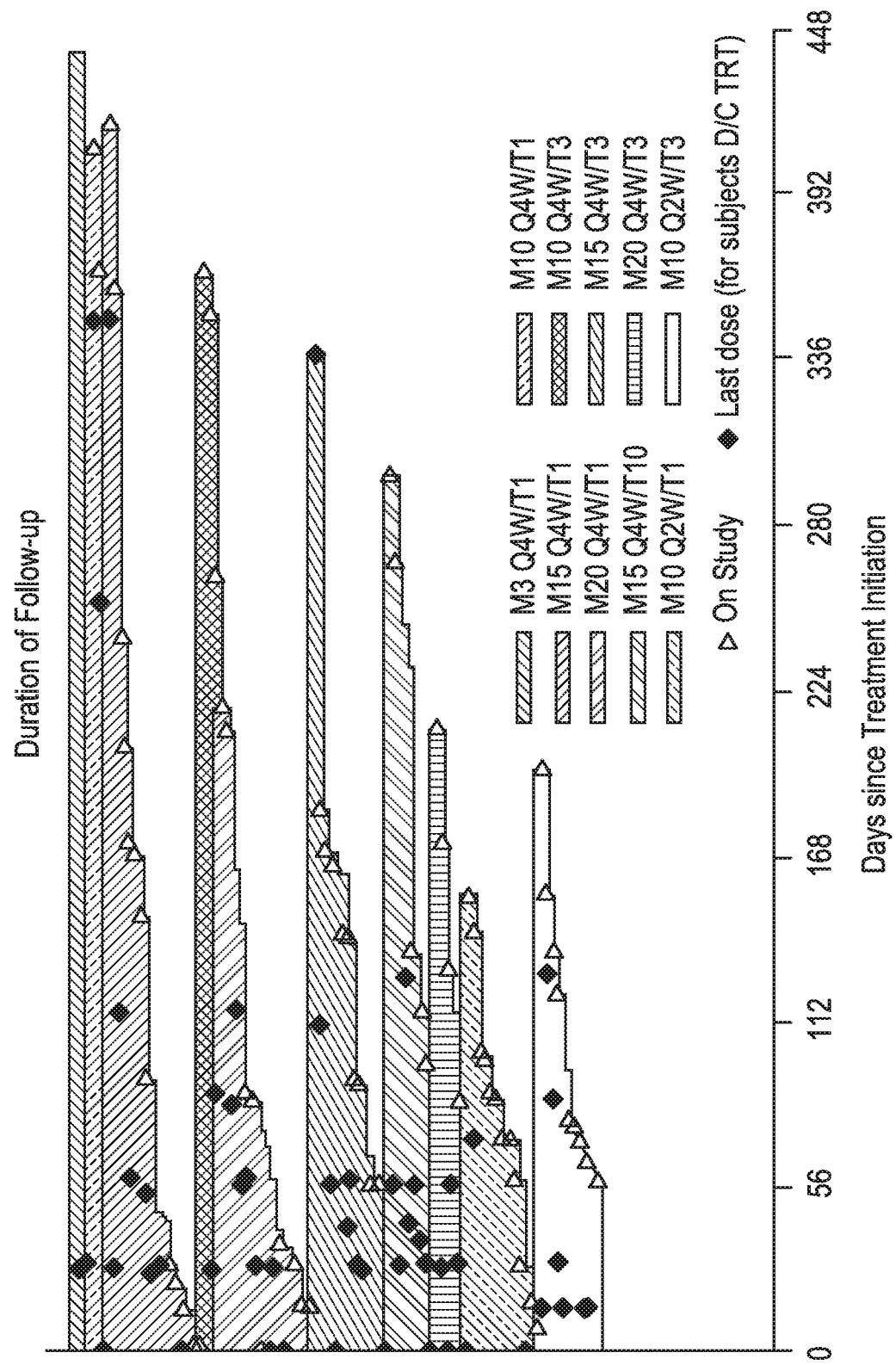

FIG. 37 is a swimlane plot showing duration of follow-up in NSCLC patients receiving MEDI4736 and tremelimumab.

DETAILED DESCRIPTION

It is to be noted that the term "a" or "an" entity refers to one or more of that entity; for example, "an antibody" is understood to represent one or more antibodies. As such, the terms "a" (or "an"), "one or more," and "at least one" can be used interchangeably herein.

Provided herein are methods for treating non-small cell lung cancer (NSCLC) using MEDI4736 and tremelimumab. There are three main subtypes of NSCLC: squamous cell carcinoma, adenocarcinoma, and large cell (undifferentiated) carcinoma. Other subtypes include adenosquamous carcinoma and sarcomatoid carcinoma. NSCLC may comprise a mutation in KRAS or in the Epidermal Growth Factor receptor. Such mutations are known in the art and described, for example, by Riely et al., Proc Am Thorac Soc. 2009 Apr. 15; 6(2):201-5, which is incorporated herein by reference.

In addition, provided herein are methods for treating cancer or neoplastic growths using MEDI4736 and tremelimumamb. As used herein "cancer" refers to a disease caused by an uncontrolled division of abnormal cells. Examples of cancer include prostate cancer, breast cancer, triple negative breast cancer, colon cancer, lung cancer, NSCLC, head and neck cancer, melanoma, gastric cancer, pancreatic cancer, ovarian cancer, renal cell carcinoma, and hepatic cancer.

The methods provided include administering an effective amount of MEDI4736 or an antigen-binding fragment thereof and tremelimumab or an antigen-binding fragment thereof.

By "MEDI4736" is meant an antibody or antigen binding fragment thereof that selectively binds a PD-L1 polypeptide and comprises at least a portion of a light chain variable region comprising the amino acid sequence of SEQ ID NO:1 and/or at least a portion of a heavy chain variable region comprising the amino acid sequence of SEQ ID NO:2.

Information regarding MEDI4736 (or antigen-binding fragments thereof) for use in the methods provided herein can be found in U.S. Pat. No. 8,779,108, the disclosure of which is incorporated herein by reference in its entirety. The fragment crystallizable (Fc) domain of MEDI4736 contains a triple mutation in the constant domain of the IgG1 heavy chain that reduces binding to the complement component C1q and the Fcγ receptors responsible for mediating antibody-dependent cell-mediated cytotoxicity (ADCC). MEDI4736 is selective for PD-L1 and blocks the binding of PD-L1 to the PD-1 and CD80 receptors. MEDI4736 can relieve PD-L1-mediated suppression of human T-cell activation in vitro and inhibits tumor growth in a xenograft model via a T-cell dependent mechanism.

MEDI4736 for use in the methods provided herein comprises a heavy chain and a light chain or a heavy chain variable region and a light chain variable region. In a specific aspect, MEDI4736 or an antigen-binding fragment thereof for use in the methods provided herein comprises a light chain variable region comprising the amino acid sequence of SEQ ID NO:1 and a heavy chain variable region comprising the amino acid sequence of SEQ ID NO:2. In a specific aspect, MEDI4736 or an antigen-binding fragment thereof for use in the methods provided herein comprises a heavy chain variable region and a light chain variable region, wherein the heavy chain variable region comprises the Kabat-defined CDR1, CDR2, and CDR3 sequences of SEQ ID NOs:3-5, and wherein the light chain variable region comprises the Kabat-defined CDR1, CDR2, and CDR3 sequences of SEQ ID NOs:6-8. Those of ordinary skill in the art would easily be able to identify Chothia-defined, Abm-defined or other CDR definitions known to those of ordinary skill in the art. In a specific aspect, MEDI4736 or an antigen-binding fragment thereof for use in the methods provided herein comprises the variable heavy chain and variable light chain CDR sequences of the 2.14H9OPT antibody as disclosed in U.S. Pat. No. 8,779,108, which is herein incorporated by reference in its entirety.

By "Tremelimumab" is meant an antibody or antigen binding fragment thereof that selectively binds a CTLA4 polypeptide and comprises at least a portion of a light chain variable region comprising the amino acid sequence of SEQ ID NO:9 and/or at least a portion of a heavy chain variable region comprising the amino acid sequence of SEQ ID NO:10. Exemplary anti-CTLA4 antibodies are described for example at U.S. Pat. Nos. 6,682,736; 7,109,003; 7,123,281; 7,411,057; 7,824,679; 8,143,379; 7,807,797; and 8,491,895 (Tremelimumab is 11.2.1, therein), which are herein incorporated by reference. Tremelimumab is an exemplary anti-CTLA4 antibody. Tremelimumab sequences are provided in the sequence listing below.

Information regarding tremelimumab (or antigen-binding fragments thereof) for use in the methods provided herein can be found in U.S. Pat. No. 6,682,736 (where it is referred to as 11.2.1, the disclosure of which is incorporated herein by reference in its entirety. Tremelimumab (also known as CP-675,206, CP-675, CP-675206, and ticilimumab) is a human IgG$_2$ monoclonal antibody that is highly selective for CTLA4 and blocks binding of CTLA4 to CD80 (B7.1) and CD86 (B7.2). It has been shown to result in immune activation in vitro and some patients treated with tremelimumab have shown tumor regression.

Tremelimumab and antigen-binding fragments thereof for use in the methods provided herein comprises a heavy chain and a light chain or a heavy chain variable region and a light chain variable region. In a specific aspect, tremelimumab or an antigen-binding fragment thereof for use in the methods provided herein comprises a light chain variable region comprising the amino acid sequence of SEQ ID NO:9 and a heavy chain variable region comprising the amino acid sequence of SEQ ID NO:10. In a specific aspect, tremelimumab or an antigen-binding fragment thereof for use in the methods provided herein comprises a heavy chain variable region and a light chain variable region, wherein the heavy chain variable region comprises the Kabat-defined CDR1, CDR2, and CDR3 sequences of SEQ ID NOs:11-13, and wherein the light chain variable region comprises the Kabat-defined CDR1, CDR2, and CDR3 sequences of SEQ ID NOs:14-16. Those of ordinary skill in the art would easily be able to identify Chothia-defined, Abm-defined or other CDR definitions known to those of ordinary skill in the art. In a specific aspect, tremelimumab or an antigen-binding fragment thereof for use in the methods provided herein comprises or the variable heavy chain and variable light chain CDR sequences of the 11.2.1 antibody as disclosed in U.S. Pat. No. 6,682,736, which is herein incorporated by reference in its entirety.

The term "antigen binding fragment" refers to a portion of an intact antibody and/or refers to the antigenic determining variable regions of an intact antibody. It is known that the antigen binding function of an antibody can be performed by fragments of a full-length antibody. Examples of antibody fragments include, but are not limited to, Fab, Fab', F(ab')2, and Fv fragments, linear antibodies, single chain antibodies, diabodies, and multispecific antibodies formed from antibody fragments.

In certain aspects, a patient presenting with a NSCLC is administered MEDI4736 or an antigen-binding fragment thereof and tremelimumab or an antigen-binding fragment thereof. MEDI4736 or an antigen-binding fragment thereof and tremelimumab or an antigen-binding fragment thereof can be administered only once or infrequently while still providing benefit to the patient. In further aspects the patient is administered additional follow-on doses. Follow-on doses can be administered at various time intervals depending on the patient's age, weight, clinical assessment, tumor burden, and/or other factors, including the judgment of the attending physician.

The intervals between doses of MEDI4736 or an antigen-binding fragment thereof can be every four weeks. The intervals between doses of tremelimumab or an antigen-binding fragment thereof can be every four weeks. The intervals between doses of tremelimumab or an antigen-binding fragment thereof can be every twelve weeks. The intervals between doses of tremelimumab or an antigen-binding fragment thereof can be every four weeks for six cycles and then every twelve weeks.

In certain aspects, MEDI4736 or an antigen-binding fragment thereof is administered about as frequently as tremelimumab or an antigen-binding fragment thereof. In certain aspects, MEDI4736 or an antigen-binding fragment thereof is administered about three times as frequently as tremelimumab or an antigen-binding fragment thereof.

In some embodiments, at least two doses of MEDI4736 or an antigen-binding fragment thereof and tremelimumab or an antigen-binding fragment thereof are administered to the patient. In some embodiments, at least three doses, at least four doses, at least five doses, at least six doses, at least seven doses, at least eight doses, at least nine doses, at least ten doses, or at least fifteen doses or more can be administered to the patient. In some embodiments, MEDI4736 or an antigen-binding fragment thereof is administered over a four-week treatment period, over an eight-week treatment period, over a sixteen-week treatment period, over a twenty-week treatment period, over a twenty-four-week treatment period, or over a one-year or more treatment period. In some embodiments, tremelimumab or an antigen-binding fragment thereof is administered over a four-week treatment period, over an eight-week treatment period, over a twelve-week treatment period, over a sixteen-week treatment period, over a twenty-week treatment period, over a twenty-four-week treatment period, over a thirty-six-week treatment period, over a forty-eight-week treatment period, or over a one-year or more treatment period.

In some embodiments, MEDI4736 or an antigen-binding fragment thereof and tremelimumab or an antigen-binding fragment thereof are administered on the same day. In some embodiments, MEDI4736 or an antigen-binding fragment thereof is administered at the same time as tremelimumab or an antigen-binding fragment thereof. In other embodiments, MEDI4736 or an antigen-binding fragment thereof is administered about 1 hour following administration of tremelimumab or an antigen-binding fragment thereof.

The amount of MEDI4736 or an antigen-binding fragment thereof and the amount of tremelimumab or an antigen-binding fragment thereof to be administered to the patient will depend on various parameters such as the patient's age, weight, clinical assessment, tumor burden and/or other factors, including the judgment of the attending physician.

In certain aspects the patient is administered one or more doses of MEDI4736 or an antigen-binding fragment thereof wherein the dose is about 1 mg/kg. In certain aspects the patient is administered one or more doses of MEDI4736 or an antigen-binding fragment thereof wherein the dose is about 3 mg/kg. In certain aspects the patient is administered one or more doses of MEDI4736 or an antigen-binding fragment thereof wherein the dose is about 10 mg/kg. In certain aspects the patient is administered one or more doses of MEDI4736 or an antigen-binding fragment thereof wherein the dose is about 15 mg/kg. In certain aspects the patient is administered one or more doses of MEDI4736 or an antigen-binding fragment thereof wherein the dose is about 20 mg/kg.

In certain aspects the patient is administered at least two doses of MEDI4736 or an antigen-binding fragment thereof wherein the dose is about 1 mg/kg. In certain aspects the patient is administered at least two doses of MEDI4736 or an antigen-binding fragment thereof wherein the dose is about 3 mg/kg. In certain aspects the patient is administered at least two doses of MEDI4736 or an antigen-binding fragment thereof wherein the dose is about 10 mg/kg. In certain aspects the patient is administered at least two doses of MEDI4736 or an antigen-binding fragment thereof wherein the dose is about 15 mg/kg. In certain aspects the patient is administered at least two doses of MEDI4736 or an antigen-binding fragment thereof wherein the dose is about 20 mg/kg. In some embodiments, the at least two doses are administered about four weeks apart.

In certain aspects the patient is administered at least three doses of MEDI4736 or an antigen-binding fragment thereof wherein the dose is about 1 mg/kg. In certain aspects the patient is administered at least three doses of MEDI4736 or an antigen-binding fragment thereof wherein the dose is about 3 mg/kg. In certain aspects the patient is administered at least three doses of MEDI4736 or an antigen-binding fragment thereof wherein the dose is about 10 mg/kg. In certain aspects the patient is administered at least three doses of MEDI4736 or an antigen-binding fragment thereof wherein the dose is about 15 mg/kg. In certain aspects the patient is administered at least three doses of MEDI4736 or an antigen-binding fragment thereof wherein the dose is about 20 mg/kg. In some embodiments, the at least three doses are administered about four weeks apart.

In certain aspects the patient is administered one or more doses of tremelimumab or an antigen-binding fragment thereof wherein the dose is about 1 mg/kg. In certain aspects the patient is administered one or more doses of tremelimumab or an antigen-binding fragment thereof wherein the dose is about 3 mg/kg. In certain aspects the patient is administered one or more doses of tremelimumab or an antigen-binding fragment thereof wherein the dose is about 10 mg/kg.

In certain aspects the patient is administered at least two doses of tremelimumab or an antigen-binding fragment thereof wherein the dose is about 1 mg/kg. In certain aspects the patient is administered at least two doses of tremelimumab or an antigen-binding fragment thereof wherein the dose is about 3 mg/kg. In certain aspects the patient is administered at least two doses of tremelimumab or an antigen-binding fragment thereof wherein the dose is about 10 mg/kg. In some embodiments, the at least two doses are administered about four weeks apart. In some embodiments, the at least two doses are administered about twelve weeks apart.

In certain aspects the patient is administered at least three doses of tremelimumab or an antigen-binding fragment thereof wherein the dose is about 1 mg/kg. In certain aspects the patient is administered at least three doses of tremelimumab or an antigen-binding fragment thereof wherein the dose is about 3 mg/kg. In certain aspects the patient is administered at least three doses of tremelimumab or an antigen-binding fragment thereof wherein the dose is about 10 mg/kg. In some embodiments, the at least three doses are administered about four weeks apart. In some embodiments, the at least three doses are administered about twelve weeks apart.

In certain aspects, administration of MEDI4736 or an antigen-binding fragment thereof and/or tremelimumab or an antigen-binding fragment according to the methods provided herein is through parenteral administration. For example, MEDI4736 or an antigen-binding fragment thereof and/or tremelimumab or an antigen-binding fragment can be administered by intravenous infusion or by subcutaneous injection. In some embodiments, the administration is by intravenous infusion.

In certain aspects, 1 mg/kg of MEDI4736 or an antigen-binding fragment thereof and 1 mg/kg of tremelimumab or an antigen-binding fragment thereof are administered to a patient. In certain aspects, 1 mg/kg of MEDI4736 or an antigen-binding fragment thereof and 3 mg/kg of tremelimumab or an antigen-binding fragment thereof are administered to a patient. In certain aspects, 1 mg/kg of MEDI4736 or an antigen-binding fragment thereof and 10 mg/kg of tremelimumab or an antigen-binding fragment thereof are administered to a patient.

In certain aspects, 3 mg/kg of MEDI4736 or an antigen-binding fragment thereof and 1 mg/kg of tremelimumab or an antigen-binding fragment thereof are administered to a patient. In certain aspects, 3 mg/kg of MEDI4736 or an antigen-binding fragment thereof and 3 mg/kg of tremelimumab or an antigen-binding fragment thereof are administered to a patient. In certain aspects, 3 mg/kg of MEDI4736 or an antigen-binding fragment thereof and 10 mg/kg of tremelimumab or an antigen-binding fragment thereof are administered to a patient.

In certain aspects, 10 mg/kg of MEDI4736 or an antigen-binding fragment thereof and 1 mg/kg of tremelimumab or an antigen-binding fragment thereof are administered to a patient. In certain aspects, 10 mg/kg of MEDI4736 or an antigen-binding fragment thereof and 3 mg/kg of tremelimumab or an antigen-binding fragment thereof are administered to a patient. In certain aspects, 10 mg/kg of MEDI4736 or an antigen-binding fragment thereof and 10 mg/kg of tremelimumab or an antigen-binding fragment thereof are administered to a patient.

In certain aspects, 15 mg/kg of MEDI4736 or an antigen-binding fragment thereof and 1 mg/kg of tremelimumab or an antigen-binding fragment thereof are administered to a patient. In certain aspects, 15 mg/kg of MEDI4736 or an antigen-binding fragment thereof and 3 mg/kg of tremelimumab or an antigen-binding fragment thereof are administered to a patient. In certain aspects, 15 mg/kg of MEDI4736 or an antigen-binding fragment thereof and 10 mg/kg of tremelimumab or an antigen-binding fragment thereof are administered to a patient.

In certain aspects, 20 mg/kg of MEDI4736 or an antigen-binding fragment thereof and 1 mg/kg of tremelimumab or an antigen-binding fragment thereof are administered to a patient. In certain aspects, 20 mg/kg of MEDI4736 or an antigen-binding fragment thereof and 3 mg/kg of tremelimumab or an antigen-binding fragment thereof are administered to a patient. In certain aspects, 20 mg/kg of MEDI4736 or an antigen-binding fragment thereof and 10 mg/kg of tremelimumab or an antigen-binding fragment thereof are administered to a patient.

The methods provided herein can decrease, retard or stabilize tumor growth. In some aspects the reduction or retardation can be statistically significant. A reduction in tumor growth can be measured by comparison to the growth of patient's tumor at baseline, against an expected tumor growth, against an expected tumor growth based on a large patient population, or against the tumor growth of a control population. In certain aspects, a tumor response is measured using the Response Evaluation Criteria in Solid Tumors (RECIST).

In certain aspects, a tumor response is detectable at week 8. In certain aspects, a tumor response is detectable at week 33. In certain aspects, a tumor response is detectable at week 50.

In certain aspects, a tumor response is detectable after administration of administration of two doses of MEDI4736 or an antigen-binding fragment thereof and two doses of tremelimumab or an antigen-binding fragment thereof. In certain aspects, a tumor response is detectable after administration of administration of eight doses of MEDI4736 or an antigen-binding fragment thereof and seven doses of tremelimumab or an antigen-binding fragment thereof. In certain aspects, a tumor response is detectable after administration of administration of thirteen doses of MEDI4736 or an antigen-binding fragment thereof and nine doses of tremelimumab or an antigen-binding fragment thereof.

In certain aspects, a patient achieves disease control (DC). Disease control can be a complete response (CR), partial response (PR), or stable disease (SD).

A "complete response" (CR), a "partial response" (PR), and "stable disease" (SD) can be determined as defined in Table 1 below.

In certain aspects, administration of MEDI4736 or an antigen-binding fragment thereof can increase progression-free survival (PFS).

In certain aspects, administration of MEDI4736 or an antigen-binding fragment thereof can increase overall survival (OS).

In some embodiments, the patient has previously received treatment with at least one chemotherapeutic agent. In some embodiments, the patient has previously received treatment with at least two chemotherapeutic agents. The chemotherapeutic agent can be, for example, and without limitation, Vemurafenib, Erlotinib, Afatinib, Cetuximab, Carboplatin, Bevacizumab, Erlotinib, Gefitinib, and/or Pemetrexed.

In some embodiments, the NSCLC is refractory or resistant to at least one chemotherapeutic agent. In some embodiments, the tumor is refractory or resistant to at least two chemotherapeutic agents. The tumor can be refractory or resistant to one or more of, for example, and without limitation, Vemurafenib, Erlotinib, Afatinib, Cetuximab, Carboplatin, Bevacizumab, Erlotinib, Gefitinib, and/or Pemetrexed. In some embodiments, the NSCLC is negative for PD-L1. In some embodiments, the NSCLC is positive for PD-L1.

In some embodiments, the patient has an Eastern Cooperative Oncology Group (ECOG) (Oken M M, et al. *Am. J. Clin. Oncol.* 5: 649-55 (1982)) performance status of 0 or 1 prior to the administration of MEDI4736 or an antigen-binding fragment thereof and tremelimumab or an antigen-binding fragment thereof.

According to the methods provided herein, administration of MEDI4736 or an antigen-binding fragment thereof and tremelimumab or an antigen-binding fragment thereof can result in desirable pharmacokinetic parameters as shown in some early data. Total drug exposure can be estimated using the "area under the curve" (AUC). "AUC (tau)" refers to AUC from time 0 to time τ, the dosing interval, whereas "AUC (inf)" refers to the AUC until infinite time. The administration can produce AUC (tau) of about 600 to about 3,000 μg/mL*day of MEDI4736 or antigen-binding fragment thereof and about 250 to about 350 μg/mL*day of tremelimumab or antigen-binding fragment thereof. The administration can produce a maximum observed concentration (Cmax) of about 60 to about 300 μg/mL MEDI4736 or antigen-binding fragment thereof and of about 25 to about 35 μg/mL tremelimumab or antigen-binding fragment thereof. The administration can produce a C trough (minimum plasma drug concentration) of about 5 to about 40 μg/mL MEDI4736 or antigen-binding fragment thereof and about 4 to about 6 μg/mL tremelimumab or antigen-binding fragment thereof.

As provided herein, MEDI4736 or an antigen-binding fragment thereof can also decrease free (soluble) PD-L1 levels. Free (soluble) PD-L1 refers to PD-L1 that is not bound (e.g., by MEDI4736). In some embodiments, PD-L1 levels are reduced by at least 65%. In some embodiments, PD-L1 levels are reduced by at least 80%. In some embodiments, PD-L1 levels are reduced by at least 90%. In some embodiments, PD-L1 levels are reduced by at least 95%. In some embodiments, PD-L1 levels are reduced by at least 99%. In some embodiments, PD-L1 levels are not detectable following administration of MEDI4736 or an antigen-binding fragment thereof and tremelimumab or an antigen-binding fragment thereof.

In some embodiments, PD-L1 levels are reduced by at least 65% after a single administration of MEDI4736 or an antigen-binding fragment thereof. In some embodiments, PD-L1 levels are reduced by at least 80% after a single administration of MEDI4736 or an antigen-binding fragment thereof. In some embodiments, PD-L1 levels are reduced by at least 90% after a single administration of MEDI4736 or an antigen-binding fragment thereof. In some embodiments, PD-L1 levels are reduced by at least 95% after a single administration of MEDI4736 or an antigen-binding fragment thereof. In some embodiments, PD-L1 levels are reduced by at least 99% after a single administration of MEDI4736 or an antigen-binding fragment thereof. In some embodiments, PD-L1 levels are not detectable following a single administration of MEDI4736 or an antigen-binding fragment thereof.

In some embodiments, PD-L1 levels are reduced by at least 65% after administration of two doses of MEDI4736 or an antigen-binding fragment thereof. In some embodiments, PD-L1 levels are reduced by at least 80% after administration of two doses of MEDI4736 or an antigen-binding fragment thereof. In some embodiments, PD-L1 levels are reduced by at least 90% after administration of two doses of MEDI4736 or an antigen-binding fragment thereof. In some embodiments, PD-L1 levels are reduced by at least 95% after administration of two doses of MEDI4736 or an antigen-binding fragment thereof. In some embodiments, PD-L1 levels are reduced by at least 99% after administration of two doses of MEDI4736 or an antigen-binding fragment thereof. In some embodiments, PD-L1 levels are not detectable following administration of two doses of MEDI4736 or an antigen-binding fragment thereof.

Treatment of a patient with a solid tumor using both MEDI4736 or an antigen-binding fragment thereof and tremelimumab or an antigen-binding fragment thereof (i.e., co-therapy) as provided herein can result in an synergistic effect. As used herein, the term "synergistic" refers to a combination of therapies (e.g., a combination of MEDI4736 or an antigen-binding fragment thereof and tremelimumab or an antigen-binding fragment thereof) which is more effective than the additive effects of the single therapies.

A synergistic effect of a combination of therapies (e.g., a combination of a MEDI4736 or an antigen-binding fragment thereof and tremelimumab or an antigen-binding fragment thereof) permits the use of lower dosages of one or more of the therapeutic agents and/or less frequent administration of said therapeutic agents to a patient with a solid tumor. The ability to utilize lower dosages of therapeutic agents and/or to administer said therapies less frequently reduces the toxicity associated with the administration of said therapies to a subject without reducing the efficacy of said therapies in the treatment of a solid tumor. In addition, a synergistic effect can result in improved efficacy of therapeutic agents in the management, treatment, or amelioration of an solid tumor. The synergistic effect of a combination of therapeutic agents can avoid or reduce adverse or unwanted side effects associated with the use of either single therapy.

In co-therapy, MEDI4736 or an antigen-binding fragment thereof can be optionally included in the same pharmaceutical composition as the tremelimumab or an antigen-binding fragment thereof, or may be included in a separate pharmaceutical composition. In this latter case, the pharmaceutical composition comprising MEDI4736 or an antigen-binding fragment thereof is suitable for administration prior to, simultaneously with, or following administration of the pharmaceutical composition comprising tremelimumab or an antigen-binding fragment thereof. In certain instances, the MEDI4736 or an antigen-binding fragment thereof is administered at overlapping times as tremelimumab or an antigen-binding fragment thereof in a separate composition.

Subjects suffering from lung cancer (e.g., non-small cell lung cancer) may be tested for PD-L1 polynucleotide or polypeptide expression in the course of selecting a treatment method. Patients identified as having tumors that are negative for PD-L1 (e.g., as defined by Ct or IHC-M score) or by having reduced or undetectable levels of PD-L1 relative to a reference level are identified as responsive to treatment with a combination of an anti-PD-L1 antibody and tremelimumab. Such patients are administered an MEDI4736, or an antigen-binding fragment thereof in combination with tremelimumab or an antigen-binding fragment thereof.

EXAMPLES

Example 1

Patients and Methods (a) SUBJECTS

Subjects in this study are required to be 18 years of age or older and have histologically- or cytologically-confirmed non-small cell lung cancer (NSCLC; squamous and non-squamous), with at least one measurable lesion according to Response Evaluation Criteria in Solid Tumors (RECIST) guidelines v1.1, which is herein incorporated by reference in its entirety.

For both the dose-escalation and dose-expansion phases, cohort-specific prior immunotherapy requirements are as follows: a) immunotherapy-naïve cohort: must have no prior exposure to immunotherapy, such as, but not limited to, other anti-CTLA-4, anti-PD-1, or anti-PD-L1 antibodies excluding vaccines; and b) immunotherapy-pretreated cohort: must have had prior exposure to immunotherapy, such as, but not limited to, other anti-CTLA-4, anti-PD-1, or anti-PD-L1 antibodies excluding vaccines greater than 28 days prior to the first dose of MEDI4736 and tremelimumab.

The subjects are also required to have failed to respond to standard treatment, relapsed following standard treatment, declined standard treatment, or have not been eligible for standard treatment. Subjects will have an Eastern Cooperative Oncology Group (ECOG) performance status of 0-1.

Subjects with central nervous system (CNS) metastases must be asymptomatic at day 1 of the study. In addition, by day 1, there must be at least 28 weeks without progression of CNS metastases as evidenced by magnetic resonance imaging (MRI)/computed tomography (CT) after last day of treatment with radiation and at least 14 days since last dose of corticosteroids.

The subjects are also required to have adequate organ (hepatic and renal) and marrow function. Adequate organ and marrow function are defined as: hemoglobin≥9 g/dL; absolute neutrophil count≥1,500/mm$^3$; platelet count≥100,000/mm$^3$; total bilirubin≤1.5×upper limit of normal (ULN), unless associated with Gilbert's syndrome or liver metastasis (for these subjects, baseline total bilirubin must be ≤3.0 mg/dL); alanine aminotransferase (ALT) and aspartate aminotransferase (AST) must be ≤2.5×ULN unless associated with hepatic metastases (for these subjects, ALT and AST must be ≤5×ULN); and serum creatinine≤2.0 mg/dL.

Subjects are not able to participate if they are on any concurrent chemotherapy, immunotherapy, biologic, or hormonal therapy for cancer treatment. Subjects are not able to participate if they have taken any investigational anticancer therapy within 28 days prior to the first dose of MEDI4736 and tremelimumab. Subjects are not able to participate if they have any prior Grade ≥3 immune-related adverse event (irAE) while receiving immunotherapy, including anti-CTLA-4 treatment, or any unresolved irAE>Grade 1. Subjects are also not able to participate if they have undergone a major surgical procedure (as defined by the investigator) within 28 days prior to the first dose of MEDI4736 and tremelimumab or if they are still recovering from prior surgery. Subjects are also not able to participate if they have unresolved toxicities from prior anticancer therapy, defined as having not resolved to National Cancer Institute Common Terminology Criteria for Adverse Events (NCI CTCAE) v4.03 Grade 0 or 1 with the exception of alopecia and laboratory values listed per the inclusion criteria. Subjects with irreversible toxicity that is not reasonably expected to be exacerbated by MEDI4736 and tremelimumab may be included. Subjects are also excluded if they are currently using, or have used immunosuppressive medication within 14 days before the first dose of MEDI4736 and tremelimumab with the exceptions of intranasal and inhaled corticosteroids or systemic corticosteroids at physiologic doses not to exceed 10 mg/day of prednisone or equivalent.

Subjects are not able to participate if they have active or prior autoimmune disease, including inflammatory bowel disease, diverticulitis, irritable bowel disease, celiac disease, Wegener syndrome, and Hashimoto syndrome, within the past 3 years, except for vitiligo, alopecia, Grave's disease, or psoriasis not requiring systemic treatment (within the past 3 years). Subjects are also not able to participate if they have a history of primary immunodeficiency or tuberculosis, if they have known active or chronic viral hepatitis A, B, or C; if they have human immunodeficiency virus (HIV); other active serious illnesses or uncontrolled inter-current illnesses; have received live, attenuated vaccine within 28 days prior to the first dose of MEDI4736 and tremelimumab;

have other invasive malignancy within 5 years; or known allergy or hypersensitivity to study drug formulations.

Subjects are also not able to participate if they have advanced NSCLC with tumors harboring anaplastic lymphoma receptor tyrosine kinase (ALK) gene rearrangements or epidermal growth factor receptor (EGFR)-sensitizing mutations and have not received appropriate tyrosine kinase inhibitor (TKI) therapy. These subjects can be enrolled after documented progression or intolerance to appropriate TKIs.

(b) Design of the Study

Figure 1:
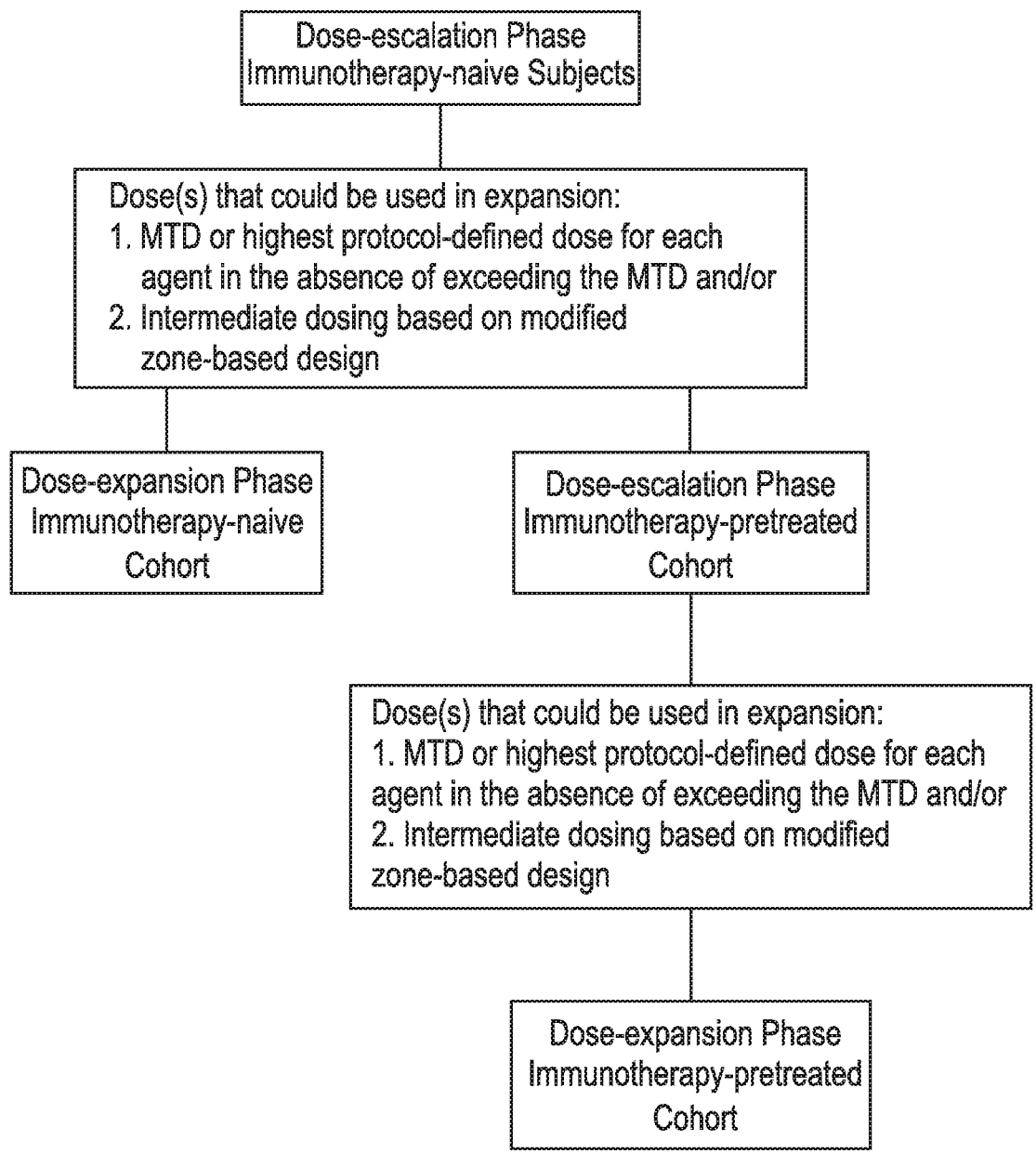
FIG. 1 shows the treatment schema. MTD=maximum tolerated dose.

The study is an open-label Phase 1b study of the combination of MEDI4736 and tremelimumab (FIG. 1). Key study criteria for cohorts is shown at FIG. 11. The study will enroll approximately 36 subjects in the dose escalation phase and in the dose-expansion phase and a minimum of 20 subjects each in immunotherapy-naïve and immunotherapy-pretreated cohorts. The maximum tolerated dose (MTD) or highest protocol-defined dose for each agent in the absence of exceeding the MTD determined for the immunotherapy-naïve cohort during the dose-escalation phase will serve as the starting dose for the subjects enrolled in the immunotherapy-pretreated cohort as part of the dose-escalation phase. Does exploration for the immunotherapy-pretreated cohort will be conducted in parallel with the dose-expansion phase for the immunotherapy-naïve cohort.

Dose-Escalation Phase

Immunotherapy-Naïve Cohort

Figure 2:
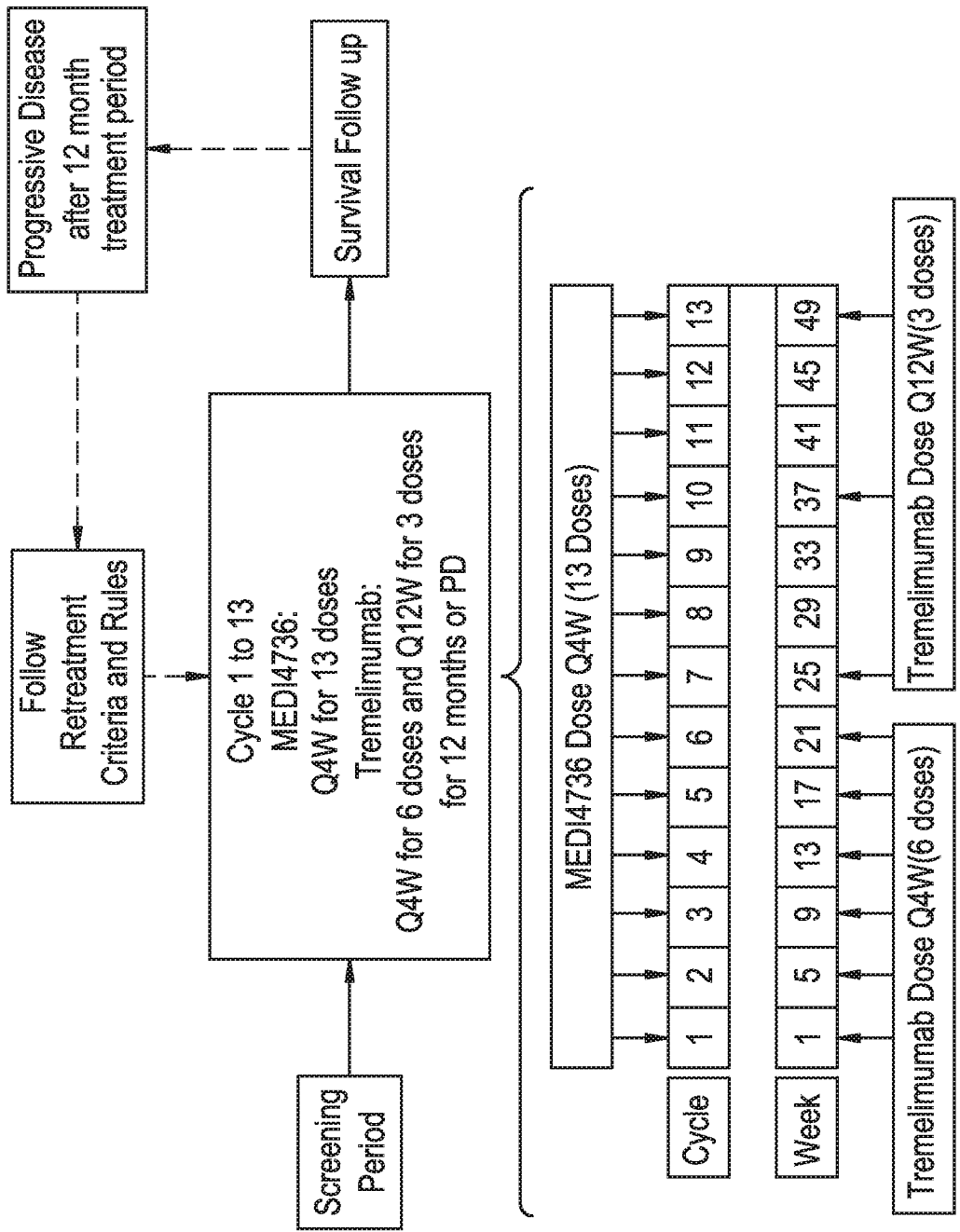
FIG. 2 shows the dose escalation and dose expansion schemas.

In the dose-escalation phase of the study, MEDI4736 and tremelimumab will be administered initially in sequential cohorts of 3-6 subjects who are immunotherapy-naïve with each subject receiving tremelimumab Q4W for 6 doses and every 12 weeks (Q12W) for 3 doses (i.e., tremelimumab Dose 7 given at 4 weeks from Dose 6 and Dose 8 given at 12 weeks from Dose 7) and MEDI4736 Q4W for 13 doses via IV infusion for a total of one year (FIG. 2). Each cohort will enroll a minimum of 3 subjects, according to a standard 3+3 design and a modified zone-based design. Subjects in the first cohort (Cohort 1) will receive a dose of 3 mg/kg MED4736 and 1 mg/kg of tremelimumab. If ≥2 dose limiting toxicities (DLTs) are observed in the first dose cohort, the starting dose will be de-escalated per FIG. 1. If no more than 1 out of 6 subjects experiences a DLT in a given dose cohort, dose-escalation will continue.

Subsequent cohorts will receive tremelimumab administered Q4W for 6 doses followed by Q12W for 3 doses and MEDI4736 administered Q4W for 13 doses until an MTD or the highest protocol-defined dose for each agent in the absence of exceeding the MTD is identified.

The expansion phase for the immunotherapy-naïve cohort (see FIG. 1) will begin once the MTD or highest protocol-defined dose for each agent in the absence of exceeding the MTD is determined in the immunotherapy-naïve subjects during the dose-escalation phase. Additional dose(s) from the intermediate zone-based cohort(s) that do not exceed the MTD can be evaluated in the expansion phase based on evaluation of PK and pharmacodynamics, safety and efficacy parameters in the immunotherapy-naïve cohort from the dose-expansion phase.

Immunotherapy-Pretreated Cohort

The MTD or highest protocol-defined dose for each agent in the absence of exceeding the MTD determined for the immunotherapy-naïve cohort (see FIG. 1) during the dose escalation phase will serve as the starting dose for subjects enrolled in the immunotherapy-pretreated cohort as part of the dose-escalation phase. The dose exploration for the immunotherapy-pretreated cohort using 3+3 design will be conducted in parallel with the dose-expansion phase for the immunotherapy-naïve cohort. The dose-expansion phase for the immunotherapy-pretreated cohort can begin once the MTD or highest protocol-defined dose for each agent in the absence of exceeding the MTD is determined in the immunotherapy-pretreated subjects during the dose-escalation phase. Additional dose(s) from the intermediate zone-based cohort(s) that do not exceed the MTD can be evaluated in the dose-expansion phase based on evaluation of PK and pharmacodynamics, safety and efficacy parameters in the immunotherapy-pretreated cohort from the dose-expansion phase.

Dose-Expansion Phase

Two dose-expansion cohorts will be used: immunotherapy-naïve and immunotherapy-pretreated (see FIG. 1). The MTD or highest protocol-defined dose for each agent in the absence of exceeding the MTD identified during the dose-escalation phase will be used for both cohorts in the dose-expansion phase. In addition, dose(s) from the intermediate zone-based cohort(s) that do not exceed the MTD can be included as an additional dose(s) for the immunotherapy-pretreated and immunotherapy-naïve cohorts in the dose-expansion phase based on emerging subject data, including safety, PK, pharmacodynamics, biomarker, and response as well as data present from ongoing trials.

Initially approximately 20 subjects with NSCLC will be enrolled in each of the immunotherapy-naïve cohort and the immunotherapy-pretreated cohort. Additional subjects, up to a total of 60 subjects each can be enrolled for the immunotherapy-naïve cohort in the dose-expansion phase dependent on emerging subject data, including safety, PK, pharmacodynamics, biomarker, and response as well as data present from ongoing trials.

Treatment Regimen

Subjects will be treated in either the dose-escalation or the dose-expansion phase of the study. In the dose-escalation and dose-expansion phases of the study, tremelimumab will be administered every four weeks (Q4W) for 6 doses followed by every twelve weeks (Q12W) for 3 doses in which Dose 7 is given 4 weeks after Dose 6 and Dose 8 is given 12 weeks after Dose 7. MEDI4736 will be administered Q4W for 13 doses. Both agents will be administered via IV infusion for a total of one year (FIG. 2).

Tremelimumab will be administered intravenously in 250 mL of 0.9% sodium chloride. MEDI4736 will be administered intravenously in 250 ml of 0.9% sodium chloride. Tremelimumab will be administered first. MEDI4736 infusion will start approximately 1 hour after the end of tremelimumab infusion. In Cohort 1, the first IV infusion of tremelimumab will be approximately 1 hour in duration and the first IV infusion of MEDI4736 will be approximately 4 hours in duration; subsequent infusions for subjects in this cohort and all infusions for the remaining cohorts will be approximately 1 hour in duration.

Subjects who achieve and maintain disease control (DC) (i.e., complete response (CR), partial response (PR), or stable disease (SD)) through to the end of the 12-month MEDI4736 and tremelimumab treatment period will enter follow-up. Upon evidence of progressive disease (PD) during follow-up, subjects may be re-administered MEDI4736 and tremelimumab for up to another 12 months with the same treatment guidelines followed during the initial 12-month period if the subject has not received other treatments for their disease and still meet inclusion and exclusion criteria for the study protocol. Only one round of retreatment with MEDI4736 and tremelimumab will be allowed.

Figure 3:
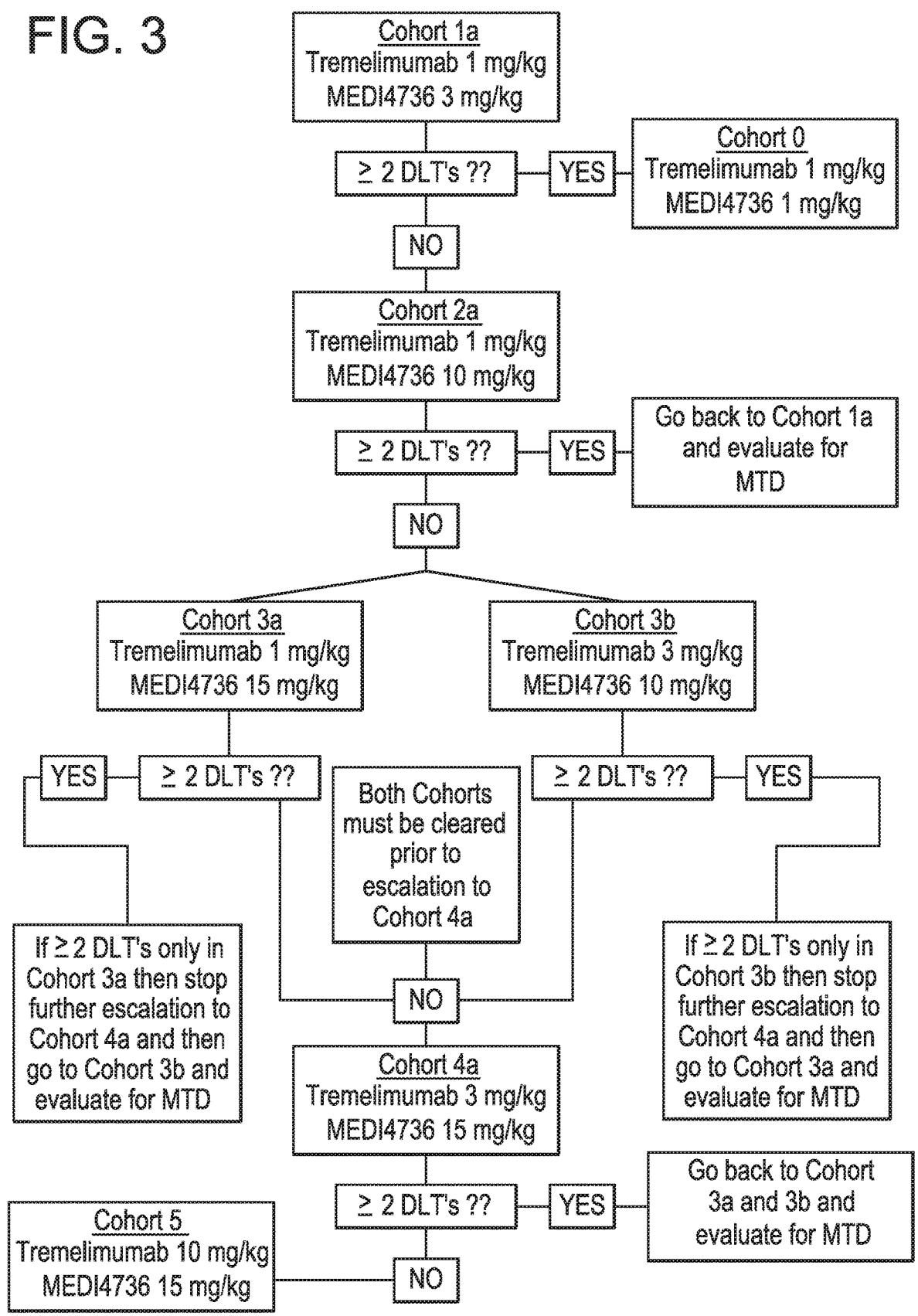
FIG. 3 shows the dose escalation study design. DLT=dose limiting toxicity.

The study utilizes a 3+3 dose-escalation phase and will follow the scheme depicted in FIG. 3. A minimum of three subjects will be enrolled in each dose cohort. If 0 out of the 3 patients in a dose cohort have a dose limiting toxicity (DLT), the next dose-escalation cohort will be started. If 1 out of the 3 patients has a DLT, an additional 3 patients will be enrolled in the same cohort. If no more than 1 of 6 subjects experiences a DLT, the next dose-escalation cohort will be started. If 2 or more patients in a dose cohort experience a DLT during the evaluation period, then no further subjects will be enrolled in that dose cohort.

The maximum tolerated dose (MTD) is defined as the highest dose of tremelimumab or MEDI4736 within a cohort where no more than 1 of 6 patients experiences a DLT. This is determined for both the immunotherapy-naïve and pretreated cohorts during the dose-escalation phase. Patients in the expansion phase (immunotherapy-naïve and immunotherapy-pretreated cohorts) will be treated at the MTD level determined in the dose-escalation phase.

MEDI4736 and tremelimumab administration can be modified or discontinued as a result of toxicities as described in FIGS. 10A and 10B. Dose modifications will not be required for adverse events (AEs) that are clearly not attributed to MEDI4736 or tremelimumab (such as an accident) or for laboratory abnormalities that are not deemed to be clinically significant.

(c) Phamacokinetic, Anti-Tumor, Biomarker, Soluble Factor, and Safety Assessments Measurement of MEDI4736 and tremelimumab concentrations in serum will be performed using a validated immunoassay.

Blood samples for pharmacokinetic assessment will be collected on the following days during the dose-escalation phase: day 1 (pre-dose and end of infusion), day 8 (±1 day), day 15 (±1 day), day 29 (pre-dose and end of infusion; ±3 days), day 57 (pre-dose and end of infusion; ±3 days), day 85 (pre-dose and end of infusion; ±3 days), day 113 (pre-dose and end of infusion; ±3 days), day 141 (pre-dose and end of infusion; ±3 days), day 169 (pre-dose and end of infusion; ±3 days), day 197 (pre-dose and end of infusion; ±3 days; MEDI4736 only), day 225 (pre-dose and end of infusion; ±3 days; MEDI4736 only), day 253 (pre-dose and end of infusion; ±3 days), day 281 (pre-dose and end of infusion; ±3 days; MEDI4736 only), day 309 (pre-dose and end of infusion; ±3 days), day 337 (pre-dose and end of infusion; ±3 days), at the end of treatment, 60 days after end of treatment, and 90 days after end of treatment.

Blood samples for pharmacokinetic assessment will be collected on the following days during the dose-expansion phase: day 1 (pre-dose and end of infusion), day 29 (±3 days), day 57 (±3 days), day 85 (±3 days), day 113 (±3 days), day 141 (±3 days), day 169 (±3 days); day 197 (±3 days; MEDI4736 only), day 225 (±3 days; MEDI4736 only), day 253 (±3 days), day 281 (±3 days; MEDI4736 only), day 309 (±3 days; MEDI4736 only), day 337 (±3 days), at the end of treatment, 60 days after end of treatment, and 90 days after end of treatment.

The presence of anti-drug antibodies (ADA) will be assessed on Day 1 and Days 29 (±3 days), 85 (±3 days), 141 (±3 days), 169 (±3 days), 253 (±3 days), and 337 (±3 days), at the end of treatment, 60 days after the end of treatment, and 90 days after the end of treatment. Validated electrochemiluminescence assays using a Meso Scale Discovery platform will be used for the determination of anti-MEDI4736 antibodies in human serum and for determination of anti-tremelimumab antibodies in human serum.

Blood samples will be collected for analysis of circulating soluble factors including soluble PD-L1 (sPD-L1). During the dose-escalation phase, levels of sPD-L1 will be assessed on day 1, day 8 (±1 day), day 15 (±1 day), day 29 (±3 days), day 57 (±3 days), day 85 (±3 days), day 113 (±3 days), day 141 (±3 days), day 169 (±3 days); day 197 (±3 days), day 225 (±3 days), day 253 (+3 days), day 281 (+3 days), day 309 (+3 days), day 337 (+3 days), at the end of treatment, 60 days after end of treatment, and 90 days after end of treatment. During the dose-expansion phase, levels of sPD-L1 will be assessed on day 1, day 29 (+3 days), day 57 (+3 days), day 85 (+3 days), day 113 (+3 days), day 141 (+3 days), day 169 (+3 days); day 197 (+3 days), day 225 (±3 days), day 253 (±3 days), day 281 (±3 days), day 309 (±3 days), day 337 (±3 days), at the end of treatment, 60 days after end of treatment, and 90 days after end of treatment.

Tumor assessments will be performed during screening (day −28 to day −1), at week 8 (day 50±3 days), and at week 33 (day 225±3 days) in the dose-escalation phase. Tumor assessments will be based on RECIST guidelines v1.1 with modifications and include the following evaluations: physical examination (with photograph and measurement of skin lesions as applicable), CT, or MRI scan of the chest, abdomen, and pelvis, and CT or MRI scan of the brain. Computed tomography or MRI scan of the brain is performed only at screening.

Assessments of anti-tumor activity are based on the measurement of tumor lesions, the evaluation of target lesions, the evaluation of non-target lesions, and the appearance of new lesions.

Target Lesion Evaluation

For the evaluation of target lesions, complete response is defined as the disappearance of all target lesions. Any pathological lymph nodes (whether target or non-target) must have reduction in short axis to <10 mm (the sum may not be "0" if there are target nodes).

For the evaluation of target lesions, partial response is defined as at least a 30% decrease in the sum of the diameters of target lesions, taking as reference the baseline sum diameters.

For the evaluation of target lesions, progressive disease is defined as at least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. The appearance of one or more new lesions is also considered progression.

For the evaluation of target lesions, stable disease (SD) is neither sufficient shrinkage to qualify for PR nor sufficient increase to qualify for PD, taking as reference the smallest sum of diameters while on study.

Non-Target Lesion Evaluation

For the evaluation of non-target lesions, complete response (CR) is defined as the disappearance of all non-target lesions. All lymph nodes must be <10 mm in short axis.

For the evaluation of non-target lesions, non-compete response/non-progressive disease is defined as the persistence of one more non-target lesions and/or maintenance of tumor marker level above the normal limits.

For the evaluation of non-target lesions, progressive disease is defined as the overall level of substantial worsening in non-target disease such that, even in presence of SD or PR in target disease, the overall tumor burden has increased sufficiently to merit discontinuation of therapy. In the absence of measurable disease, change in non-measurable disease comparable in magnitude to the increase that would be required to declare PD for measurable disease.

New Lesion

The appearance of new lesions is considered PD according to RECIST guidelines v1.1. Considering the unique response kinetics that have been observed with immunotherapy, new lesions may not represent true disease progression. In the absence of rapid clinical deterioration, subjects may continue to receive treatment with MEDI4736 and tremelimumab.

Overall Response

Confirmation of CR, PR, as well as PD is required by a repeat, consecutive assessment no less than 4 weeks from the date of first documentation. The evaluation of overall response based on target lesion, non-target lesion, and new lesion evaluation is determined as in Table 1 below.

TABLE 1

Evaluation of Overall Response

| Target Lesions | Non-target lesions | New Lesions | Overall Response |
|---|---|---|---|
| Complete Response | Complete Response | No | Complete Response |
| No target lesion[a] | Complete Response | No | Complete Response |
| Complete Response | Not evaluable[b] | No | Partial Response |
| Complete Response | Non-complete response/non-progressive disease | No | Partial Response |
| Partial Response | Non-progressive disease and not evaluable[b] | No | Partial Response |
| Stable Disease | Non-progressive disease and not evaluable[b] | No | Stable Disease |
| Not all evaluated | Non-progressive disease | No | Not evaluable |
| No target lesion[a] | Not all evaluated | No | Not evaluable |
| No target lesion[a] | Non-complete response/non-progressive disease | No | Non-complete response/non-progressive disease |
| Progressive Disease | Any | Yes or No | Progressive Disease |
| Any | Progressive Disease | Yes or No | Progressive Disease |
| Any | Any | Yes | Progressive Disease |
| No target lesion[a] | Unequivocal progressive disease | Yes or No | Progressive Disease |
| No target lesion[a] | Any | Yes | Progressive Disease |

[a]Defined as no target lesions at baseline.
[b]Not evaluable is defined as either when no or only a subset of lesion measurements are made at an assessment.

Adverse events are monitored following administration of MEDI4736. Other assessments include physical examination, vital sign monitoring, and laboratory measurements.

Example 2

Results (a) Enrollment and Follow-Up

Twelve subjects were treated with 3 subjects each in Cohort 1a (1 mg/kg tremelimumab and 3 mg/kg MEDI4736), Cohort 2a (1 mg/kg tremelimumab and 10 mg/kg MEDI4736), Cohort 3a (1 mg/kg tremelimumab and 15 mg/kg MEDI4736), and Cohort 3b (3 mg/kg tremelimumab and 10 mg/kg MEDI4736). Two subjects in Cohort 1a (one subject withdrew consent after 2 doses of both agents) completed approximately 115 days of follow-up; Cohort 2a subjects completed approximately 56 days of follow-up; and subjects in Cohorts 3a and 3b completed 28 days of follow up (FIG. 12).

(b) Pharmacokinetics

The pharmacokinetic data resulting from administration of MEDI4736 at 3 mg/kg and 10 mg/kg (in combination with 1 mg/kg tremelimumab) is summarized in FIG. 4. Individual PK parameters resulting from the administration of MEDI4736 are shown in FIG. 8. In this early data from first dose, the average Cmax for subjects receiving 3 mg/kg MEDI4736 was 67.36 µg/ml. The average AUCτ for subjects receiving 3 mg/kg MEDI4736 was 625.3 µg/ml*day. The average $C_{trough}$ for subjects receiving 3 mg/kg MEDI4736 was 8.85 µg/ml. The average Cmax for subjects receiving 10 mg/kg MEDI4736 was 266.7 µg/ml. The average AUCτ for subjects receiving 10 mg/kg MEDI4736 was 2860 µg/ml*day. The average $C_{trough}$ for subjects receiving 10 mg/kg MEDI4736 was 35.65 µg/ml. MEDI4736 exhibited a more than dose-proportional increase in AUC indicating non-linear PK. See FIG. 4.

The pharmacokinetic data resulting from administration of tremelimumab at 1 mg/kg (in combination with either 3 mg/kg MEDI4736 or 10 mg/kg MEDI4736) is summarized in FIG. 5. Individual PK parameters resulting from the administration of tremelimumab are shown in FIG. 9.

The average Cmax for subjects receiving 1 mg/kg tremelimumab in combination with 3 mg/kg MEDI4736 was 27.07 µg/ml. The average Cmax for subjects receiving 1 mg/kg tremelimumab in combination with 10 mg/kg MEDI4736 was 30.40 µg/ml.

The average AUCτ for subjects receiving 1 mg/kg tremelimumab in combination with 3 mg/kg MEDI4736 was 262.2 µg/ml*day. The average AUCτ for subjects receiving 1 mg/kg tremelimumab in combination with 10 mg/kg MEDI4736 was 338.8 µg/ml*day.

The average $C_{trough}$ for subjects receiving 1 mg/kg tremelimumab in combination with 3 mg/kg MEDI4736 was 4.21 µg/ml. The average $C_{trough}$ for subjects receiving 1 mg/kg tremelimumab in combination with 10 mg/kg MEDI4736 was 5.33 µg/ml.

(c) Soluble PD-L1 Assessment

The sPD-L1 data resulting from administration of MEDI4736 at 3 and 10 mg/kg and tremelimumab at 1 mg/kg is shown in FIG. 6 (absolute concentration), 7 and 8 (suppression, % of baseline). Following MEDI4736 administration, complete sPD-L1 suppression was observed in 5 of 6 subjects. In one subject, sPD-L1 suppression of approximately 65% was observed by the second dose of MEDI4736.

(d) Safety

Ten of twelve subjects reported a treatment-emergent adverse event (TEAE). The most frequently reported TEAEs were fatigue (41.7%; 5 subjects), increased amylase (25.0%; 3 subjects), pruritus and upper respiratory tract infection (16.7%; 2 subjects each). No subject experienced a dose-limiting toxicity. Nine of ten subjects who experienced TEAEs had events that were Grade 1 or 2 in severity. One subject (Cohort 2a) experienced Grade 3 increased aspartate aminotransferase (AST) and increased alanine aminotransferase (ALT) and a fatal (Grade 5) myasthenia gravis. Two of the twelve subjects experienced treatment-emergent serious adverse events (SAEs). Two subjects discontinued treatment due to TEAEs. FIG. 13 shows related adverse events.

Early results showing change of tumor size from baseline are shown in FIG. 14. Reductions in tumor size were seen in patients in the 1 mg/kg (T)+10 mg/kg (M), 1 mg/kg (T)+15 mg/kg (M) and 3 mg/kg (T)+10 mg/kg (M) groups.

This study demonstrates that MEDI4736 and tremelimumab have favorable pharmacokinetic properties and the combination of agents suppresses sPD-L1. In addition, MEDI4736 is well tolerated in most of the subjects currently being treated.

Example 3

Phase 1b, Open-Label Study of MEDI4736 in Combination With Tremelimumab in Patients With Advanced NSCLC The inhibitory PD-L1 and CTLA-4 pathways play a major role in controlling T cell activation. MEDI4736 (M) is a human IgG1 monoclonal antibody that blocks PD-L1 binding to PD-1 and CD-80. Tremelimumab (T) is a human IgG2 monoclonal antibody targeting CTLA-4. Both MEDI4736 and Tremelimumab have demonstrated encouraging safety profiles and promising clinical activity as single agents; as they block distinct interactions contributing to immunosuppression, combination MEDI4736+ Tremelimumab therapy may provide greater antitumor activity compared with either agent alone in patients (pts) with advanced non-small cell lung cancer.

This Phase 1 study is assessing the safety/tolerability, antitumor activity, pharmacokinetics (PK) and immunogenicity of MEDI4736+Tremelimumab combination therapy in patients with advanced NSCLC. The study has dose-escalation and -expansion phases.

Results: As of Dec. 4, 2014, 61 patients have been treated (Table 2).

TABLE 2

| Cohort | Dose |
|---|---|
| 1a | 3 mg/kg M q4w + 1 mg/kg T |
| 2a | 10 mg/kg M q4w + 1 mg/kg T |
| 3a | 15 mg/kg M q4w + 1 mg/kg T |
| 3b | 10 mg/kg M q4w + 3 mg/kg T |
| 4 | 20 mg/kg M q4w + 1 mg/kg T |
| 4a | 15 mg/kg M q4w + 3 mg/kg T |
| 5 | 15 mg/kg M q4w + 10 mg/kg T |
| 5a | 20 mg/kg M q4w + 3 mg/kg T |
| 6 | 20 mg/kg M q4w + 10 mg/kg T |
| 8 | 10 mg/kg M q2w + 1 mg/kg T |
| 9 | 10 mg/kg M q2w + 3 mg/kg T |
| 10 | 10 mg/kg M q2w + 10 mg/kg T |

MEDI4736 (M) + Tremelimumab (T)
Q4W = every 4 weeks;
Q2W = every 2 weeks

Overall, the most frequent drug-related AEs for all grades ($\geq$10% pts) were diarrhea, fatigue, pruritis, increased alanine transaminase (ALT) and amylase; that were manageable with standard treatment guidelines including steroids. The most frequent $\geq$Grade 3 drug-related AEs ($\geq$5%) across all patients were colitis, diarrhea, increased aspartate aminotransferase (AST) and ALT. Drug-related AEs leading to discontinuation were colitis (6.6%), diarrhea (3.3%), pneumonitis (3.3%), increased AST (3.3%) and ALT (1.6%), cough (1.6%) and dyspnea (1.6%); there was 1 treatment-related death (polymyositis) in the 10 mg/kg M q4w+1 mg/kg T cohort. Of 31 subjects with at least one 8 week scan, the best overall response was reported in 8 patients (26%); stable disease was reported in 11 pts (36%).

These promising results indicate that the MEDI4736+ Tremelimumab combination has a manageable safety profile and early clinical activity.

Results: As of Jan. 27, 2015, 74 patients across 10 cohorts have been treated (Table 3).

TABLE 3

Demographics and Baseline Characteristics

| Characteristic | | 1a<br>T 1 mg/kg<br>M 3 mg/kg Q4W<br>(N = 3) | 2a<br>T 1 mg/kg<br>M 10 mg/kg Q4W<br>(N = 3) | 3a<br>T 1 mg/kg<br>M 15 mg/kg<br>Q4W<br>(N = 18) | 3b<br>T 3 mg/kg<br>M 10 mg/kg Q4W<br>(N = 3) | 4<br>T 1 mg/kg<br>M 20 mg/kg<br>Q4W<br>(N = 18) |
|---|---|---|---|---|---|---|
| Age (years) | n | 3 | 3 | 18 | 3 | 18 |
| | Mean | 73.7 | 67.3 | 66.2 | 63.7 | 64.2 |
| | SD | 3.8 | 3.5 | 7.1 | 16.7 | 7.7 |
| | Median | 72.0 | 67.0 | 66.5 | 54.0 | 66.0 |
| | (Min, Max) | (71, 78) | (64, 71) | (53, 78) | (54, 83) | (49, 78) |
| Sex | Male | 1 (33.3%) | 2 (66.7%) | 9 (50.0%) | 1 (33.3%) | 10 (55.6%) |
| | Female | 2 (66.7%) | 1 (33.3%) | 9 (50.0%) | 2 (66.7%) | 8 (44.4%) |
| Baseline ECOG Status | 0 | 0 (0.0%) | 2 (66.7%) | 5 (27.8%) | 2 (66.7%) | 5 (27.8%) |
| | 1 | 3 (100%) | 1 (33.3%) | 13 (72.2%) | 1 (33.3%) | 13 (72.2%) |
| Histology | Squamous | 1 (33.3%) | 0 (0.0%) | 1 (5.6%) | 0 (0.0%) | 1 (6.7%) |
| | Non-Squamous | 2 (66.7%) | 3 (100%) | 17 (94.4%) | 3 (100%) | 14 (93.3%) |
| | MISSING | 0 | 0 | 0 | 0 | 3 |
| Time since Initial Diagnosis to Study Treatment (Months) | n | 3 | 3 | 16 | 3 | 16 |
| | Mean | 19.67 | 35.23 | 29.36 | 13.90 | 18.98 |
| | SD | 13.27 | 8.71 | 32.20 | 10.57 | 14.74 |
| | Median | 16.60 | 32.00 | 15.40 | 11.40 | 16.55 |
| | (Min, Max) | (8.2, 34.2) | (28.6, 45.1) | (4.0, 127.8) | (4.8, 25.5) | (2.8, 68.2) |
| Mutation Status | EGFR | 0 (0.0%) | 0 (0.0%) | 2 (11.1%) | 0 (0.0%) | 2 (13.3%) |
| | ALK | 0 (0.0%) | 0 (0.0%) | 0 (0.0%) | 0 (0.0%) | 0 (0.0%) |
| | KRAS | 1 (33.3%) | 1 (33.3%) | 1 (5.6%) | 0 (0.0%) | 1 (6.7%) |
| | No Mutation | 0 (0.0%) | 2 (66.7%) | 14 (77.8%) | 3 (100%) | 12 (80.0%) |
| | Other | 0 (0.0%) | 0 (0.0%) | 1 (5.6%) | 0 (0.0%) | 0 (0.0%) |
| | Unknown | 2 (66.7%) | 0 (0.0%) | 0 (0.0%) | 0 (0.0%) | 0 (0.0%) |
| | MISSING | 0 | 0 | 0 | 0 | 3 |

TABLE 3-continued

Demographics and Baseline Characteristics

| | | | | | | |
|---|---|---|---|---|---|---|
| Smoking History | Never Smoked | 1 (33.3%) | 0 (0.0%) | 3 (16.7%) | 1 (33.3%) | 0 (0.0%) |
| | Former/Current Smoker | 2 (66.7%) | 3 (100%) | 15 (83.3%) | 2 (66.7%) | 18 (100%) |
| Number of Prior Systemic Regimens | 1 | 1 (33.3%) | 0 (0.0%) | 4 (22.2%) | 3 (100%) | 4 (22.2%) |
| | 2 | 0 (0.0%) | 0 (0.0%) | 8 (44.4%) | 0 (0.0%) | 6 (33.3%) |
| | 3 | 2 (66.7%) | 2 (66.7%) | 4 (22.2%) | 0 (0.0%) | 5 (27.8%) |

| Characteristic | | 4a<br>T 3 mg/kg<br>M 15 mg/kg<br>Q4W<br>(N = 14) | 5<br>T 10 mg/kg<br>M 15 mg/kg<br>Q4W<br>(N = 9) | 5a<br>T 3 mg/kg<br>M 20 mg/kg<br>Q4W<br>(N = 6) | 8<br>T 1 mg/kg<br>M 10 mg/kg<br>Q2W<br>(N = 14) | 9<br>T 3 mg/kg<br>M 10 mg/kg<br>Q2W<br>(N = 11) |
|---|---|---|---|---|---|---|
| Age (years) | n | 14 | 9 | 6 | 14 | 11 |
| | Mean | 68.6 | 63.7 | 67.2 | 66.6 | 57.3 |
| | SD | 4.5 | 7.3 | 10.1 | 10.7 | 16.5 |
| | Median | 69.0 | 65.0 | 70.0 | 70.5 | 63.0 |
| | (Min, Max) | (59, 76) | (54, 77) | (50, 78) | (42, 77) | (22, 86) |
| Sex | Male | 10 (71.4%) | 4 (44.4%) | 3 (50.0%) | 7 (50.0%) | 8 (72.7%) |
| | Female | 4 (28.6%) | 5 (55.6%) | 3 (50.0%) | 7 (50.0%) | 3 (27.3%) |
| Baseline ECOG Status | 0 | 6 (42.9%) | 1 (11.1%) | 1 (16.7%) | 8 (57.1%) | 1 (9.1%) |
| | 1 | 8 (57.1%) | 8 (88.9%) | 5 (83.3%) | 6 (42.9%) | 10 (90.9%) |
| Histology | Squamous | 1 (7.1%) | 0 (0.0%) | 0 (0.0%) | 3 (21.4%) | 1 (9.1%) |
| | Non-Squamous | 13 (92.9%) | 9 (100%) | 6 (100%) | 11 (78.6%) | 10 (90.9%) |
| | MISSING | 0 | 0 | 0 | 0 | 0 |
| Time since Initial Diagnosis to Study Treatment (Months) | n | 13 | 9 | 6 | 11 | 11 |
| | Mean | 20.72 | 26.89 | 38.88 | 18.25 | 24.16 |
| | SD | 17.02 | 23.84 | 44.96 | 10.24 | 25.64 |
| | Median | 14.10 | 19.70 | 23.10 | 17.40 | 15.10 |
| | (Min, Max) | (1.0, 53.3) | (3.9, 81.7) | (10.1, 128.2) | (3.4, 37.7) | (2.9, 82.9) |
| Mutation Status | EGFR | 0 (0.0%) | 2 (22.2%) | 1 (16.7%) | 3 (21.4%) | 1 (9.1%) |
| | ALK | 0 (0.0%) | 0 (0.0%) | 0 (0.0%) | 0 (0.0%) | 1 (9.1%) |
| | KRAS | 2 (14.3%) | 3 (33.3%) | 2 (33.3%) | 2 (14.3%) | 4 (36.4%) |
| | No Mutation | 8 (57.1%) | 3 (33.3%) | 3 (50.0%) | 6 (42.9%) | 5 (45.5%) |
| | Other | 1 (7.1%) | 1 (11.1%) | 0 (0.0%) | 0 (0.0%) | 0 (0.0%) |
| | Unknown | 3 (21.4%) | 0 (0.0%) | 0 (0.0%) | 3 (21.4%) | 0 (0.0%) |
| | MISSING | 0 | 0 | 0 | 0 | 0 |
| Smoking History | Never Smoked | 2 (14.3%) | 1 (11.1%) | 2 (33.3%) | 5 (35.7%) | 3 (27.3%) |
| | Former/Current Smoker | 12 (85.7%) | 8 (88.9%) | 4 (66.7%) | 9 (64.3%) | 8 (72.7%) |
| Number of Prior Systemic Regimens | 1 | 4 (30.8%) | 1 (11.1%) | 1 (16.7%) | 1 (7.1%) | 3 (27.3%) |
| | 2 | 2 (15.4%) | 2 (22.2%) | 0 (0.0%) | 4 (28.6%) | 5 (45.5%) |
| | 3 | 2 (15.4%) | 1 (11.1%) | 4 (66.7%) | 4 (28.6%) | 0 (0.0%) |

| Characteristic | | | TOTAL<br>(N = 99) |
|---|---|---|---|
| Age (years) | | n | 99 |
| | | Mean | 65.2 |
| | | SD | 9.6 |
| | | Median | 67.0 |
| | | (Min, Max) | (22, 86) |
| Sex | | Male | 55 (55.6%) |
| | | Female | 44 (44.4%) |
| Baseline ECOG Status | | 0 | 31 (31.3%) |
| | | 1 | 68 (68.7%) |
| Histology | | Squamous | 8 (8.3%) |
| | | Non-Squamous | 88 (91.7%) |
| | | MISSING | 3 |
| Time since Initial Diagnosis to Study Treatment (Months) | | n | 91 |
| | | Mean | 24.08 |
| | | SD | 23.29 |
| | | Median | 16.80 |
| | | (Min, Max) | (1.0, 128.2) |
| Mutation Status | | EGFR | 11 (11.5%) |
| | | ALK | 1 (1.0%) |
| | | KRAS | 17 (17.7%) |
| | | No Mutation | 56 (58.3%) |
| | | Other | 3 (3.1%) |
| | | Unknown | 8 (8.3%) |
| | | MISSING | 3 |
| Smoking History | | Never Smoked | 18 (18.2%) |
| | | Former/Current Smoker | 81 (81.8%) |
| Number of Prior Systemic Regimens | | 1 | 22 (22.4%) |
| | | 2 | 27 (27.6%) |
| | | 3 | 24 (24.5%) |

Various doses and schedules of MEDI4736 and tremelimumab administered in combination were examined (FIG. 15). MEDI4736 doses and scheduling included 3 mg/kg, 10 mg/kg, 15 mg/kg, and 20 mg/kg every 4 weeks (q4w) and 10 mg/kg every 2 weeks (q2w). Tremelimumab doses and scheduling included 1 mg/kg, 3 mg/kg, and 10 mg/kg every 4 weeks (q4w×6 doses) and every 12 weeks (q12w×3 doses).

Complete sPD-L1 suppression at doses ≥15 mg/kg Q4W MEDI4736 was observed (FIG. 16). One subject each at 10 mg/kg Q4W and 15 mg/kg Q4W showed partial sPD-L1 suppression at some visits followed by complete suppression after repeated dosing. One subject following 15 mg/kg Q4W was not suppressed at Day 29. By comparison, complete suppression was observed with single-agent MEDI4736 (Study 1108) at doses >3 mg/kg Q2W. When individual sPD-L1 profiles by cohort were examined, complete sPD-L1 suppression was observed in >95% of subjects following 10 mg/kg Q2W dose (FIG. 17).

Increased proliferation of T cells was also observed when MEDI4736 and tremelimumab were administered in combination (FIG. 18). Cells were sorted by FACS analysis for the markers CD4 and CD8 in combination with Ki67, a marker of cell proliferation. A monotonic increase in peak CD4+Ki67+ cells was observed with increasing tremelimumab dose, which was greater than the increase in peak CD4+Ki67+ observed with MEDI4736 alone. The CD8+ proliferative response was greater with combinations of MEDI4736 and tremelimumab than with MEDI4736 alone.

Increases in CD4 ICOS+ and CD4 HLADR+ cells was observed in subjects receiving MEDI4736 and tremelimumab compared to MEDI4736 alone (FIG. 19). Minimal changes in CD4+ICOS+ cells and CD4+HLADR+ cells was observed with MEDI4736 alone and all tested combination doses had a pattern distinguishable from MEDI4736. Maximal increases in CD4+ICOS+ cells and CD4+HLADR+ cells were observed with a 10 mg/kg tremelimumab dose. Increase in CD4+T effector cells and Treg cells (CD25hi CD12710 phenotype may also include some activated T cells) were also observed in subjects receiving MEDI4736 and tremelimumab compared to MEDI4736 alone (FIGS. 20 and 21).

Clinical activity in NSCLC was observed with treatment with MEDI4736 and tremelimumab (all doses) showed increases in overall response rate, compared to treatment with MEDI4736 monotherapy (10 mg/kg Q2W (FIG. 22). Response was evaluable in treated patients with measurable disease at baseline +≥1 follow-up scan (includes discontinuations due to disease progression or death prior to first follow-up scan). For MEDI4736 NSCLC (CP1108), only patients with ≥12 weeks follow-up were included. Overall response rate (ORR) includes confirmed and unconfirmed complete response (CR) or partial response (PR). For MEDI4736 NSCLC monotherapy (CP1108, 10 mg/kg Q2W), best overall response (BOR) of stable disease (SD) with minimum duration of 12 weeks is presented. For the combination of MEDI4736 and tremelimumab, BOR of SD with minimum duration of 7 weeks is presented.

Decreases in or stabilization of tumor size was seen in the majority of NSCLC patients administered MEDI4736 and tremelimumab at tremelimumab doses of 1 mg/kg; 3 mg/kg; and 10 mg/kg (FIG. 23). The onset of grade 3 adverse events showed that increasing the dosage of tremelimumab also decreased the time of onset of an adverse event (FIG. 24). Decreases in or stabilization of tumor size was seen in the majority of NSCLC patients administered MEDI4736 and tremelimumab at MEDI4736 doses of 10 mg/kg; 315 mg/kg; and 20 mg/kg at Q4W or 10 mg/kg at Q2W (FIG. 25). The onset of grade 3 adverse events showed that increasing the dosage of tremelimumab affected the time of onset of an adverse event than increasing the dosage of MEDI4736 (FIG. 26). Thus, selection of MEDI4736 and tremelimumab dosages will take into account efficacy and safety.

Exposure data from single-agent tremelimumab in cancer therapy has supported that higher exposures (>30 mg/mL) are needed to maximize efficacy. These levels are attained, on average, at doses ≥3 mg/kg. The exposure achieved following tremelimumab at 1 mg/kg is expected to produce less toxicity than 3 mg/kg based on an analysis of single-agent exposure-safety relationships. Without being bound to a particular theory, tremelimumab at 1 mg/kg partially inhibits CTLA4, as immune-mediated adverse effects are still observed at 1 mg/kg (albeit at lower incidence). Tremelimumab at 1 mg/kg could be optimal in combination with MEDI4736 if synergistic efficacy is observed and the safety profile is improved relative to higher tremelimumab doses.

In one study, complete suppression of the PD-L1 sink and sPD-L1 in serum was observed at doses ≥3 mg/kg Q2W MEDI4736. A dose of 10 mg/kg Q2W was chosen for use as a single agent based on achieving >99% saturation of the sink in the majority of subjects, with drug levels producing maximum tumor growth inhibition (TGI) in mouse models (100 mg/mL identified as the minimum target trough concentration). Following 10 mg/kg Q4W in combination with tremelimumab, suppression of sPD-L1 was observed in some subjects. Dose density was higher with MEDI4736 Q2W and Cmax was higher with Q4W. Scheduling with Q4W may provide greater convenience. In other subjects, incomplete suppression was observed, possibly due to upregulation of PD-L1 combined with suboptimal trough levels achieved at this dose level. MEDI4736 at 10 mg/kg Q4W, evaluated in combination with tremelimumab, produced trough concentrations below the target of 100 mg/mL. However, target levels were achieved with MEDI4736 at 15 and 20 mg/kg Q4W, and the higher doses of MEDI4736 maintained sPD-L1 suppression in all subjects evaluated to date. MEDI4736 at 10 mg/kg or higher could be optimal in combination with tremelimumab if synergistic efficacy is observed and the safety profile is improved.

Overall, the trend for the combination of MEDI4736 and tremelimumab was to decrease or stabilize disease compared to MEDI4736 monotherapy, and MEDI4736 and tremelimumab at the highest doses tested was associated with increased incidence of adverse events. (FIGS. 27-29). These results indicate that the a combination of MEDI4736 and tremelimumab is well-tolerated and has the potential to be an effective therapy for NSCLC.

Example 4

Treatment of PD-L1 Negative Tumors in NSCLC With MEDI4736 and Tremelimumab

Twelve subjects were treated, with 3 subjects each in Cohort 1a (1 mg/kg tremelimumab and 3 mg/kg MEDI4736), Cohort 2a (1 mg/kg tremelimumab and 10 mg/kg MEDI4736), Cohort 3a (1 mg/kg tremelimumab and 15 mg/kg MEDI4736), and Cohort 3b (3 mg/kg tremelimumab and 10 mg/kg MEDI4736). Two subjects in Cohort 1a (one subject withdrew consent after 2 doses of both agents) completed approximately 115 days of follow-up; Cohort 2a subjects completed approximately 56 days of follow-up; and subjects in Cohorts 3a and 3b completed 28 days of follow up.

Baseline levels of PD-L1 tumor expression data for 7 subjects on the study are provided at Table 4 (below). Additional information is provided at Table 5.

| Cohort | M Score | PD-L1 Result (@25% M Score) | BOR (cut-off Jun. 4, 2014) | Best Change in target Lesion |
|---|---|---|---|---|
| Cohort 5 (15 MEDI4736/ 10 Treme) | 13 | NEG | No Assessments | NA |
| Cohort 3a (15 MEDI4736/ 1 Treme) | 0 | NEG | Unconfirmed PR | 65.2% Decrease |
| Cohort 2a (10 MEDI4736/ 1 Treme) | 0 | NEG | PD | 3.7% Increase |
| Cohort 2a (10 MEDI4736/ 1 Treme) | 7 | NEG | SD | 1.6% Increase |
| Cohort 3a (15 MEDI4736/ 1 Treme) | 2 | NEG | SD | 26.7% Decrease |
| Cohort 3b (10 MEDI4736/ 3 Treme) | 2 | NEG | Unconfirmed PR | 38.9% Decrease |
| Cohort 3b (10 MEDI4736/ 3 Treme) | 0 | NEG | PD | 23.5% Increase |

TABLE 5

| Cohort | SID | 3+ Tumor Membrane | 2+ Tumor Membrane | 1+ Tumor Membrane | M Score | PD-L1 Result (@25% M Score Cutoff) | REC'D | COLLECTION DATE |
|---|---|---|---|---|---|---|---|---|
| Cohort 5 (15 MEDI4736/10 Treme) | 2000060020 | 0 | 8 | 5 | 13 | NEG | 16-Jun-14 | 08Apr14 |
| Cohort 3a (15 MEDI4736/1 Treme) | 2000060009 | 0 | 0 | 0 | 0 | NEG | 16-Jun-14 | 08Jan14 |
| Cohort 2a (10 MEDI4736/1 Treme) | 2000060004 | 0 | 0 | 0 | 0 | NEG | 16-Jun-14 | 25May12 |
| Cohort 2a (10 MEDI4736/1 Treme) | 2000062007 | 0 | 5 | 2 | 7 | NEG | 16-Jun-14 | 31Aug11 |
| Cohort 3a (15 MEDI4736/1 Treme) | 2000060014 | 0 | 2 | 0 | 2 | NEG | 16-Jun-14 | 12Jun07 |
| Cohort 3b (10 MEDI4736/3 Treme) | 2000062015 | 0 | 1 | 1 | 2 | NEG | 16-Jun-14 | 04Oct13 |
| Cohort 3b (10 MEDI4736/3 Treme) | 2000060010 | 0 | 0 | 0 | 0 | NEG | 16-Jun-14 | 01Aug13 |

| Cohort | SID | BOR (cut-off Jun. 4, 2014) | Best Change in target Lesion | Current Status |
|---|---|---|---|---|
| Cohort 5 (15 MEDI4736/10 Treme) | 2000060020 | No Assessments | NA | On treatment. Waiting for week 8 scans |
| Cohort 3a (15 MEDI4736/1 Treme) | 2000060009 | Unconfirmed PR | 65.2% Decrease | On treatment. Waiting for week 16 scans |
| Cohort 2a (10 MEDI4736/1 Treme) | 2000060004 | PD | 3.7% Increase | On treatment past progression at week 20. |
| Cohort 2a (10 MEDI4736/1 Treme) | 2000062007 | SD | 1.6% Increase | On treatment at week 20. |
| Cohort 3a (15 MEDI4736/1 Treme) | 2000060014 | SD | 26.7% Decrease | Off treatment at 8 weeks (colitis) |
| Cohort 3b (10 MEDI4736/3 Treme) | 2000062015 | Unconfirmed PR | 38.9% Decrease | On treatment at 12 weeks. |
| Cohort 3b (10 MEDI4736/3 Treme) | 2000060010 | PD | 23.5% Increase | Off treatment at 8 weeks (colitis, PD) |

Subject tissue of NSCLC patients was characterized for PD-L1 expression by immunohistochemistry in formalin fixed and paraffin embedded tissue samples. A sample was determined to be "PD-L1 positive" if the sample contained 25% or more tumor cells with PD-L1 membrane staining. This is expressed as immunohistochemistry membrane (M)-score. All samples were scored as "negative" for PD-L1 expression. Tumor assessments are available on 6 of 7 patients. Three patients treated with a combination of tremelimumab and MEDI4736.

Two patients were identified as unconfirmed partial responders (PR), two had stable disease (SD), and two had progressive disease (PD). In all 6 patients, tumor samples were collected >6 months prior to analysis for PD-L1 expression, and 3 of 6 biopsy samples were collected more than 2 years prior to analysis. These data indicate that a combination of MEDI4736 and tremelimumab is active in PD-L1 negative NSCLC based on stored tissue samples.

When administered MEDI4736 and tremelimumab, most patients having PD-L1 negative NSCLC responded to combination therapy, and showed decreases in or stabilization of tumor size, compared to MEDI4736 monotherapy (CP1108, 10 mg/kg Q2W) (FIG. 30). Patients having PD-L1 positive NSCLC also responded to the combination of MEDI4736 and tremelimumab compared to MEDI4736 monotherapy, and showed decreases in or stabilization of tumor size (FIG. 31). When the results of the patients having PD-L1 negative NSCLC were grouped by the dose of tremelimumab, 1 mg/kg tremelimumab or 3 mg/kg tremelimumab administered in combination with MEDI4736 at 10 mg/kg Q4W or 15 mg/kg Q4W were effective at controlling or reducing disease (FIG. 32). When the results were grouped by the dose of MEDI4736, the results also showed that tremelimumab at 1 mg/kg to 3 mg/kg administered in combination with MEDI4736 at 10 mg/kg Q4W to 15 mg/kg Q4W was effective at controlling or reducing disease (FIG. 33). Analysis of all NSCLC patients receiving MEDI4736 and tremelimumab showed that PD-L1- and PD-L1+ NSCLC patients responded to treatment (FIGS. 34A-34D and 35-37; Tables 6-9).

TABLE 6

Best Overall Response - All Evaluable Subjects
Response Evaluable Population

| | MEDI4736 (M) and Tremelimumab (T) Cohort | | | | | | |
|---|---|---|---|---|---|---|---|
| | 1a<br>3 mg/kg (M) +<br>1 mg/kg (T)<br>Q4W<br>N = 3 | 2a<br>10 mg/kg (M) +<br>1 mg/kg (T)<br>Q4W<br>N = 3 | 3a<br>15 mg/kg (M) +<br>1 mg/kg (T)<br>Q4W<br>N = 12 | 3b<br>10 mg/kg (M) +<br>3 mg/kg (T)<br>Q4W<br>N = 3 | 4<br>20 mg/kg (M) +<br>1 mg/kg (T)<br>Q4W<br>N = 11 | 4a<br>15 mg/kg (M) +<br>3 mg/kg (T)<br>Q4W<br>N = 13 | 5<br>15 mg/kg (M) +<br>10 mg/kg (T)<br>Q4W<br>N = 9 |
| Complete Response | 0 (0.0%) | 0 (0.0%) | 0 (0.0%) | 0 (0.0%) | 0 (0.0%) | 0 (0.0%) | 0 (0.0%) |
| Partial Response | 0 (0.0%) | 1 (33.3%) | 4 (33.3%) | 1 (33.3%) | 3 (27.3%) | 4 (30.8%) | 2 (22.2%) |
| Stable Disease | 0 (0.0%) | 1 (33.3%) | 4 (33.3%) | 1 (33.3%) | 2 (18.2%) | 3 (23.1%) | 1 (11.1%) |
| Progressive Disease | 3 (100%) | 1 (33.3%) | 1 (8.3%) | 1 (33.3%) | 4 (36.4%) | 4 (30.8%) | 6 (66.7%) |
| Not Evaluable | 0 (0.0%) | 0 (0.0%) | 3 (25.0%) | 0 (0.0%) | 2 (18.2%) | 2 (15.4%) | 0 (0.0%) |

| | MEDI4736 (M) and Tremelimumab (T) Cohort | | | |
|---|---|---|---|---|
| | 5a<br>20 mg/kg (M) +<br>3 mg/kg (T)<br>Q4W<br>N = 6 | 8<br>10 mg/kg (M) +<br>1 mg/kg (T)<br>Q2W<br>N = 10 | 9<br>10 mg/kg (M) +<br>3 mg/kg (T)<br>Q2W<br>N = 9 | All Cohorts<br>N = 79 |
| Complete Response | 0 (0.0%) | 0 (0.0%) | 0 (0.0%) | 0 (0.0%) |
| Partial Response | 1 (16.7%) | 0 (0.0%) | 2 (22.2%) | 18 (22.8%) |
| Stable Disease | 2 (33.3%) | 3 (30.0%) | 2 (22.2%) | 19 (24.1%) |
| Progressive Disease | 1 (16.7%) | 5 (50.0%) | 4 (44.4%) | 30 (38.0%) |
| Not Evaluable | 2 (33.3%) | 2 (20.0%) | 1 (11.1%) | 12 (15.2%) |

TABLE 7

Best Overall Response - PD-L1 Positive Subjects
Response Evaluable Population

| | MEDI4736 (M) and Tremelimumab (T) Cohort | | | | | | |
|---|---|---|---|---|---|---|---|
| | 1a<br>3 mg/kg (M) +<br>1 mg/kg (T)<br>Q4W<br>N = 0 | 2a<br>10 mg/kg (M) +<br>1 mg/kg (T)<br>Q4W<br>N = 0 | 3a<br>15 mg/kg (M) +<br>1 mg/kg (T)<br>Q4W<br>N = 2 | 3b<br>10 mg/kg (M) +<br>3 mg/kg (T)<br>Q4W<br>N = 0 | 4<br>20 mg/kg (M) +<br>1 mg/kg (T)<br>Q4W<br>N = 4 | 4a<br>15 mg/kg (M) +<br>3 mg/kg (T)<br>Q4W<br>N = 0 | 5<br>15 mg/kg (M) +<br>10 mg/kg (T)<br>Q4W<br>N = 3 |
| Complete Response | 0 (0.0%) | 0 (0.0%) | 0 (0.0%) | 0 (0.0%) | 0 (0.0%) | 0 (0.0%) | 0 (0.0%) |
| Partial Response | 0 (0.0%) | 0 (0.0%) | 0 (0.0%) | 0 (0.0%) | 3 (75.0%) | 0 (0.0%) | 1 (33.3%) |
| Stable Disease | 0 (0.0%) | 0 (0.0%) | 1 (50.0%) | 0 (0.0%) | 1 (25.0%) | 0 (0.0%) | 1 (33.3%) |
| Progressive Disease | 0 (0.0%) | 0 (0.0%) | 0 (0.0%) | 0 (0.0%) | 0 (0.0%) | 0 (0.0%) | 1 (33.3%) |
| Not Evaluable | 0 (0.0%) | 0 (0.0%) | 1 (50.0%) | 0 (0.0%) | 0 (0.0%) | 0 (0.0%) | 0 (0.0%) |

TABLE 7-continued

Best Overall Response - PD-L1 Positive Subjects
Response Evaluable Population

| | MEDI4736 (M) and Tremelimumab (T) Cohort | | | |
|---|---|---|---|---|
| | 5a<br>20 mg/kg (M) +<br>3 mg/kg (T)<br>Q4W<br>N = 2 | 8<br>10 mg/kg (M) +<br>1 mg/kg (T)<br>Q2W<br>N = 1 | 9<br>10 mg/kg (M) +<br>3 mg/kg (T)<br>Q2W<br>N = 4 | All Cohorts<br>N = 16 |
| Complete Response | 0 (0.0%) | 0 (0.0%) | 0 (0.0%) | 0 (0.0%) |
| Partial Response | 0 (0.0%) | 0 (0.0%) | 2 (50.0%) | 6 (37.5%) |
| Stable Disease | 1 (50.0%) | 0 (0.0%) | 1 (25.0%) | 5 (31.3%) |
| Progressive Disease | 0 (0.0%) | 1 (100%) | 0 (0.0%) | 2 (12.5%) |
| Not Evaluable | 1 (50.0%) | 0 (0.0%) | 1 (25.0%) | 3 (18.8%) |

TABLE 8

Best Overall Response - PD-L Negative Subjects
Response Evaluable Population

| | MEDI4736 (M) and Tremelimumab (T) Cohort | | | | | | |
|---|---|---|---|---|---|---|---|
| | 1a<br>3 mg/kg (M) +<br>1 mg/kg (T)<br>Q4W<br>N = 2 | 2a<br>10 mg/kg (M) +<br>1 mg/kg (T)<br>Q4W<br>N = 3 | 3a<br>15 mg/kg (M) +<br>1 mg/kg (T)<br>Q4W<br>N = 6 | 3b<br>10 mg/kg (M) +<br>3 mg/kg (T)<br>Q4W<br>N = 3 | 4<br>20 mg/kg (M) +<br>1 mg/kg (T)<br>Q4W<br>N = 5 | 4a<br>15 mg/kg (M) +<br>3 mg/kg (T)<br>Q4W<br>N = 6 | 5<br>15 mg/kg (M) +<br>10 mg/kg (T)<br>Q4W<br>N = 3 |
| Complete Response | 0 (0.0%) | 0 (0.0%) | 0 (0.0%) | 0 (0.0%) | 0 (0.0%) | 0 (0.0%) | 0 (0.0%) |
| Partial Response | 0 (0.0%) | 1 (33.3%) | 3 (50.0%) | 1 (33.3%) | 0 (0.0%) | 3 (50.0%) | 1 (33.3%) |
| Stable Disease | 0 (0.0%) | 1 (33.3%) | 1 (16.7%) | 1 (33.3%) | 1 (20.0%) | 1 (16.7%) | 0 (0.0%) |
| Progressive Disease | 2 (100%) | 1 (33.3%) | 1 (16.7%) | 1 (33.3%) | 3 (60.0%) | 1 (16.7%) | 2 (66.7%) |
| Not Evaluable | 0 (0.0%) | 0 (0.0%) | 1 (16.7%) | 0 (0.0%) | 1 (20.0%) | 1 (16.7%) | 0 (0.0%) |

| | MEDI4736 (M) and Tremelimumab (T) Cohort | | | |
|---|---|---|---|---|
| | 5a<br>20 mg/kg (M) +<br>3 mg/kg (T)<br>Q4W<br>N = 2 | 8<br>10 mg/kg (M) +<br>1 mg/kg (T)<br>Q2W<br>N = 4 | 9<br>10 mg/kg (M) +<br>3 mg/kg (T)<br>Q2W<br>N = 1 | All Cohorts<br>N = 35 |
| Complete Response | 0 (0.0%) | 0 (0.0%) | 0 (0.0%) | 0 (0.0%) |
| Partial Response | 0 (0.0%) | 0 (0.0%) | 0 (0.0%) | 9 (25.7%) |
| Stable Disease | 1 (50.0%) | 2 (50.0%) | 1 (100%) | 9 (25.7%) |
| Progressive Disease | 1 (50.0%) | 1 (25.0%) | 0 (0.0%) | 13 (37.1%) |
| Not Evaluable | 0 (0.0%) | 1 (25.0%) | 0 (0.0%) | 4 (11.4%) |

TABLE 9

Best Overall Response - PD-L1 NA Subjects
Response Evaluable Population

| | MEDI4736 (M) and Tremelimumab (T) Cohort | | | | | | |
|---|---|---|---|---|---|---|---|
| | 1a<br>3 mg/kg (M) +<br>1 mg/kg (T)<br>Q4W<br>N = 1 | 2a<br>10 mg/kg (M) +<br>1 mg/kg (T)<br>Q4W<br>N = 0 | 3a<br>15 mg/kg (M) +<br>1 mg/kg (T)<br>Q4W<br>N = 4 | 3b<br>10 mg/kg (M) +<br>3 mg/kg (T)<br>Q4W<br>N = 0 | 4<br>20 mg/kg (M) +<br>1 mg/kg (T)<br>Q4W<br>N = 2 | 4a<br>15 mg/kg (M) +<br>3 mg/kg (T)<br>Q4W<br>N = 7 | 5<br>15 mg/kg (M) +<br>10 mg/kg (T)<br>Q4W<br>N = 3 |
| Complete Response | 0 (0.0%) | 0 (0.0%) | 0 (0.0%) | 0 (0.0%) | 0 (0.0%) | 0 (0.0%) | 0 (0.0%) |

TABLE 9-continued

Best Overall Response - PD-L1 NA Subjects
Response Evaluable Population

| | | | | | | | |
|---|---|---|---|---|---|---|---|
| Partial Response | 0 (0.0%) | 0 (0.0%) | 1 (25.0%) | 0 (0.0%) | 0 (0.0%) | 1 (14.3%) | 0 (0.0%) |
| Stable Disease | 0 (0.0%) | 0 (0.0%) | 2 (50.0%) | 0 (0.0%) | 0 (0.0%) | 2 (28.6%) | 0 (0.0%) |
| Progressive Disease | 1 (100%) | 0 (0.0%) | 0 (0.0%) | 0 (0.0%) | 1 (50.0%) | 3 (42.9%) | 3 (100%) |
| Not Evaluable | 0 (0.0%) | 0 (0.0%) | 1 (25.0%) | 0 (0.0%) | 1 (50.0%) | 1 (14.3%) | 0 (0.0%) |

| | MEDI4736 (M) and Tremelimumab (T) Cohort | | | |
|---|---|---|---|---|
| | 5a<br>20 mg/kg (M) +<br>3 mg/kg (T)<br>Q4W<br>N = 2 | 8<br>10 mg/kg (M) +<br>1 mg/kg (T)<br>Q2W<br>N = 5 | 9<br>10 mg/kg (M) +<br>3 mg/kg (T)<br>Q2W<br>N = 4 | All Cohorts<br>N = 28 |
| Complete Response | 0 (0.0%) | 0 (0.0%) | 0 (0.0%) | 0 (0.0%) |
| Partial Response | 1 (50.0%) | 0 (0.0%) | 0 (0.0%) | 3 (10.7%) |
| Stable Disease | 0 (0.0%) | 1 (20.0%) | 0 (0.0%) | 5 (17.9%) |
| Progressive Disease | 0 (0.0%) | 3 (60.0%) | 4 (100%) | 15 (53.6%) |
| Not Evaluable | 1 (50.0%) | 1 (20.0%) | 0 (0.0%) | 5 (17.9%) |

Those skilled in the art will recognize, or be able to ascertain using no more than routine experimentation, many equivalents to the specific aspects of the disclosure described herein. Such equivalents are intended to be encompassed by the following claims.

Various publications are cited herein, the disclosures of which are incorporated by reference in their entireties.

Although the foregoing invention has been described in some detail by way of illustration and example for purposes of clarity of understanding, it will be obvious that certain changes and modifications can be practiced within the scope of the appended claims.

```
SEQUENCE LISTING
MEDI4736 VL
                                           SEQ ID NO: 1
EIVLTQSPGTLSLSPGERATLSCRASQRVSSSYLAWYQQKPGQAPRLLIY

DASSRATGIPDRFSGSGSGTDFTLTISRLEPEDFAVYYCQQYGSLPWTFG

QGTKVEIK

MEDI4736 VH
                                           SEQ ID NO: 2
EVQLVESGGGLVQPGGSLRLSCAASGFTFSRYWMSWVRQAPGKGLEWVAN

IKQDGSEKYYVDSVKGRFTISRDNAKNSLYLQMNSLRAEDTAVYYCAREG

GWFGELAFDYWGQGTLVTVSS

MEDI4736 VH CDR1
                                           SEQ ID NO: 3
RYWMS

MEDI4736 VH CDR2
                                           SEQ ID NO: 4
NIKQDGSEKYYVDSVKG

MEDI4736 VH CDR3
                                           SEQ ID NO: 5
EGGWFGELAFDY

MEDI4736 VL CDR1
                                           SEQ ID NO: 6
RASQRVSSSYLA

MEDI4736 VL CDR2
                                           SEQ ID NO: 7
DASSRAT

MEDI4736 VL CDR3
                                           SEQ ID NO: 8
QQYGSLPWT

Tremelimumab VL
                                           SEQ ID NO: 9
PSSLSASVGDRVTITCRASQSINSYLDWYQQKPGKAPKLLIYAASSLQSG

VPSRFSGSGSGTDFTLTISSLQPEDFATYYCQQYYSTPFTFGPGTKVEIK

RTVAAPSVFIFPPSDEQLKSGTASVVCLLNNFYPREAKV

Tremelimumab VH
                                          SEQ ID NO: 10
GVVQPGRSLRLSCAASGFTFSSYGMHWVRQAPGKGLEWVAVIWYDGSNKY

YADSVKGRFTISRDNSKNTLYLQMNSLRAEDTAVYYCARDPRGATLYYYY

YGMDVWGQGTTVTVSSASTKGPSVFPLAPCSRSTSESTAALGCLVKDYFP

EPVTVSWNSGALTSGVH

Tremelimumab VH CDR1
                                          SEQ ID NO: 11
GFTFSSYGMH Tremelimumab VH CDR2
                                          SEQ ID NO: 12
VIWYDGSNKYYADSV Tremelimumab VH CDR3
                                          SEQ ID NO: 13
TAVYYCARDPRGATLYYYYYGMDV Tremelimumab VL CDR1
                                          SEQ ID NO: 14
RASQSINSYLD Tremelimumab VL CDR2
                                          SEQ ID NO: 15
AASSLQS Tremelimumab VL CDR3
                                          SEQ ID NO: 16
QQYYSTPFT
```

What is claimed is:

1. A method of treating non-small cell lung carcinoma (NSCLC) in a human patient, comprising administering MEDI4736 or an antigen-binding fragment thereof and tremelimumab or an antigen-binding fragment thereof to the patient, wherein the dose of MEDI4736 or an antigen-binding fragment thereof is 20-fold the dose of tremelimumab or an antigen-binding fragment thereof, wherein the MEDI4736 or an antigen-binding fragment thereof is administered about 1 hour following administration of tremelimumab or an antigen-binding fragment thereof, wherein the MEDI4736 or an antigen-binding fragment thereof and tremelimumab or an antigen-binding fragment thereof are administered every 4 weeks for at least up to 16 weeks, and wherein the dose of MEDI4736 or an antigen-binding fragment thereof is 1500 mg and the dose of tremelimumab or an antigen-binding fragment thereof is 75 mg.

2. The method of claim 1, further comprising administering 1500 mg of MEDI4736 or an antigen-binding fragment thereof every two weeks after 16 weeks.

3. The method of claim 2, wherein the total length of treatment is 52 weeks.

4. The method of claim 1, wherein the NSCLC is refractory to at least one chemotherapeutic agent prior to the administration of MEDI4736 or an antigen-binding fragment thereof and tremelimumab or an antigen-binding fragment thereof.

5. The method of claim 4, wherein the chemotherapeutic agent is Vemurafenib, Erlotinib, Afatinib, Cetuximab, Carboplatin, Bevacizumab, Gefitinib, or Pemetrexed.

6. The method of claim 1, wherein the patient is immunotherapy-naïve prior to the administration of MEDI4736 or an antigen-binding fragment thereof and tremelimumab or an antigen-binding fragment thereof.

7. The method of claim 1, wherein the administration of MEDI4736 or an antigen-binding fragment thereof is by intravenous infusion.

8. The method of claim 1, wherein the administration of tremelimumab or an antigen-binding fragment thereof is by intravenous infusion.

9. The method of claim 1, wherein the administrations reduce tumor size by at least about 10% relative to tumor size as measured prior to the administration of MEDI4736 or an antigen-binding fragment thereof and tremelimumab or an antigen-binding fragment thereof.

10. The method of claim 1, wherein the administrations reduce tumor size by about 25% relative to tumor size as measured prior to the administration of MEDI4736 or an antigen-binding fragment thereof and tremelimumab or an antigen-binding fragment thereof.

11. The method of claim 10, wherein the NSCLC is squamous or non-squamous.

12. The method of claim 1, wherein the human patient has locally advanced unresectable or metastatic NSCLC.

13. The method of claim 1, wherein the administrations reduce tumor size by about 50% relative to tumor size as measured prior to the administration of MEDI4736 or an antigen-binding fragment thereof and tremelimumab or an antigen-binding fragment thereof.

* * * * *

UNITED STATES PATENT AND TRADEMARK OFFICE
CERTIFICATE OF CORRECTION

| | | |
|---|---|---|
| PATENT NO. | : 11,446,377 B2 | Page 1 of 1 |
| APPLICATION NO. | : 16/256022 | |
| DATED | : September 20, 2022 | |
| INVENTOR(S) | : Narwal et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 194 days.

Signed and Sealed this
Fourth Day of February, 2025

Coke Morgan Stewart
*Acting Director of the United States Patent and Trademark Office*